(12) United States Patent
Silver et al.

(10) Patent No.: US 11,826,206 B2
(45) Date of Patent: Nov. 28, 2023

(54) LIGHTING DEVICES FOR HANDHELD SURGICAL INSTRUMENTS, HOLSTERS FOR SURGICAL INSTRUMENTS WITH LIGHTING DEVICES AND KITS CONTAINING SURGICAL INSTRUMENTS AND LIGHTING DEVICES

(71) Applicant: Pathy Medical, LLC, Shelton, CT (US)

(72) Inventors: Mikiya Silver, New Haven, CT (US); Gennady Kleyman, Brooklyn, NY (US); Vinod V. Pathy, Madison, CT (US)

(73) Assignee: Pathy Medical, LLC, Shelton, CT (US)

( * ) Notice: Subject to any disclaimer, the term of this patent is extended or adjusted under 35 U.S.C. 154(b) by 0 days.

(21) Appl. No.: 17/898,909

(22) Filed: Aug. 30, 2022

(65) Prior Publication Data
US 2023/0040314 A1    Feb. 9, 2023

Related U.S. Application Data

(63) Continuation of application No. 16/823,500, filed on Mar. 19, 2020, now Pat. No. 11,471,243.
(Continued)

(51) Int. Cl.
*A61B 90/35*    (2016.01)
*F21S 9/02*    (2006.01)
(Continued)

(52) U.S. Cl.
CPC ............... *A61B 90/35* (2016.02); *F21S 9/02* (2013.01); *F21V 21/0885* (2013.01);
(Continued)

(58) Field of Classification Search
CPC ........ A61B 90/35; F21S 9/02; F21V 21/0885; F21V 33/0068
See application file for complete search history.

(56) References Cited

U.S. PATENT DOCUMENTS 299,277 A * 5/1884 Sheridan ................ A61B 1/06
220/2.2
5,448,459 A * 9/1995 Rogers ................ F21V 21/145
362/120
(Continued)

FOREIGN PATENT DOCUMENTS

| EP | 0905432 A2 | 3/1999 |
|---|---|---|
| KR | 20130034068 A | 4/2013 |
| WO | 2017-001379 | 1/2017 |

OTHER PUBLICATIONS

International Search Report and Written Opinion issued in corresponding PCT Patent Application No. PCT/US2020/023629, dated Jul. 8, 2020.
(Continued)

*Primary Examiner* — Bryon T Gyllstrom
(74) *Attorney, Agent, or Firm* — Locke Lord LLP; Scott D. Wofsy; Michael J. Pollack

(57) ABSTRACT

Lighting devices are disclosed for use with handheld surgical instruments, along with holsters for supporting surgical instruments with lighting devices thereon and kits containing surgical instruments and lighting devices.

18 Claims, 65 Drawing Sheets

Related U.S. Application Data

(60) Provisional application No. 62/824,565, filed on Mar. 27, 2019.

(51) Int. Cl.
    | | |
    |---|---|
    | *F21V 21/088* | (2006.01) |
    | *F21V 33/00* | (2006.01) |
    | *F21Y 115/10* | (2016.01) |
    | *F21W 131/20* | (2006.01) |

(52) U.S. Cl.
    CPC ..... *F21V 33/0068* (2013.01); *F21W 2131/20* (2013.01); *F21Y 2115/10* (2016.08)

(56) References Cited

U.S. PATENT DOCUMENTS

| | | |
|---|---|---|
| 5,785,408 A | 7/1998 | Tseng |
| 5,845,986 A | 12/1998 | Breen |
| 7,510,524 B2 | 3/2009 | Vayser et al. |
| 9,851,060 B2 | 12/2017 | Pathy |
| 10,068,173 B2 | 9/2018 | Vayser et al. |
| 10,716,642 B1 | 7/2020 | Pathy et al. |
| 2002/0105794 A1 | 8/2002 | Hanscom et al. |
| 2007/0047223 A1* | 3/2007 | Mundhra ................ F21L 4/00 362/103 |
| 2008/0266845 A1 | 10/2008 | Wu et al. |
| 2013/0197317 A1* | 8/2013 | Daniel ................ A61B 1/0684 600/249 |
| 2013/0331657 A1 | 12/2013 | Basson et al. |
| 2016/0058525 A1* | 3/2016 | Nichols ................ A61C 1/088 433/29 |
| 2018/0135814 A1 | 5/2018 | Pathy |
| 2018/0209623 A1* | 7/2018 | Strölin ................ F21V 23/0471 |
| 2020/0121412 A1* | 4/2020 | Pathy ................ F21V 19/0015 |
| 2020/0306001 A1 | 10/2020 | Silver et al. |

OTHER PUBLICATIONS

Extended European Search Report issued, of the European Patent Office, dated Jan. 19, 2023, in corresponding European Patent Application No. 20777547.9.

\* cited by examiner

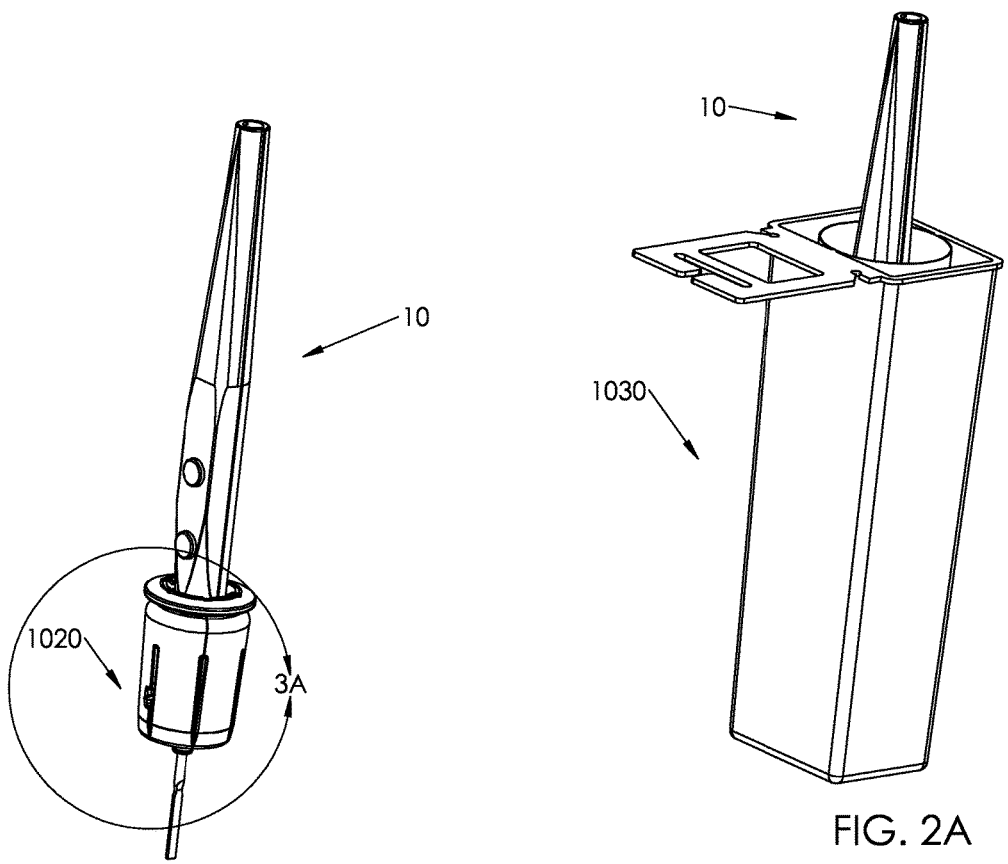
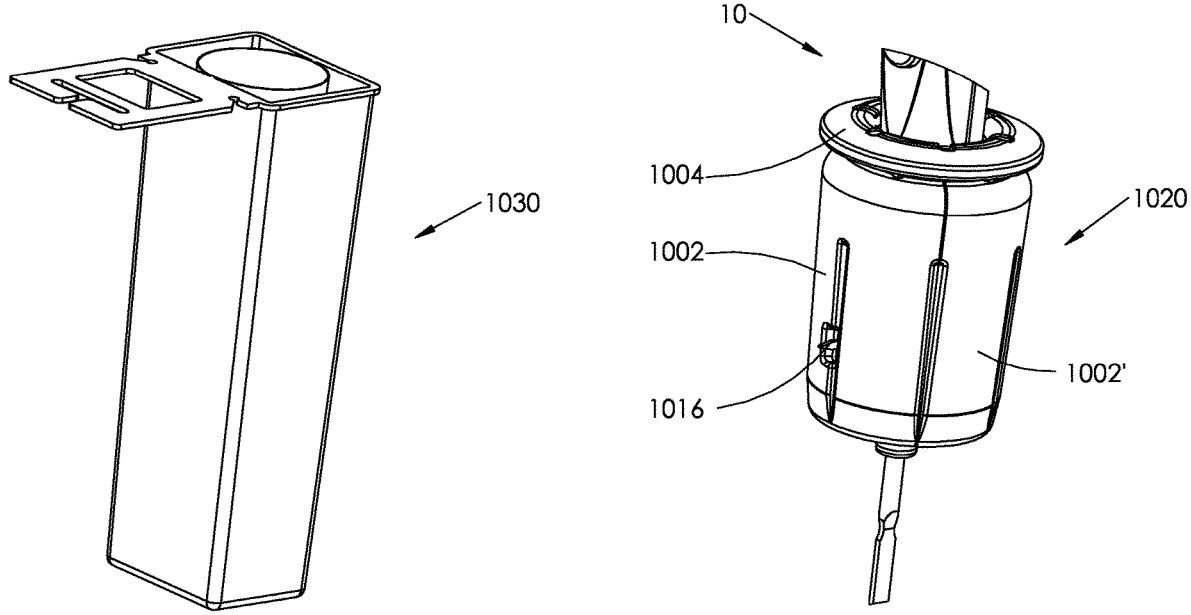
FIG. 1A
FIG. 2A
FIG. 3A

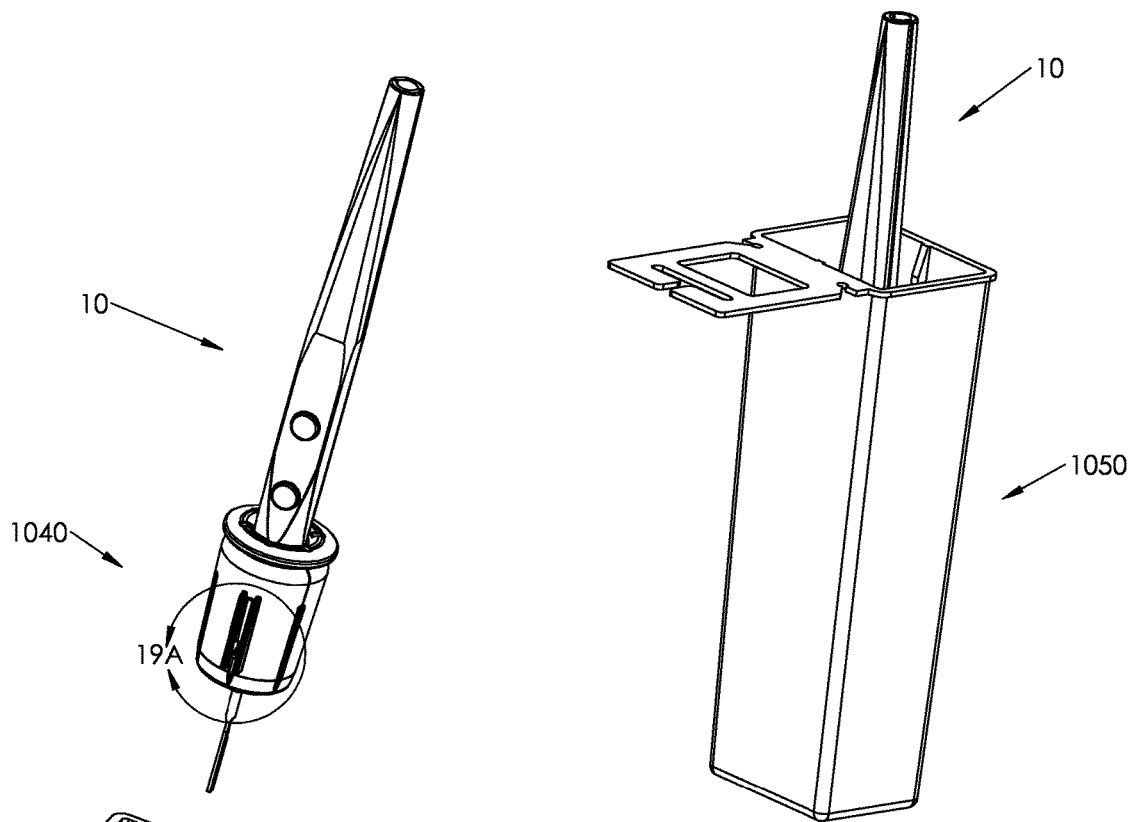
FIG. 18A
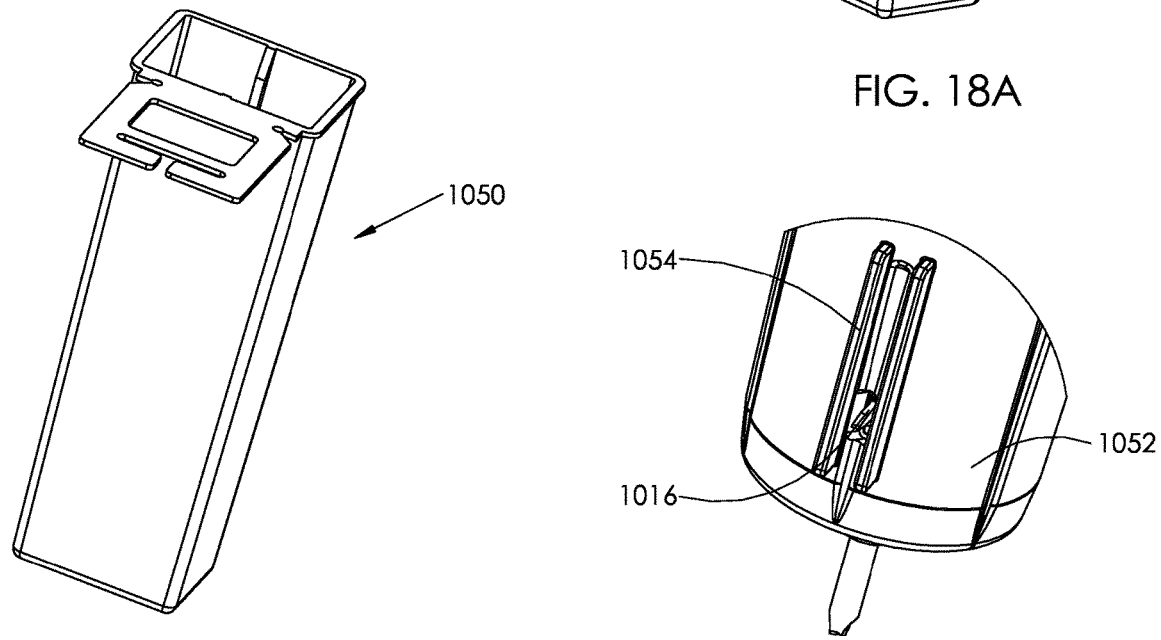
FIG. 17A
FIG. 19A

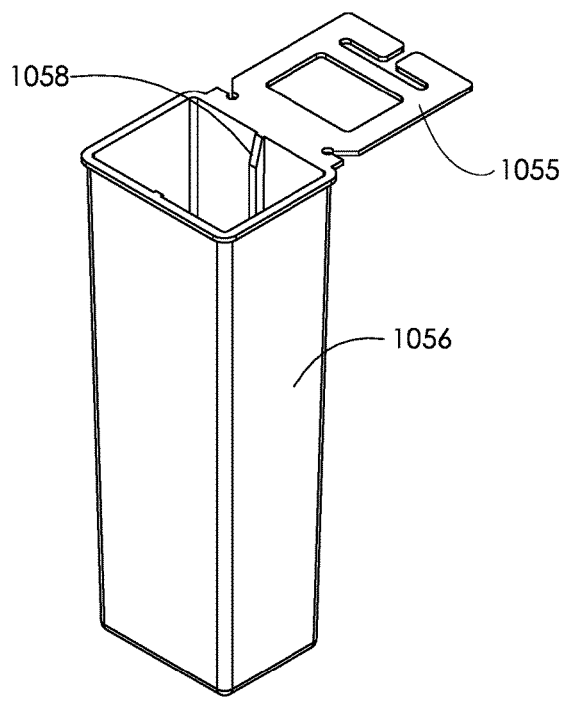
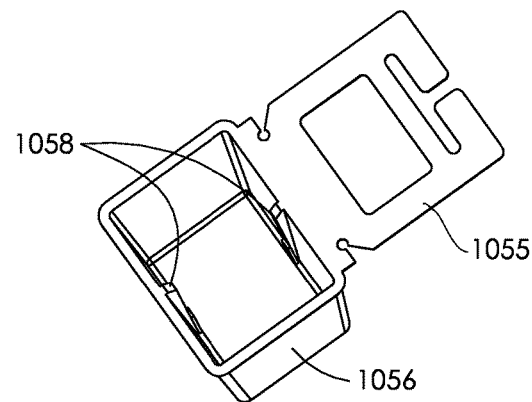
FIG. 23A
FIG. 24A
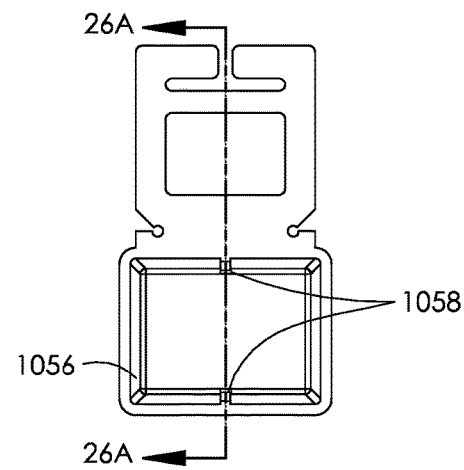
FIG. 25A
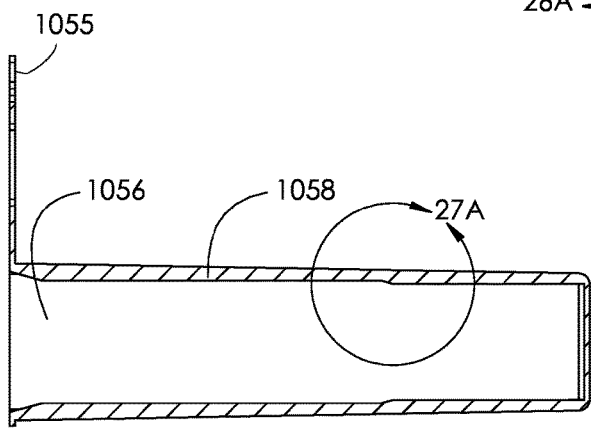
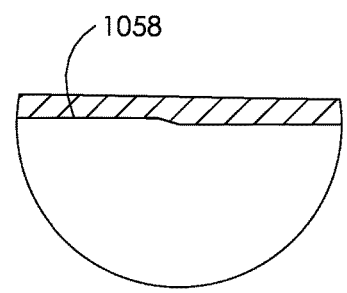
FIG. 26A
FIG. 27A

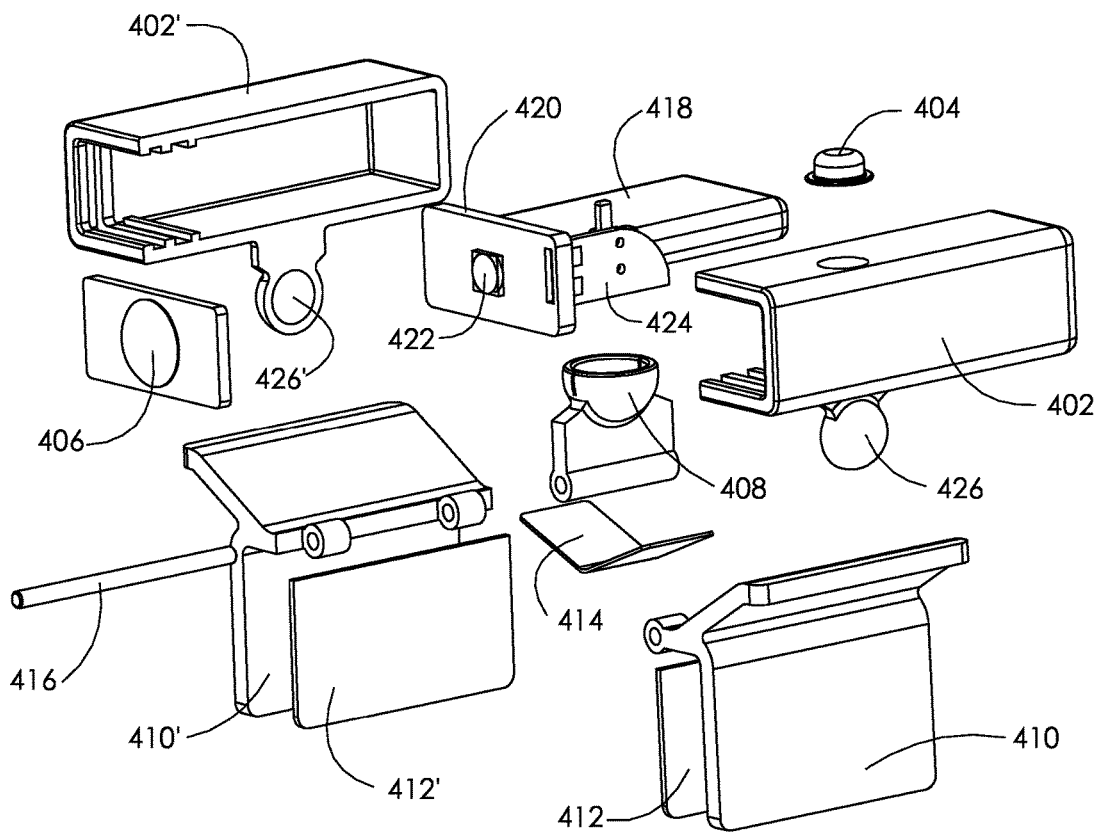
FIG. 77
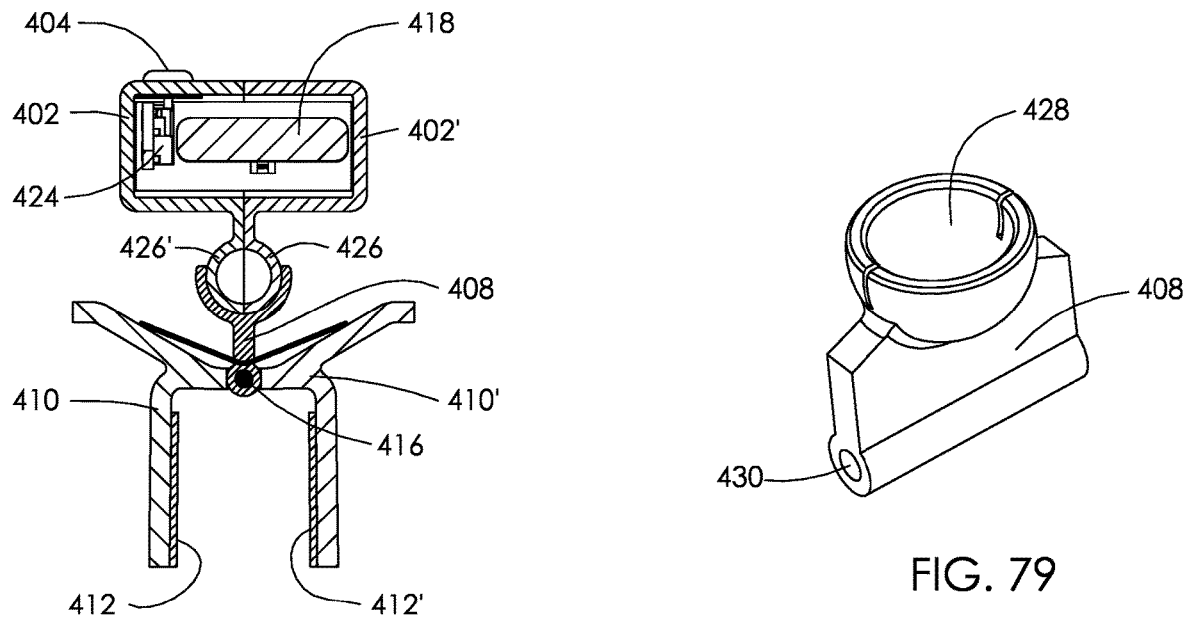
FIG. 78
FIG. 79

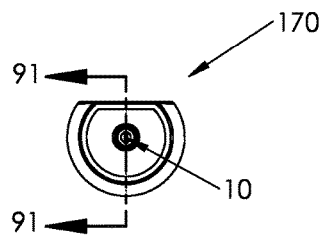
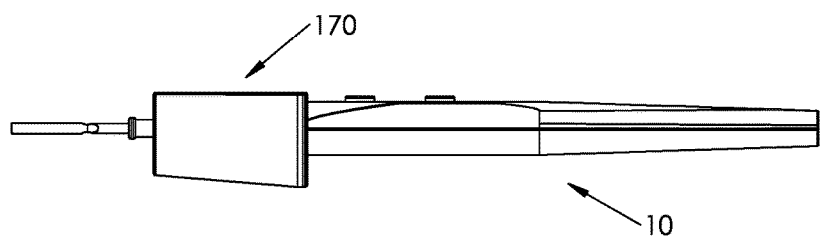
FIG. 86　　　　　　　FIG. 87
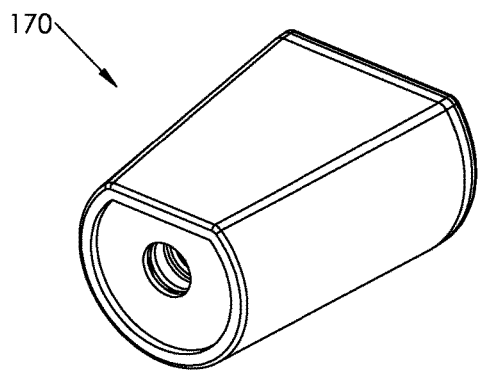
FIG. 88
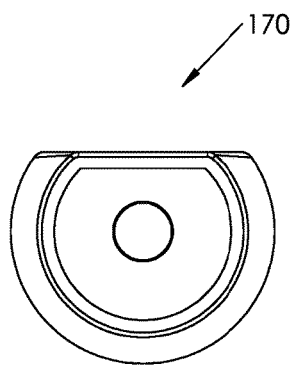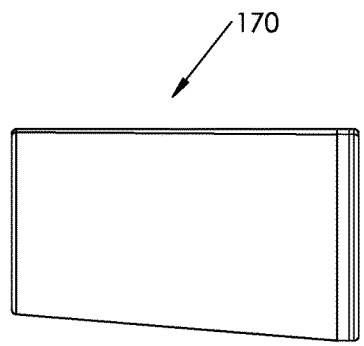
FIG. 89　　　　　　　FIG. 90

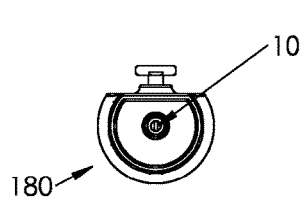
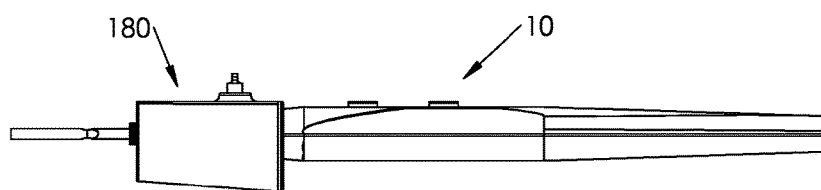
FIG. 96  FIG. 97
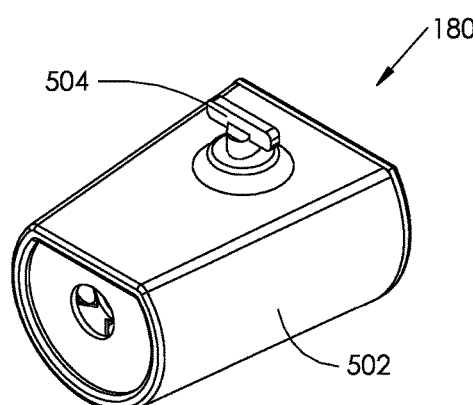
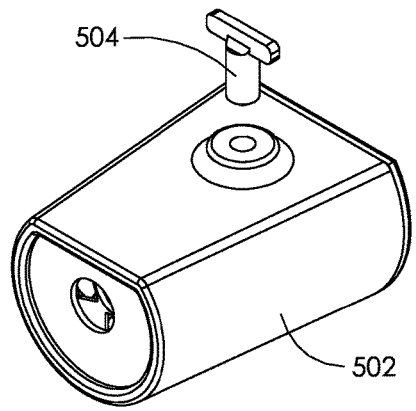
FIG. 98  FIG. 99
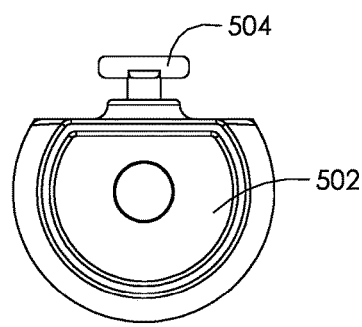
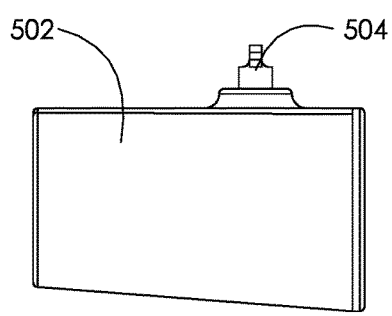
FIG. 100  FIG. 101

LIGHTING DEVICES FOR HANDHELD SURGICAL INSTRUMENTS, HOLSTERS FOR SURGICAL INSTRUMENTS WITH LIGHTING DEVICES AND KITS CONTAINING SURGICAL INSTRUMENTS AND LIGHTING DEVICES

CROSS-REFERENCE TO RELATED APPLICATIONS

This Application is a Continuation of U.S. patent application Ser. No. 16/823,500, filed on Mar. 19, 2020, which claims the benefit of priority to U.S. Provisional Patent Application Ser. No. 62/824,565, filed Mar. 27, 2019, the disclosures of which are herein incorporated by reference.

BACKGROUND OF THE INVENTION

1. Field of the Invention

The subject invention is directed to surgical instrumentation, and more particularly, to lighting devices for use with surgical instruments, holsters for supporting such instruments with lighting devices thereon and kits containing surgical instruments and lighting devices.

2. Description of Related Art

Lighting devices are typically used to allow an operator to illuminate, and thus more precisely control and enhance, a space or area with a lighted field of view. In many situations, a lighting device can be used to illuminate a closed or confined space that would not regularly receive an adequate amount of light, if at all.

Existing lighting devices are connectable to a variety of tools, including, for example, medical devices and hand tools such as screwdrivers, to illuminate the area in which the device or tool is to be used. Such lighting devices and light sources include attachments that have an electrical cord extending therefrom that in turn is connectable to a power source, attachments that are battery powered, and light sources integrally formed within a tool to direct light on a specific field of view.

In medical practice, lighting devices are used to direct light at a specific area being operated on or examined. For example, lighting devices can be used in conjunction with handheld electrosurgical devices, such as an electrosurgical pencils or more specifically a BOVIE® pencil used to incise through tissues, and a variety of other operative instruments, such as retractors, irrigators and forceps. Lighted retractors are commonly used during surgeries to help illuminate surgical cavities or other areas within the surgical field.

The inventors have discerned a number of disadvantages of previously known lighting devices. For example, known lighting devices that include a light source integrally formed therein are generally expensive, bulky, and can cause injury. Known cordless and corded lighting devices add significant bulk to a tool, preventing a user from manipulating the tool with the precision required in many situations and preventing the user from extending the tool into tight spaces.

Additionally, many lighting devices, especially corded lighting devices, require constant repositioning, are cumbersome, are assistant-dependent to hold or re-position, and can be disruptive to a surgical field. Further, corded lighting devices as well as light sources integrally formed within a tool can become hot, burn the user and/or the patient, and possibly even cause a fire.

Headlights can be used as an alternative to a lighting device during a surgical procedure. However, similar to other lighting devices, headlights are bulky, often require cables to connect to a power source, require constant readjustment, and can pose a potential safety hazard. Moreover, being worn on the head of the surgeon, they are at a distance from the surgical field, decreasing their effectiveness, and can be cumbersome to the user, and cause fatigue if worn for an extended period of time.

A particularly useful lighting device for attachment to a handheld electrosurgical device, and in particular, for use with an electrosurgical pencil, is disclosed in U.S. Pat. No. 9,851,060, the disclosure of which is herein incorporated by reference in its entirety. The subject invention provides improvements to and accessories for enhancing the utility and effectiveness of the lighting device disclosed therein, and kits containing such devices and accessories.

SUMMARY OF THE DISCLOSURE

The subject invention is directed to surgical instrumentation, and more particularly, to new and useful lighting devices for use with surgical instruments. It will be readily appreciated that many of the lighting devices disclosed herein are designed to work with a variety of surgical devices that are available on the market, including a variety of handheld electrosurgical instruments, each of which has a slightly different geometry.

In one embodiment of the subject invention, the lighting device includes an elongated light housing defining a longitudinal illumination axis and having an interior chamber supporting an LED light source, an attachment mechanism for detachably engaging the light housing to a surgical instrument at any location along a longitudinal axis thereof, and a connector for operatively connecting the light housing to the attachment mechanism.

In one embodiment, the connector is a post that extends vertically upward from the attachment mechanism, and the light housing is pivotably connected to an upper end of the post. For example, the light housing can be mounted for pivotal movement about a pivot axis that extends perpendicular to the longitudinal illumination axis of the light housing. Alternatively, the light housing could be rotationally connected to an upper end of the post so as to orient the illumination axis of the light housing with respect to the longitudinal axis of the surgical instrument. For example, a ball and socket joint can rotationally connect the light housing to the post.

In another embodiment of the invention, the post has a vertical height that is more than twice the vertical height of the light housing, so that if the light housing is attached to a proximal end portion of the surgical instrument the vertical height of the post will extend above the hand of a user so that the longitudinal illumination axis of the light housing intersects with the longitudinal axis of the surgical instrument adjacent a distal tip portion thereof.

In an embodiment of the invention, the attachment mechanism is a clamping mechanism that includes a pair of spring biased wings adapted for pivotal movement about an axis that extends parallel to the longitudinal axis of the light housing between an open position for receiving a portion of the surgical instrument and a closed position for engaging the portion of the surgical instrument.

In another embodiment of the invention, the attachment mechanism is a clamping mechanism that includes a pair of spring biased wings adapted for pivotal movement about an axis that extends perpendicular to the longitudinal axis of the light housing between an open position for receiving a section of a surgical drape or body tissue and a closed position for engaging the section of surgical drape or body tissue. It is envisioned that multiple light housings could be attached to a surgical drape and arranged around the perimeter of a surgical wound and the light housing could be angled to create arena lighting for the surgical site.

In other embodiments of the invention, the attachment mechanism can take the form of a hook and loop type fastening strap, an adhesive strip, or a cable tie consisting of a flexible tape with an integrated gear rack and having on one end a ratchet within an open case.

It is envisioned that the light housing could include a switch assembly for selectively activating the LED light source, and at least one battery for powering the LED light source. Alternatively, the light housing could include a power cord for connecting the light housing to an external power source for powering the LED light source. In addition, the light housing could support a camera within the interior chamber thereof for remotely viewing the surgical site.

The subject invention is also directed to a lighting device for attachment to a handheld surgical instrument that includes a substantially frusto-conical outer body portion having opposed proximal and distal ends, and defining a trapezoidal shaped planar upper surface portion for planar alignment with an upper surface of the surgical instrument so that a line of sight extending along the upper surface of the surgical instrument remains unobstructed by the lighting device. A securement ring can be located within the proximal end of the outer body portion for mechanically engaging the distal end portion of the surgical instrument. Alternatively, a securement screw can be located on the planar upper surface portion of the outer body portion for selectively engaging the distal end portion of the surgical instrument.

In another embodiment of the invention, an elongated securement beam is pivotably attached to the proximal end of the outer body portion about an axis that extends perpendicular to a longitudinal axis of the surgical instrument and it includes a proximal clasp for frictionally engaging a proximal end portion of the surgical instrument.

In another embodiment of the invention, a securement arm is rotationally attached to a proximal end cap of the outer body portion about an axis that extends parallel to a longitudinal axis of the surgical instrument and it includes a contact surface for frictionally engaging the distal end portion of the surgical instrument and an outer tang for selectively engaging a retaining boss projecting from the proximal end cap.

The lighting device could also include a compliant securement ring disposed within the outer body portion adjacent the proximal end thereof for frictionally engaging the surgical instrument within the interior bore of the inner body portion. Alternatively, the lighting device could include a securement ring disposed within outer body portion adjacent the proximal end thereof having a plurality of radially inwardly directed teeth for mechanically engaging the surgical instrument within the interior bore of the inner body portion.

It is envisioned that a non-contact switching mechanism can be housed within the interior cavity of the lighting device for activating the LED light sources. The non-contact switching mechanism would be selected from the group of switching mechanisms consisting of a Hall-effect sensor, a proximity sensor and a photosensor.

A Hall effect sensor is a transducer that varies its output voltage in response to a magnetic field. Hall-effect sensors are used for proximity switching, positioning, speed detection, and current sensing applications. In a Hall effect sensor, a thin strip of metal has a current applied along it. A proximity sensor often emits an electromagnetic field or a beam of electromagnetic radiation (infrared, for instance), and looks for changes in the field or return signal. The object being sensed is often referred to as the proximity sensor's target. Different proximity sensor targets demand different sensors.

The subject invention is also directed to a lighting device for attachment to a handheld surgical instrument that includes an elongated light housing defining a longitudinal axis and having an interior chamber supporting a battery powered LED light source, an attachment mechanism for detachably engaging the light housing on a proximal end portion of the surgical instrument, and an elongated light tube extending distally from the light housing and having a sleeve at a distal end thereof for receiving and surrounding a distal end portion of the surgical instrument In an embodiment of the invention, the elongated light tube and sleeve contain a polymer material that transmits light from the light housing to a distal end of the sleeve. In essence, the polymer functions as a waveguide (see, for example, U.S. Pat. Nos. 7,510,524 and 10,068,173). In another embodiment of the invention, the elongated light tube and sleeve contain a plurality of optical fibers that transmit light from the light housing to a distal end of the sleeve. Preferably, the optical fibers are distributed in spaced apart relationship about the periphery of the sleeve.

The subject invention is also directed to a lighting device for attachment to a handheld surgical instrument that includes an elongated light housing defining a longitudinal axis and having an interior chamber supporting a battery powered LED light source, an attachment mechanism for detachably engaging the light housing on a distal end portion of the surgical instrument, and an elongated light tube operatively associated with the light housing and including a distal end portion that is supported within the light housing for directing light from a distal end thereof, the light tube having a proximal coupling for connection with an external light source. Preferably, the light tube comprises a fiber optic cable, and the device further includes an external light source communicating with the coupling on the proximal end of the light tube. Moreover, the fiber optic cable would be attached to a capital equipment device housed outside the sterile field (permanent or multiuse device).

The subject invention is directed to a system for performing a surgical procedure that includes a surgical instrument, a battery powered lighting device configured for attachment on a distal end portion of the surgical instrument, and a holster for accommodating the surgical instrument with the lighting device attached thereto. It is envisioned that the lighting device could be a handheld electrosurgical instrument or the like, but the subject invention is not limited thereto. Preferably, the lighting device has a first switch for turning the lighting device on when it is attached to the surgical instrument and a second switch for turning the lighting device off when the surgical instrument and attached lighting device are inserted together into the holster.

In an embodiment of the invention, the holster is defined by an elongated body having an interior cavity with a reception bore formed therein that is dimensioned and configured to accommodate an outer periphery of the lighting device. The reception bore of the holster has a peripheral contact surface that interacts with the second switch of the lighting device when the surgical instrument is inserted into the holster with the lighting device attached thereto.

In another embodiment of the invention, the holster is defined by an elongated body having an interior cavity with interior guide structure extending along an interior surface thereof for interacting with corresponding exterior guide structure on an outer periphery of the lighting device, and a contact structure is associated with the interior guide structure for interacting with the second switch of the lighting device.

Preferably, the exterior guide structure is defined by a channel having opposed elongated rails, the interior guide structure is defined by a rib configured to fit between the rails of the channel, and the second switch of the lighting device is located within the channel and the contact structure is formed on the rib.

The subject invention is also directed to a kit for use in a surgical procedure that includes a packaging enclosure, a surgical instrument disposed within the enclosure, and at least one battery powered lighting device disposed within the enclosure and adapted for use with the surgical instrument. Preferably, the surgical instrument is a handheld electrosurgical instrument or the like. In an embodiment of the invention, the kit also includes a surgical matrix material disposed within the enclosure for use during the surgical procedure.

In another embodiment of the invention, the kit also includes an adapter disposed within the enclosure and configured for attaching the battery powered lighting device adjacent a distal end portion the surgical instrument. Preferably, the adapter includes a first body portion configured to engage a distal end portion of the surgical instrument at a position along a central axis thereof, and a second body portion configured to support the lighting device adjacent the distal end portion of the surgical instrument, such that an illumination axis of the lighting device angularly intersects the central axis of the surgical instrument. Here, the lighting device has an interior switch for turning the lighting device on when it is attached to the adapter.

In yet another embodiment of the invention, the kit also includes a holster disposed within the enclosure and configured to receive the surgical instrument with the battery powered lighting device attached to a distal end portion thereof. Here, the lighting device has an interior switch for turning the lighting device on when it is attached to the surgical instrument, and an exterior switch for turning the lighting device off when the surgical instrument and attached lighting device are inserted together into the holster.

The subject invention is also directed to a lighting device for attachment to a handheld surgical instrument that includes an elongated outer housing having opposed proximal and distal ends, an inner body disposed within the outer housing and defining an elongated interior cavity having a proximal opening for receiving a distal end portion of the surgical instrument, a light source located within the outer housing for directing light from the distal end thereof, a switch located within the outer housing adjacent the distal end thereof for activating the light source, and a deflectable contact leg formed integral with the inner body and configured to contact the switch upon insertion of the distal end portion of the surgical instrument into the interior cavity of the inner body to activate the light source.

The deflectable contact leg includes a radially inwardly projecting foot at a distal end thereof forming a ramped camming surface for easing insertion of the distal end portion of the surgical instrument into the interior cavity of the inner body. The lighting device further includes a biasing spring disposed within the outer housing for urging the contact leg toward the central axis of the interior cavity of the inner body, so that the contact leg is out of contact with the switch and positioned to interact with the distal end portion of the surgical instrument upon the insertion thereof. In one embodiment, the deflectable contact leg includes a radially outwardly projecting foot at a distal end thereof for contacting the switch upon the interaction of the contact leg with the distal end portion of the surgical instrument.

The lighting device further includes a spring biased engagement ring disposed within the outer housing and mounted for movement relative to the inner body and the outer housing between a first position to accommodate insertion of the distal end portion of the surgical instrument into the interior cavity of the inner body and a second position to engage and retain the distal end portion of the surgical instrument within the lighting device. The inner body includes an arcuate slot for accommodating the engagement ring within the outer housing. A projection extends radially outward from the engagement ring, through an access port in the outer housing for manually moving the engagement ring from the second position to the first position against the spring bias to accommodate insertion of the distal end portion of the surgical instrument into the interior cavity of the inner body.

A biasing spring is operatively associated with the engagement ring to bias the engagement ring into the second position. The biasing spring may be positioned between an inner periphery of the engagement ring and an exterior surface of the inner body, or the biasing spring may be positioned between an outer periphery of the engagement ring an interior surface of the outer housing. An inner peripheral surface section of the engagement ring is adapted to frictionally, resiliently or adhesively engage and retain the distal end portion of the surgical instrument.

Preferably, the light source is defined by a plurality of LED light sources arranged in a spaced relationship on a printed circuit board, and one or more of the LED light sources can provide light in a UV spectrum range. The switch is mounted on the printed circuit board and one or more battery cells are connected to the printed circuit board for delivering power to the light sources.

The subject invention is also directed to a lighting device for attachment to a handheld surgical instrument that includes an elongated outer housing having opposed proximal and distal ends, an inner body disposed within the outer housing and defining an elongated interior cavity having a proximal opening for receiving a distal end portion of the surgical instrument, a light source located within the outer housing for directing light from the distal end thereof upon insertion of the distal end portion of the surgical instrument into the interior cavity of the inner body, and a spring biased engagement ring disposed within the outer housing and mounted for movement relative to the inner body and the outer housing between a first position to accommodate insertion of the distal end portion of the surgical instrument into the interior cavity of the inner body and a second position to engage and retain the distal end portion of the surgical instrument within the lighting device.

The subject invention is also directed to a lighting device for attachment to a handheld surgical instrument that includes an elongated outer housing having opposed proximal and distal ends, an inner body disposed within the outer housing and defining an elongated interior cavity having a proximal opening for receiving a distal end portion of the surgical instrument, a light source located within the outer housing for directing light from the distal end thereof, a switch located within the outer housing adjacent the distal end thereof for activating the light source, a contact leg formed integral with the inner body and configured to contact the switch upon insertion of the distal end portion of the surgical instrument into the interior cavity of the inner body to activate the light source, and an engagement ring disposed within the outer housing and having a first position to accommodate insertion of the distal end portion of the surgical instrument into the interior cavity of the inner body and a second position to engage and retain the distal end portion of the surgical instrument within the lighting device.

Throughout the subject disclosure, an LED light source or LED light sources are described. In this regard, reference is being made to the concept of an "LED chip" which is a prefabricated array of LEDs. The advantage of using such a component is in the assembly costs and geometry, as it can be attached to a remote battery source. Moreover, a prefabricated chip will enable a one-sided Printed Circuit Board Assembly (PCBA), which would save on manufacturing time and cost, and increase production capacity.

These and other features of the subject invention will become more readily apparent to those having ordinary skill in the art to which the subject invention appertains from the following brief description of the drawings.

BRIEF DESCRIPTION OF THE DRAWINGS

So that those skilled in the art will readily understand how to make and use the lighting devices and accessories of the subject invention without undue experimentation, preferred embodiments thereof will be described in detail herein below with reference to the figures wherein:

FIGS. 71 through 79 illustrate another embodiment of a lighting device which includes a clamping mechanism for attachment to body tissue of a patient to illuminate the operating site;

FIGS. 84 through 93 illustrate yet another embodiment of a lighting device constructed in accordance with the subject invention, which includes a housing having a frusto-conical outer body portion with a trapezoidal shaped planar upper surface;

FIGS. 94 through 101 illustrate another embodiment of a lighting device, which includes a screw mechanism for securing the device to the distal end portion of a handheld surgical instrument;

FIGS. 1A through 16A illustrates a system for performing a surgical procedure which includes a battery powered lighting device configured for attachment on the distal end portion of a handheld surgical instrument and a holster for accommodating the surgical instrument with the lighting device attached thereto;

FIGS. 17A through 33A illustrates another system for performing a surgical procedure which includes another embodiment of a battery powered lighting device configured for attachment on the distal end portion of a handheld surgical instrument and a another embodiment of a holster for accommodating the surgical instrument with the lighting device attached thereto;

FIGS. 1B through 4B illustrate an embodiment of a kit that includes a blister package containing a surgical instrument and a lighting device;

FIGS. 5B through 8B illustrate another embodiment of a kit that includes a blister package containing a surgical instrument, two lighting devices and an adapter for mounting a lighting device on the surgical instrument;

FIGS. 9B through 12B illustrate another embodiment of a kit that includes a blister package containing a lighting devices and an adapter for mounting the lighting device on a surgical instrument;

FIGS. 13B through 16B illustrate another embodiment of a kit that includes a blister package containing a surgical instrument, a lighting device and a holster;

FIGS. 17B through 20B illustrate yet another embodiment of a kit that includes a blister package containing a surgical instrument, a lighting device, a holster and a piece of human matrix material;

FIGS. 1C through 14C illustrate another embodiment of a lighting device, which includes a contact leg configured to activate a switch and an engagement ring to engage and retain the distal end portion of a surgical instrument;

FIGS. 15C through 27C illustrate another embodiment of a lighting device, which includes a contact leg configured to activate a switch and an engagement ring to engage and retain the distal end portion of a surgical instrument; show top and side views of leaf spring 756; and FIGS. 28C through 40C illustrate yet another embodiment of a lighting device, which includes a contact leg configured to activate a switch and an engagement ring to engage and retain the distal end portion of a surgical instrument.

DETAILED DESCRIPTION OF THE PREFERRED EMBODIMENTS

Figure 1:
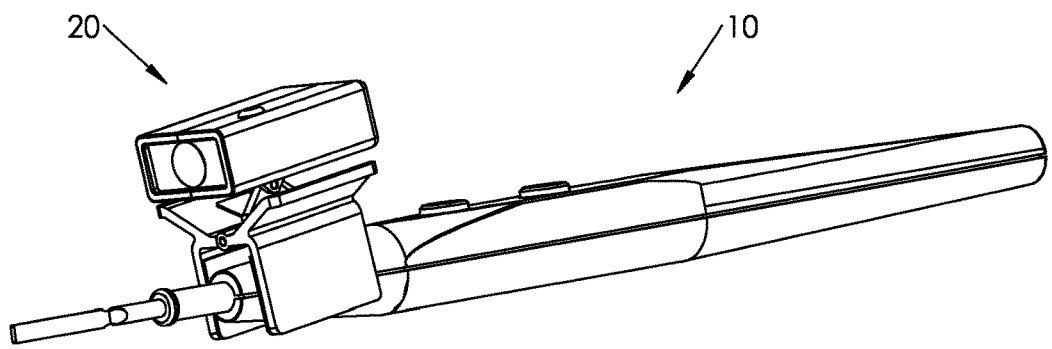
FIGS. 1 through 14 illustrate an embodiment of a lighting device of the subject invention, which includes a clamping mechanism including a pair of spring biased wings adapted for receiving a distal end portion of a handheld electrosurgical instrument.
Figure 2:
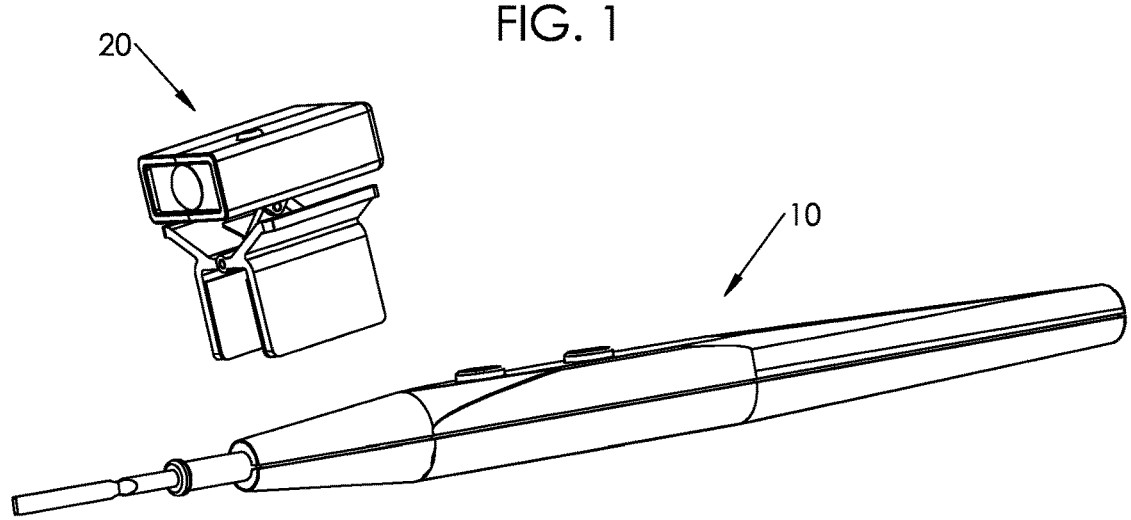

Referring now to the drawings, wherein like reference numerals identify similar structural elements and features of the subject invention, there is illustrated in FIGS. 1 through 14 a lighting device 20 that is adapted and configured for attachment to a handheld electrosurgical instrument 10 to illuminate a surgical site while the instrument is being used by a surgeon during a surgical procedure. Alternatively, the lighting device 20 could be attached to a surgical drape or to body tissue to provide illumination to an adjacent surgical site independent of a surgical instrument.

Figure 7:
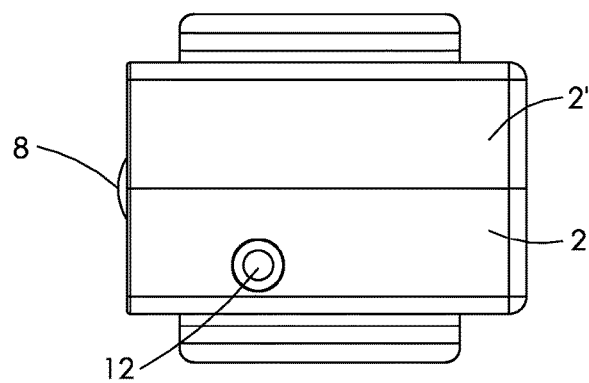
Figure 4A:
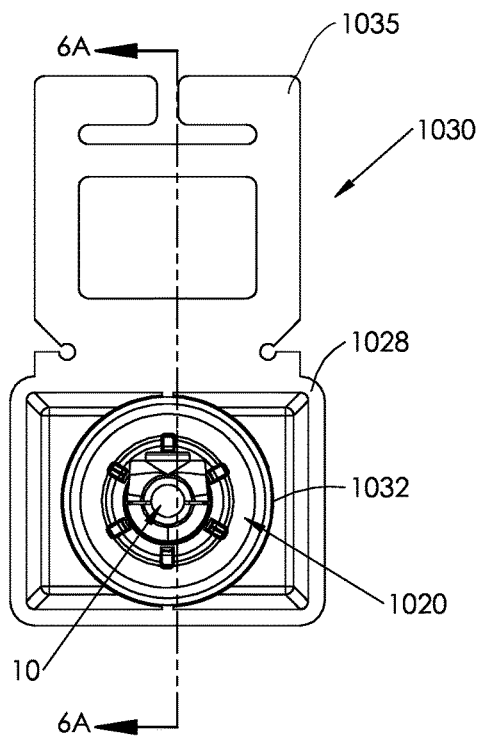
Figure 8:
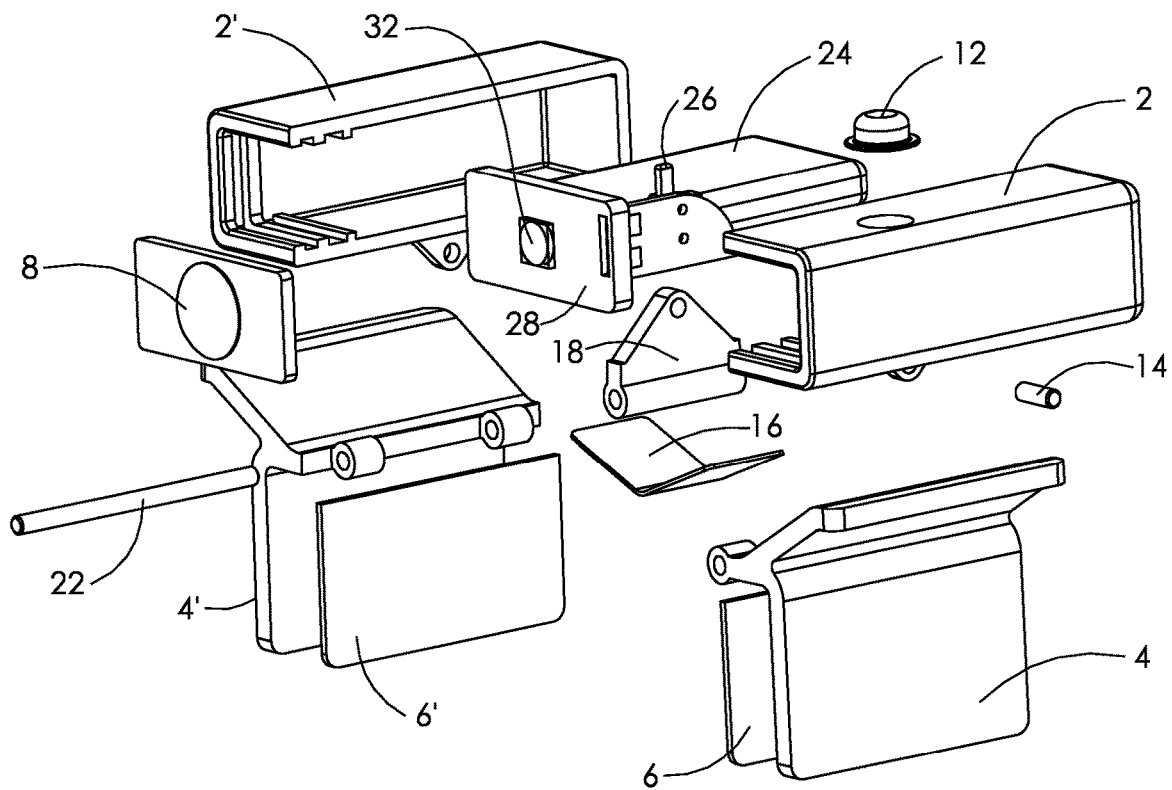

The lighting device 20 includes a lighting sub-assembly 40. As best seen in FIG. 8, the lighting sub-assembly 40 includes an elongated generally rectangular two-part housing 2, 2' defining a longitudinal illumination axis and having an interior chamber. The two-part housing 2, 2' encloses a printed circuit board or PCB 28 having an LED light source 32 supported on a front surface thereof. A switch 26 is supported on a rear surface thereof for controlling the light source 32. A battery cell 24 is associated with the rear surface of the PCB 28 for powering the light source 32, and a lens 8 is positioned in front of the light source 32 for focusing light emanating therefrom. A push button actuator 12 is provided on an upper surface of the housing 2, 2' for manually activating the switch 26, as best seen in FIG. 7.

Figure 14:
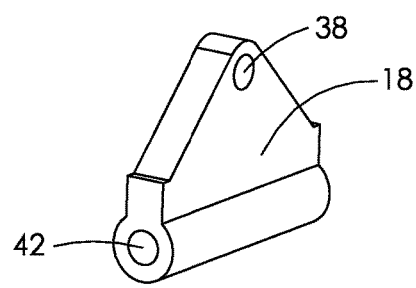
Figure 11A:
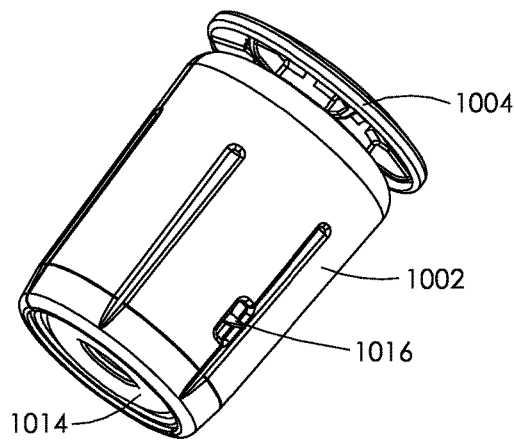
Figure 12A:
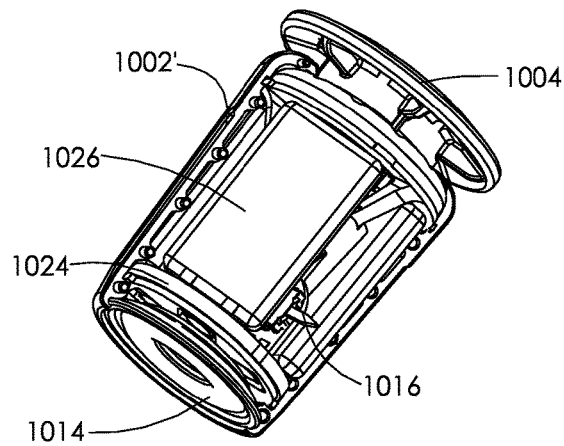
Figure 13A:
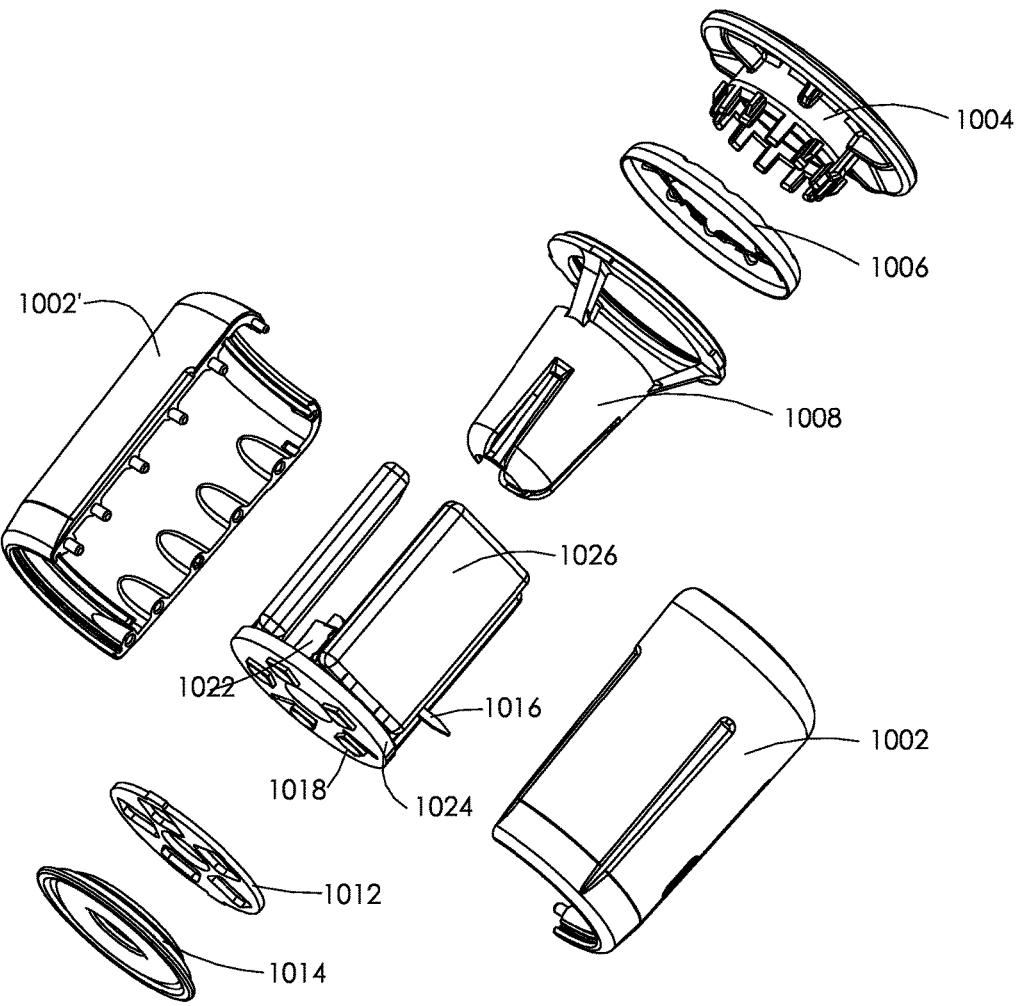
Figure 11B:
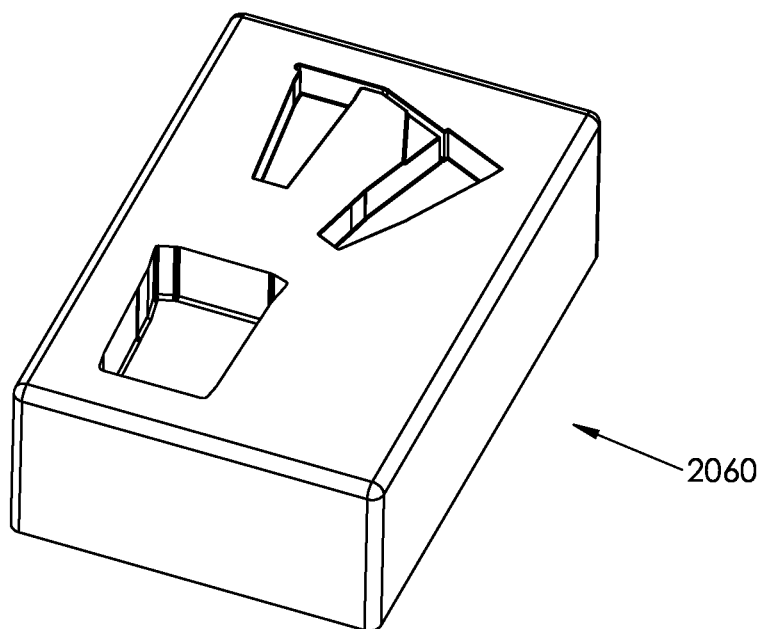
Figure 12B:
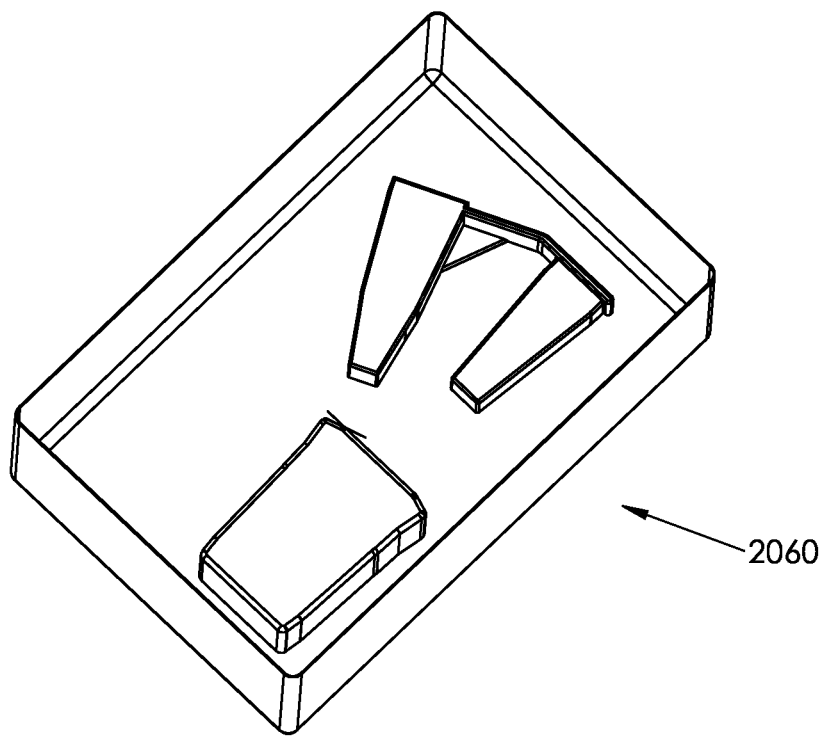
Figure 12C:
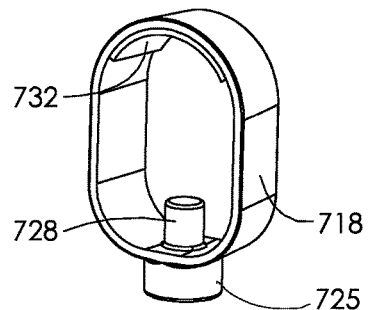
Figure 13C:
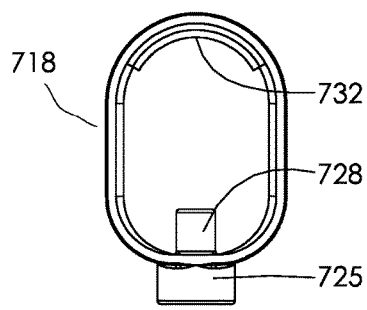
Figure 14C:
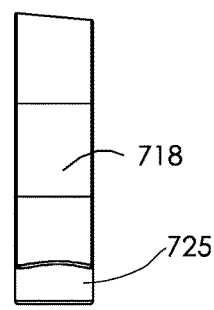
Figure 15C:
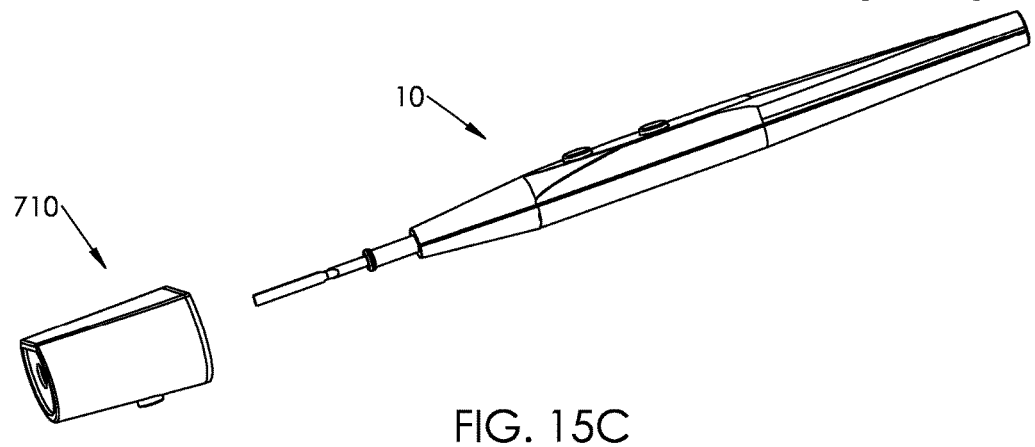
Figure 16C:
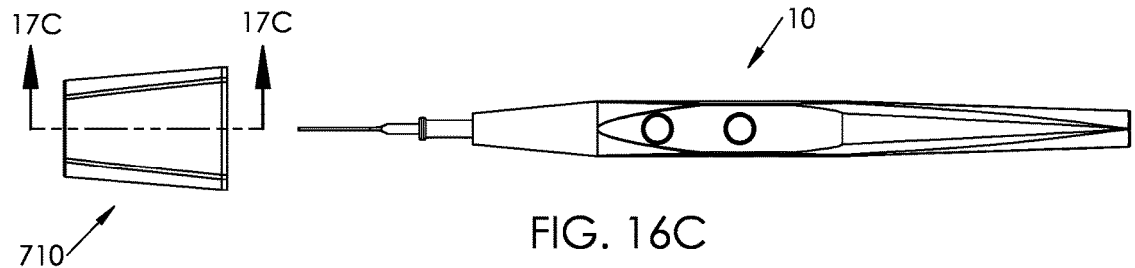
Figure 17C:
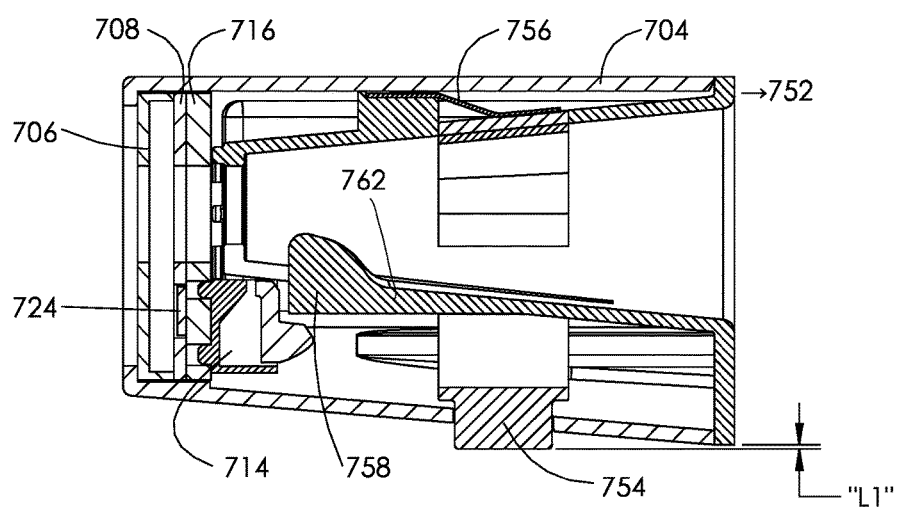
Figure 13B:
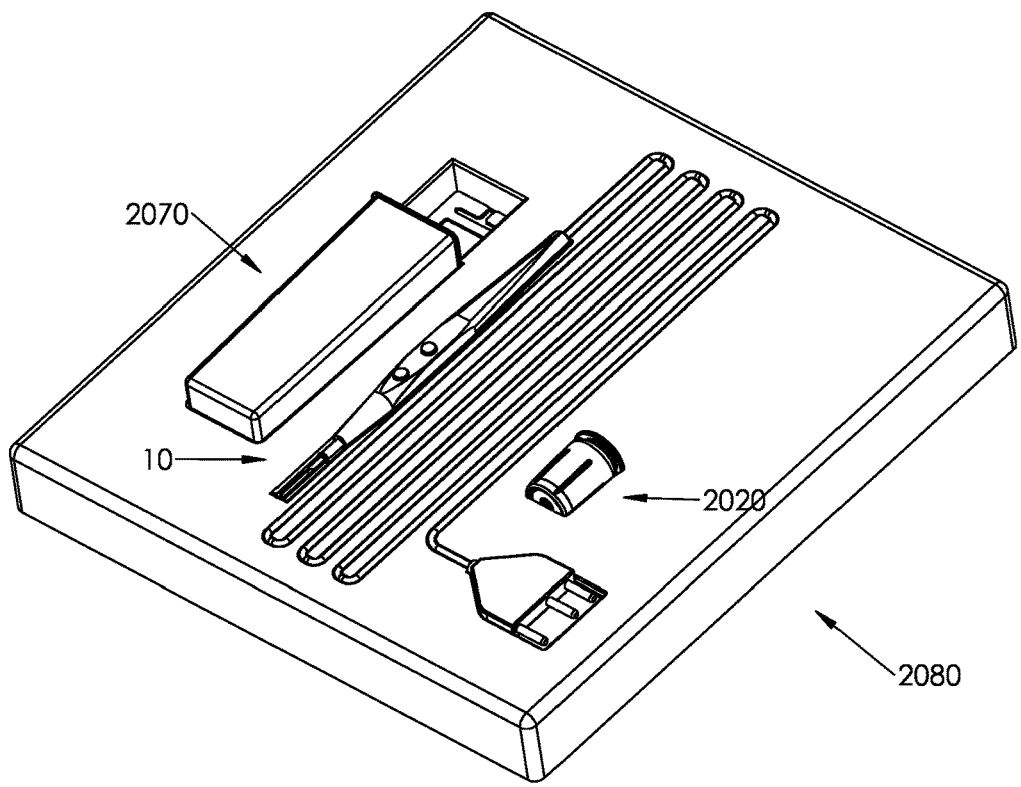
Figure 14B:
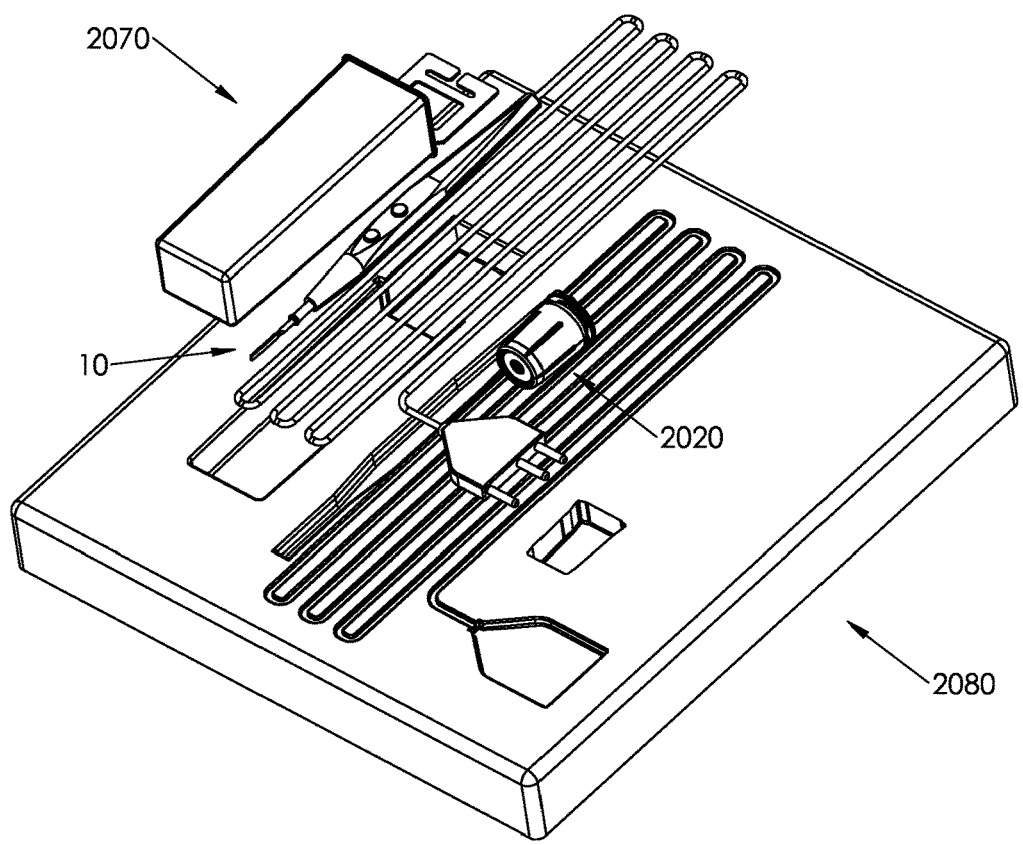
Figure 14A:
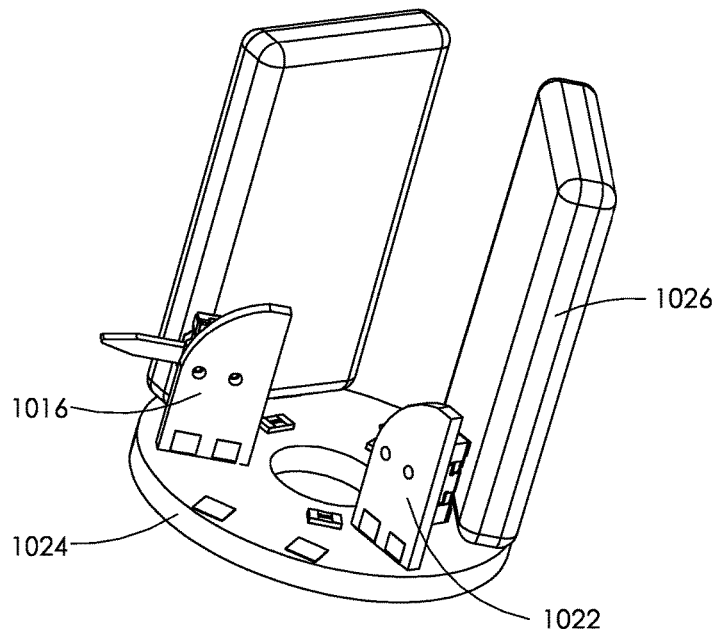
Figure 15A:
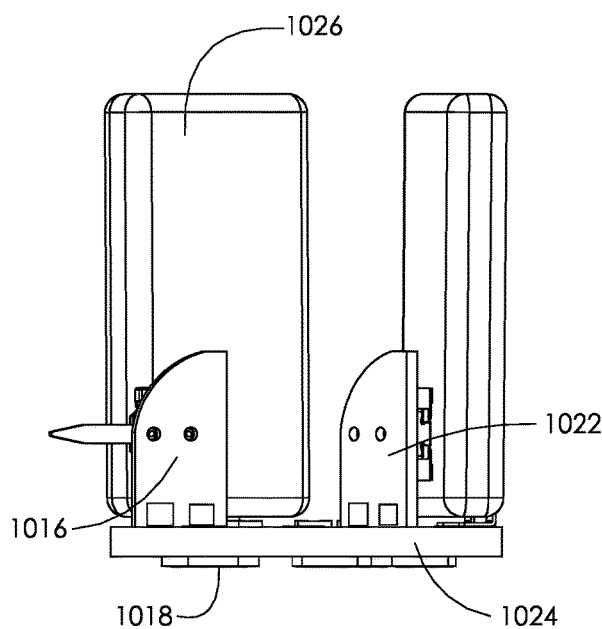
Figure 16A:
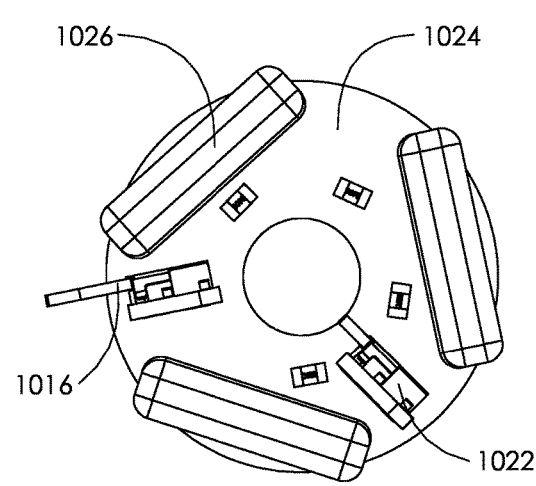
Figure 15:
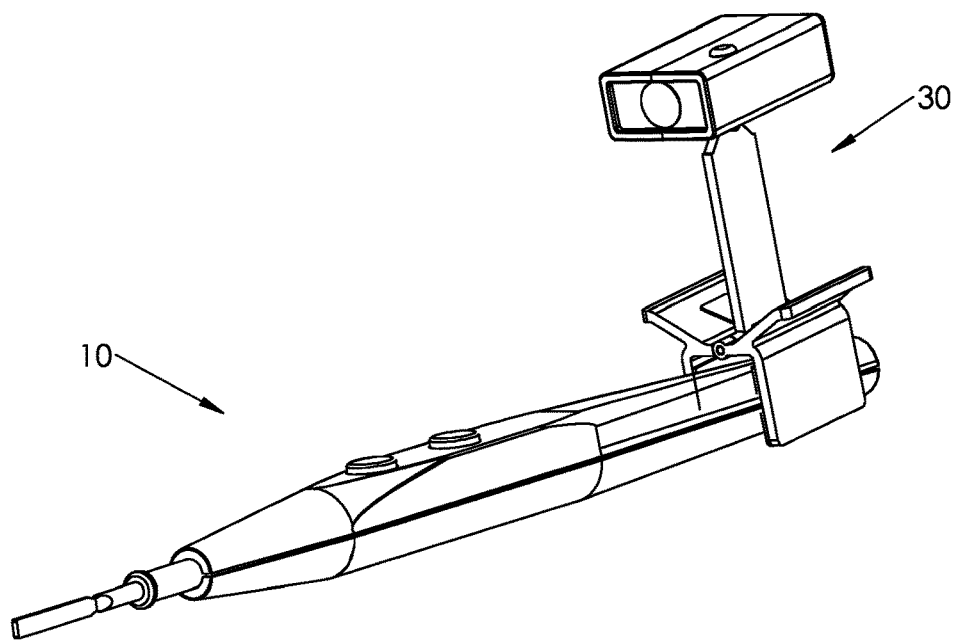
FIGS. 15 through 21 illustrate another embodiment of a lighting device of the subject invention, which includes a clipping assembly for attaching the lighting device to a distal end portion of a handheld surgical instrument, wherein the lighting device is pivotally supported atop a center rib, to avoid interference with the surgeon's hand, and to provide leverage to angle the lighting device so that the light path therefrom intersects the axis of the surgical instrument.
Figure 16:
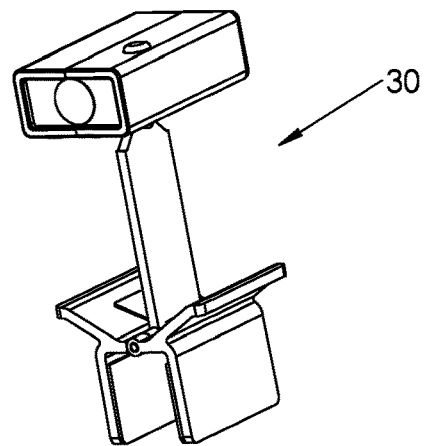
Figure 16:
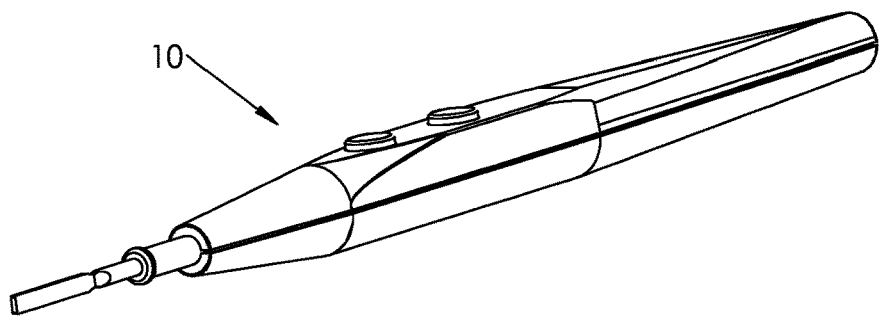
Figure 15B:
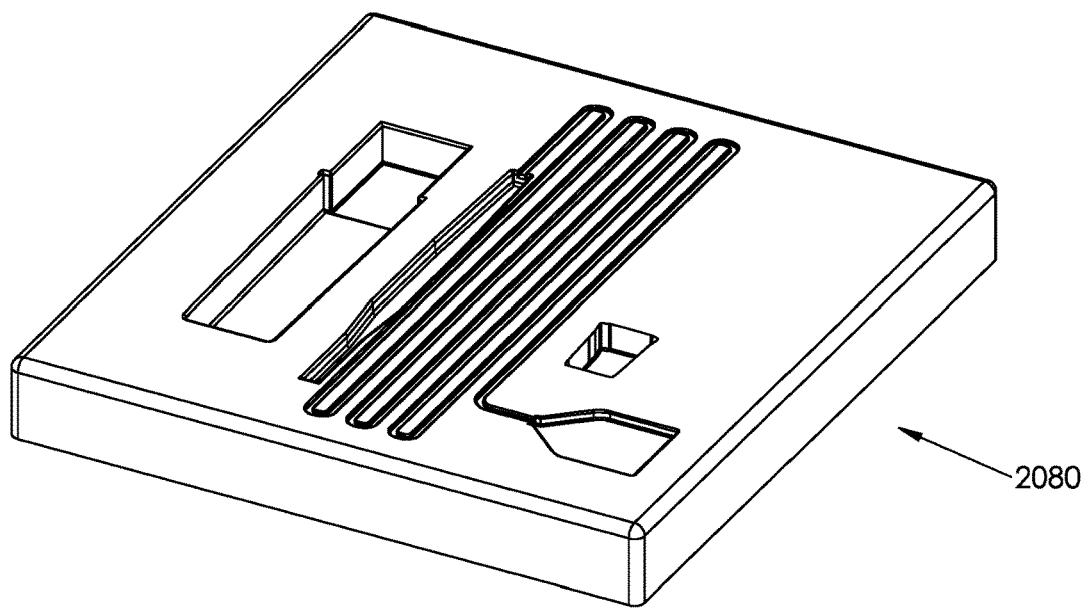
Figure 16B:
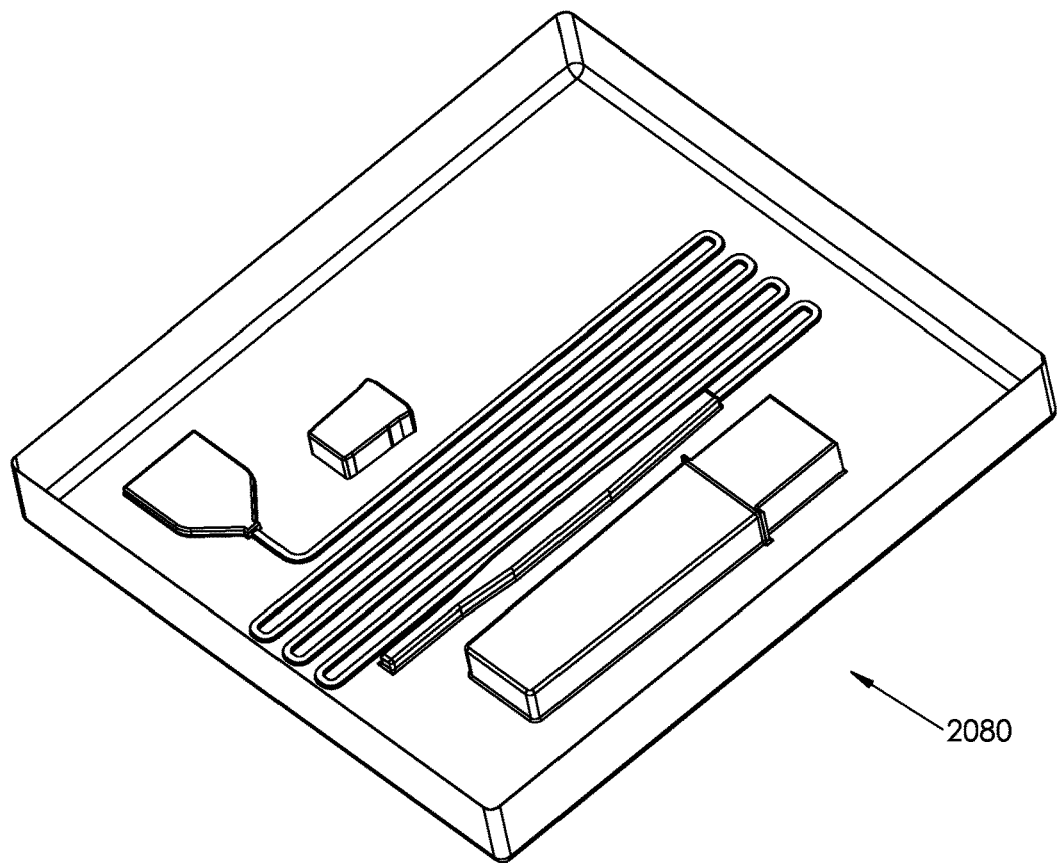
Figure 17:
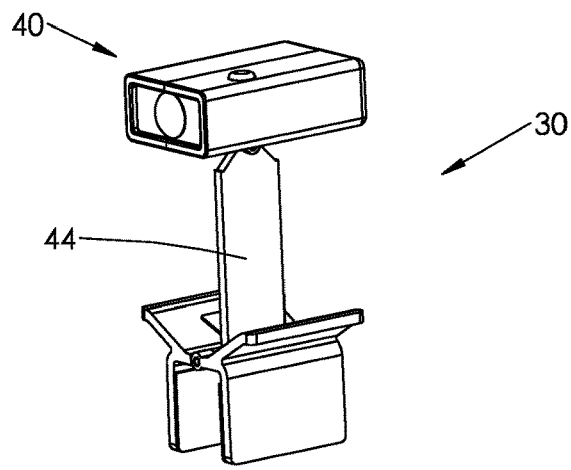
Figure 18:
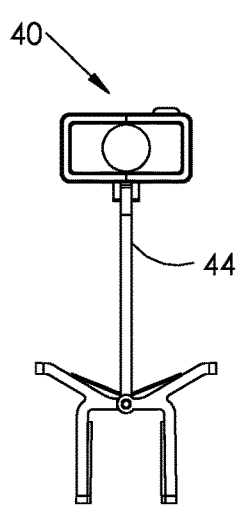
Figure 19:
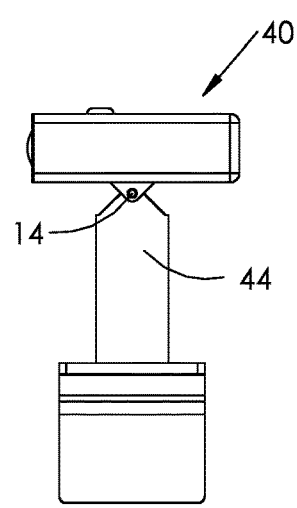
Figure 21:
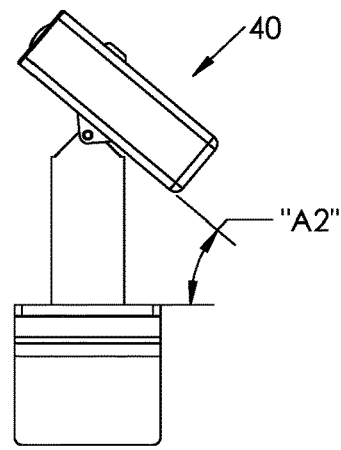
Figure 17B:
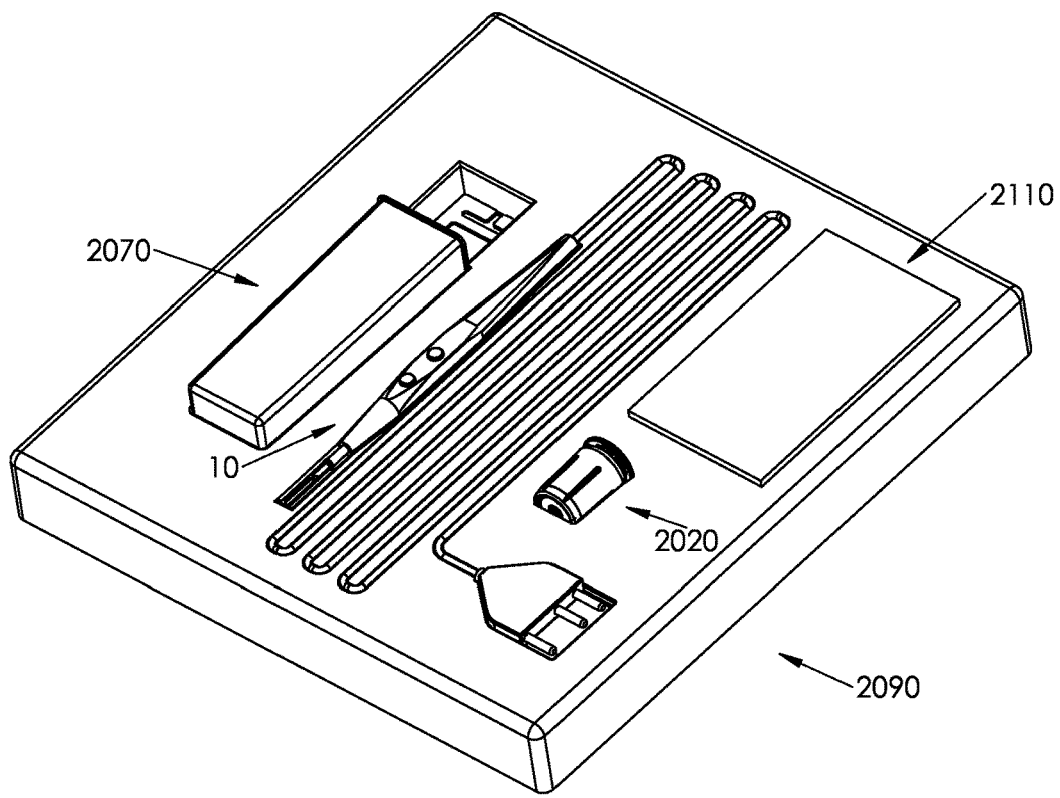
Figure 18B:
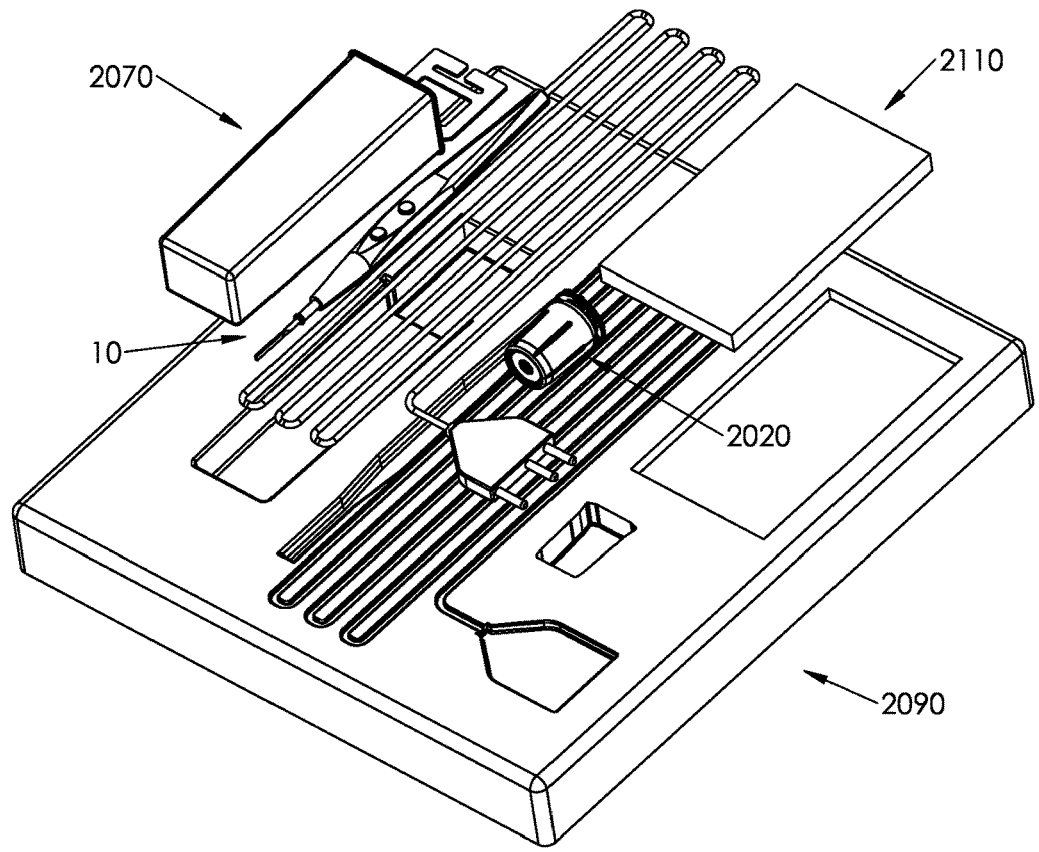
Figure 18C:
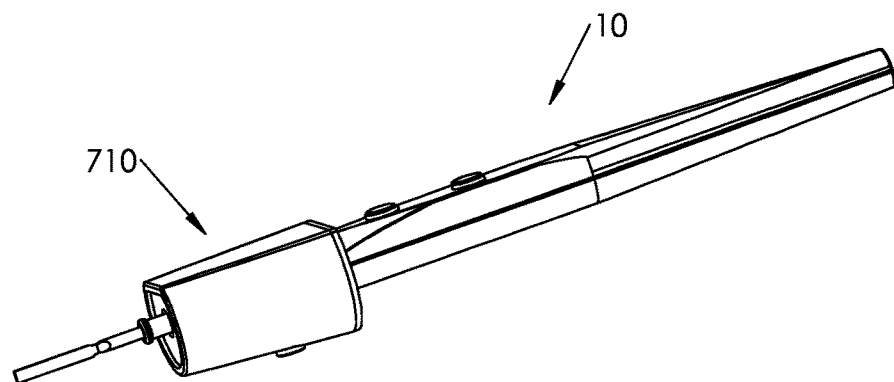
Figure 19C:
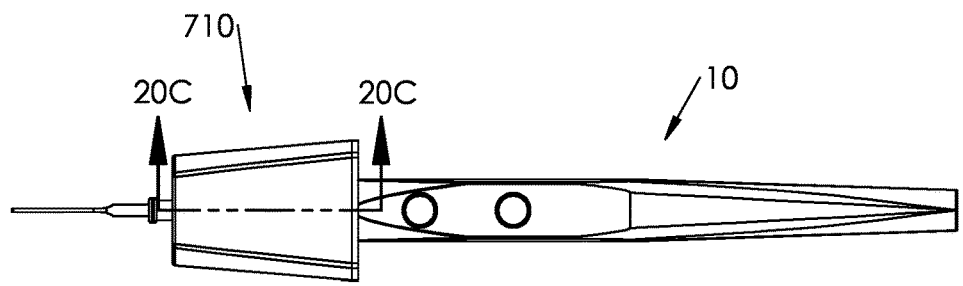

The lighting device 20 further includes an attachment mechanism connected to the lighting sub-assembly 40 by a triangular connector plate or post 18 and associated transverse pivot pin 14 that extends through an aperture 38 in the post 18, as best seen in FIG. 14. The pivot pin 14 allows the lighting sub-assembly 40 to be adjusted relative to the surgical instrument, without having to re-position the attachment mechanism on the lighting device 20. While the attachment mechanism of lighting device 20 is preferably adapted and configured to detachably engage the light sub-assembly 40 to the distal end portion of a surgical instrument 10, as shown for example in FIGS. 1 and 3, it could be readily attached at any location along the length of the surgical instrument, regardless of the shape or geometry of the surgical instrument.

The attachment mechanism includes right and left movable engagement wings 4 and 4' that are pivotably attached to one another, as explained in more detail below. As shown in FIG. 8, right and left compliant or soft rubber holding plates 6, 6' are respectively attached to the opposed inner surfaces of the right and left engagement wings 4, 4' by glue or over molding for gripping the surface of a surgical instrument.

Figure 12:
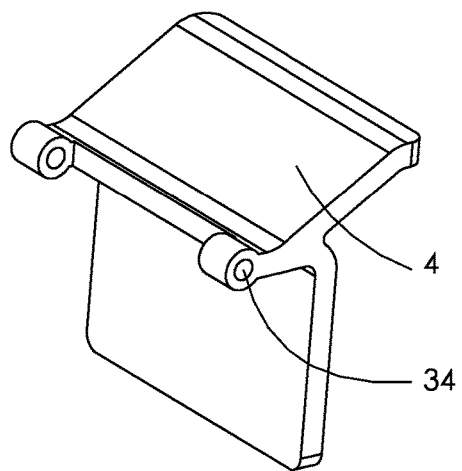
Figure 13:
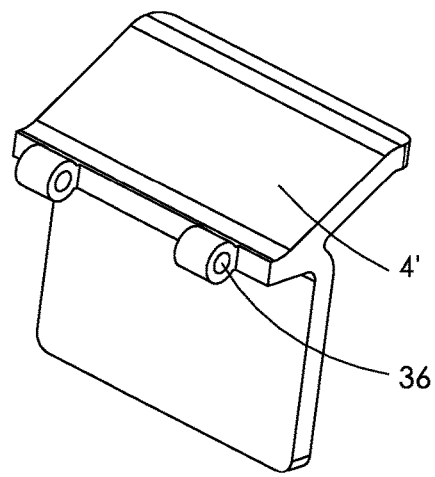

As best seen in FIGS. 12 and 13, the right wing 4 includes a pair of spaced apart reception bores 34, and the left wing 4' includes a pair of spaced apart reception bores 36, while the post 18 includes a single reception bore 42, all of which are adapted and configured to receive an elongated pivot pin 22. The pivot pin 22 enables the two opposed wings to rotate relative to one another and with respect to the post 18.

Figure 3:
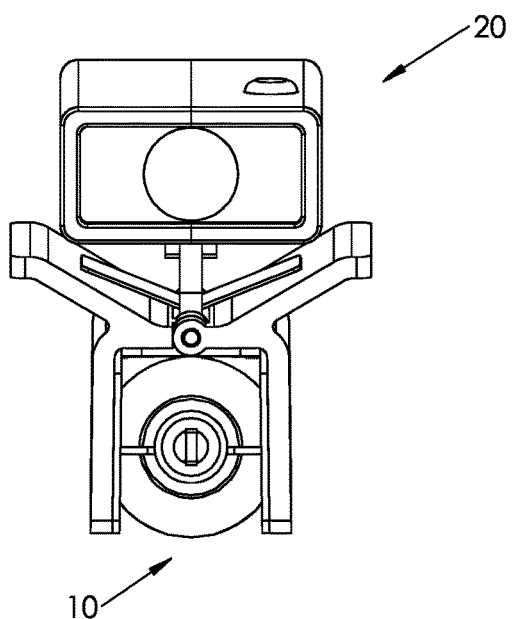
Figure 1B:
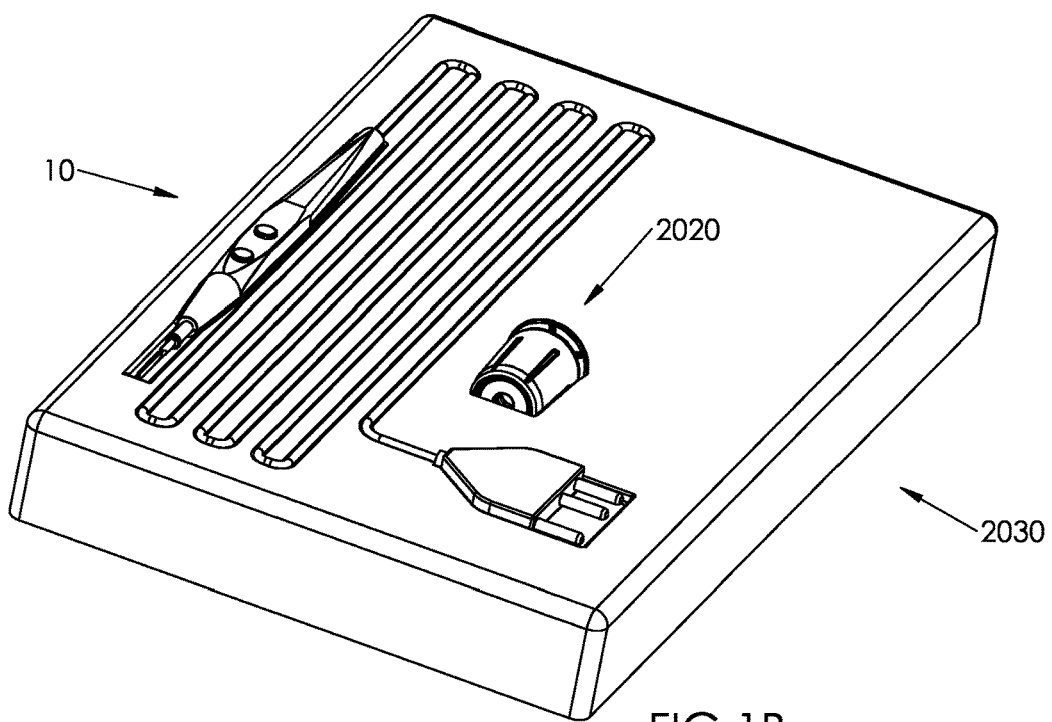
Figure 2B:
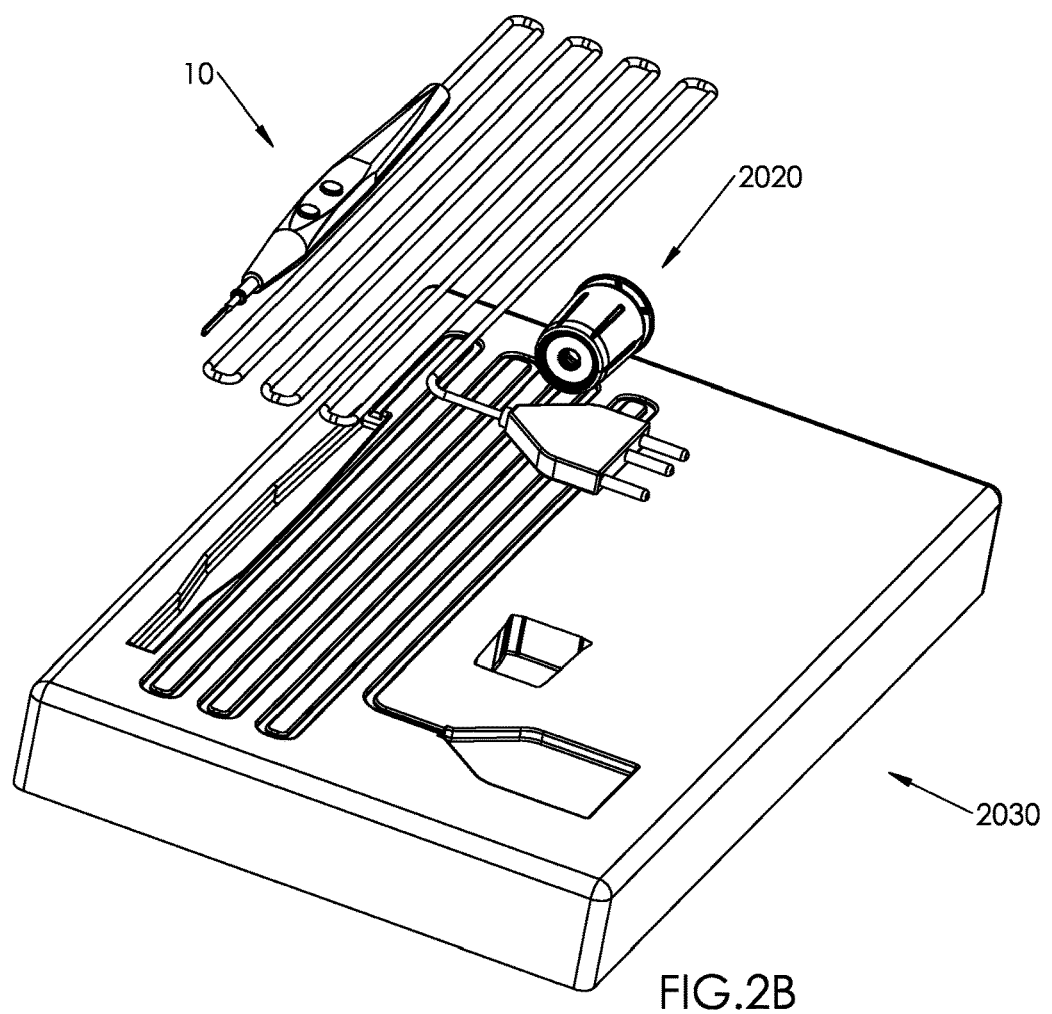
Figure 1C:
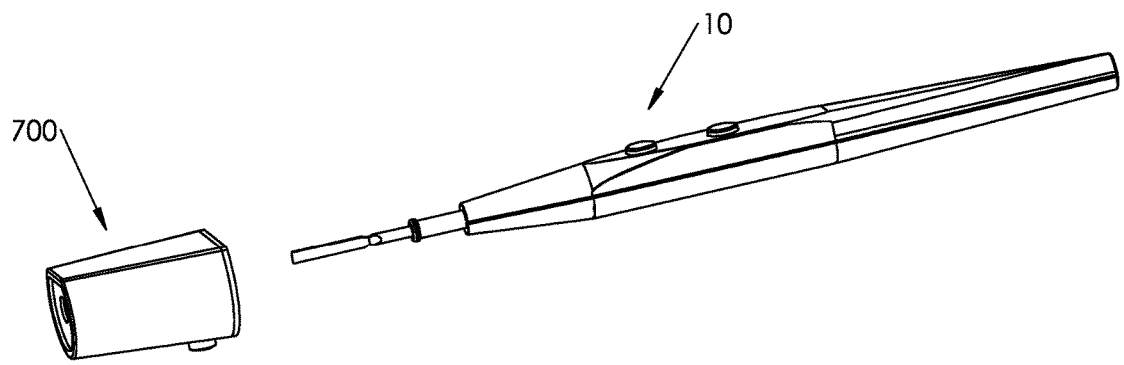
Figure 2C:
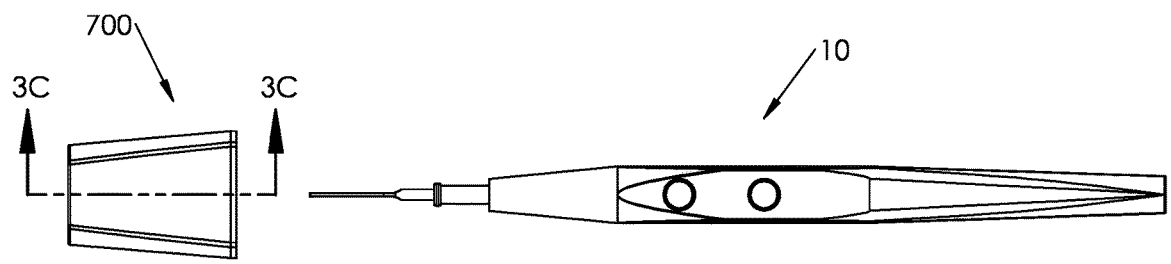
Figure 5:
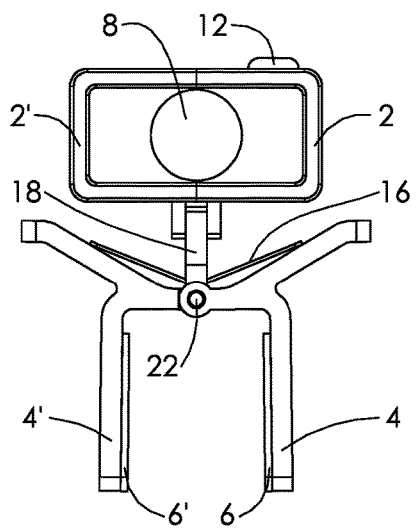
Figure 6:
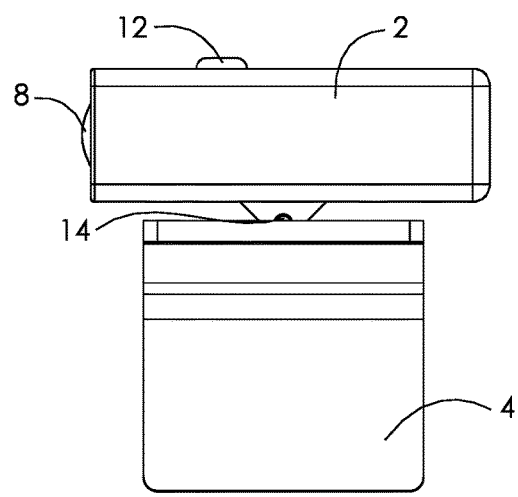
Figure 9A:
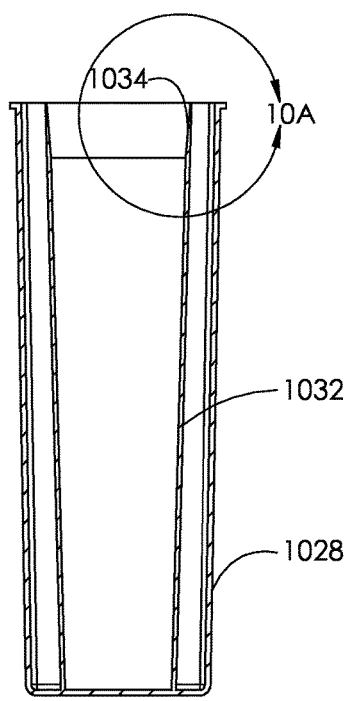
Figure 9:
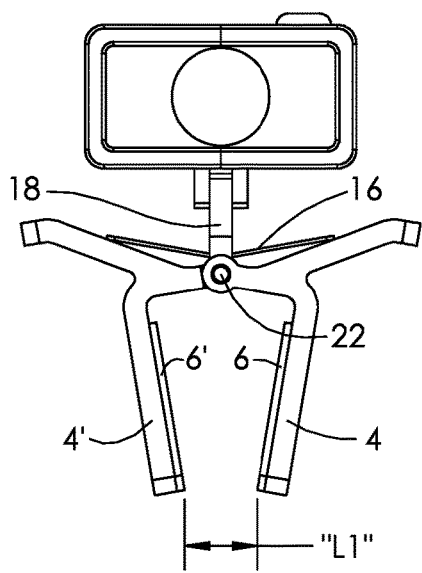
Figure 10:
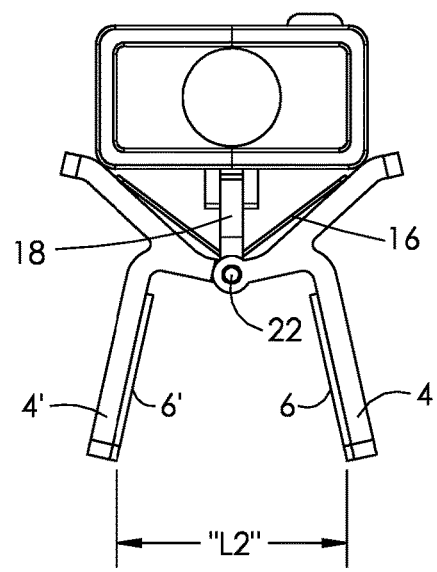
Figure 9B:
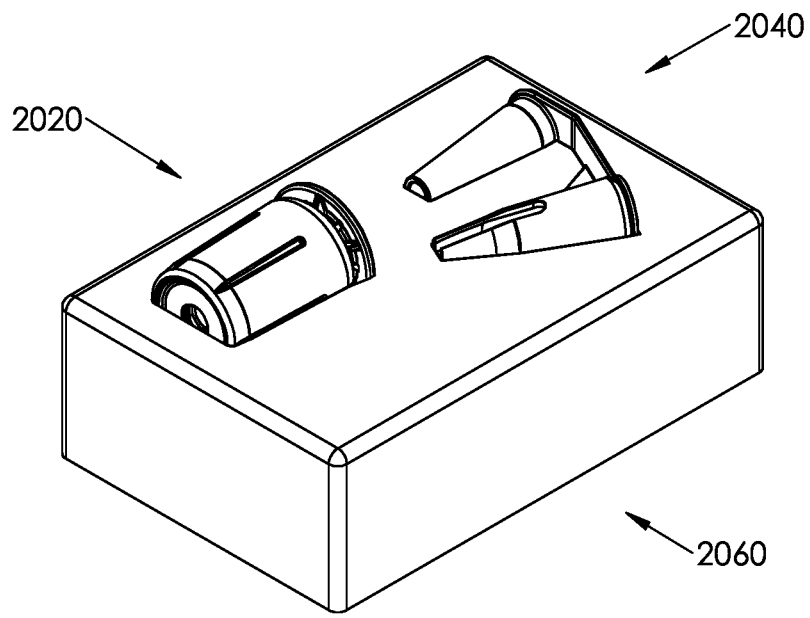
Figure 10B:
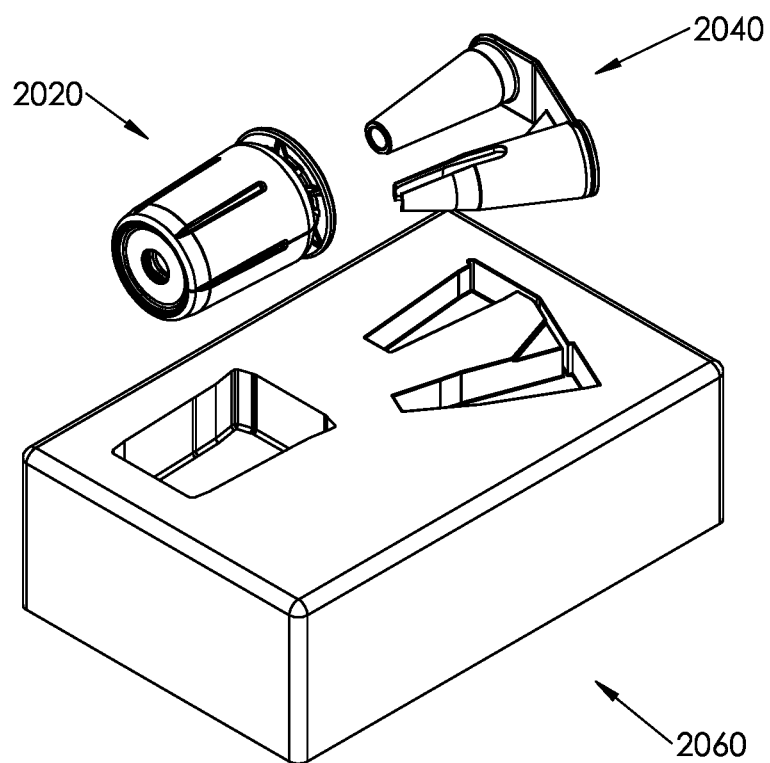
Figure 11:
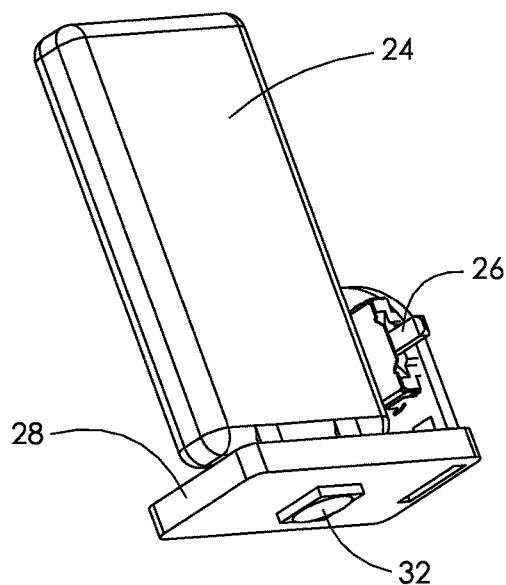

A V-shaped torsion spring 16 is operatively associated with the attachment mechanism for biasing the opposed wings 4, 4' into a normally closed or compressed position shown in FIG. 9. More particularly, the wings 4, 4' are adapted and configured to move between a normally clamped or closed position shown in FIG. 9, wherein the distance between the two opposed wings 4, 4' is L1 and a fully spread or open position shown in FIG. 10, wherein the distance between the two opposed wings 4, 4' is L2. In contrast, the normal gripping position of the attachment mechanism is shown in FIGS. 3 and 5, where the opposed right and left engagement wings 4, 4' are in a partially spread open condition.

Referring now to FIGS. 15 through 21, there is illustrated another embodiment of a lighting device of the subject invention, which is designated generally by reference numeral 30 and it includes a clipping assembly for attaching the lighting device to a distal end portion of a handheld surgical instrument 10, wherein the lighting sub-assembly 40 is pivotally supported atop a tall center post 44 by a transverse pivot pin 14, to avoid interference with the surgeon's hand. Preferably, the center post 44 has a vertical height that is more than twice the vertical height of the housing of the sub-assembly 40, so that if the housing is attached to a proximal end portion of the surgical instrument the vertical height of the post 44 will extend above the hand of a user so that the longitudinal illumination axis of the light housing intersects with the longitudinal axis of the surgical instrument adjacent a distal tip portion thereof.

Furthermore, the lighting device 30 provides the surgeon with the ability to angle the lighting sub-assembly 40 relative to the center post 44 so that the light path therefrom intersects the axis of the surgical instrument 10. The lighting sub-assembly 40 can moved about the pivot pin 14 between a maximum angle A1 shown in FIG. 20 where light is directed away from the surgical site and a minimum angle A2 shown in FIG. 21 where light is directed toward the surgical site.

In an alternative embodiment of the invention which will be discussed in more detail below with reference to FIGS. 73 through 79, the lighting sub-assembly could be rotationally connected to an upper end of the post so as to orient the illumination axis of the light housing with respect to the longitudinal axis of the surgical instrument. For example, a ball and socket joint can rotationally connect the light housing to the post.

Referring to FIGS. 22 through 25, there is illustrated another embodiment of a lighting device of the subject invention which is designated generally by reference numeral 50, and it includes a lighting sub-assembly 40 and a flexible hook and loop type fastening strip 46 for attachment to a handheld surgical instrument 10. More particularly, the sub-assembly 40 includes a pivoting connective plate or post 43 with a slot 45 for accommodating the flexible strip 46.

Figure 26C:
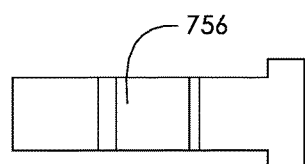
FIGS. 26 and 27 illustrate an embodiment of a lighting device which includes a strip of adhesive for attachment to a handheld surgical instrument.
Figure 27C:
Figure 22:
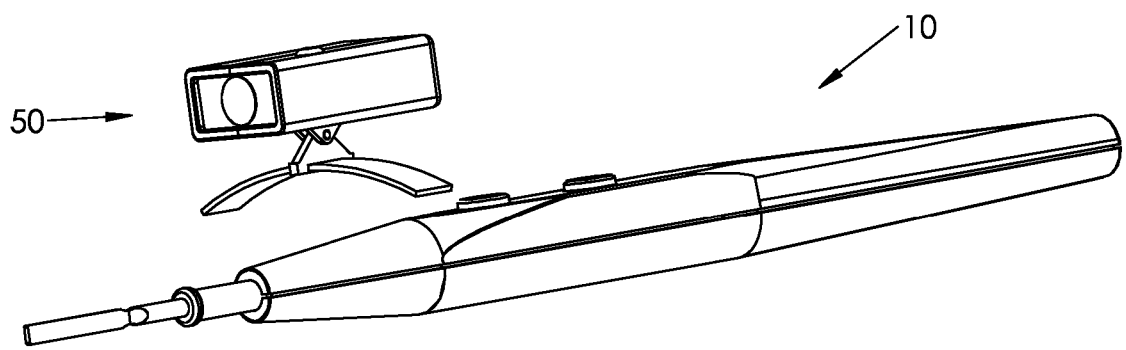
Figure 23:
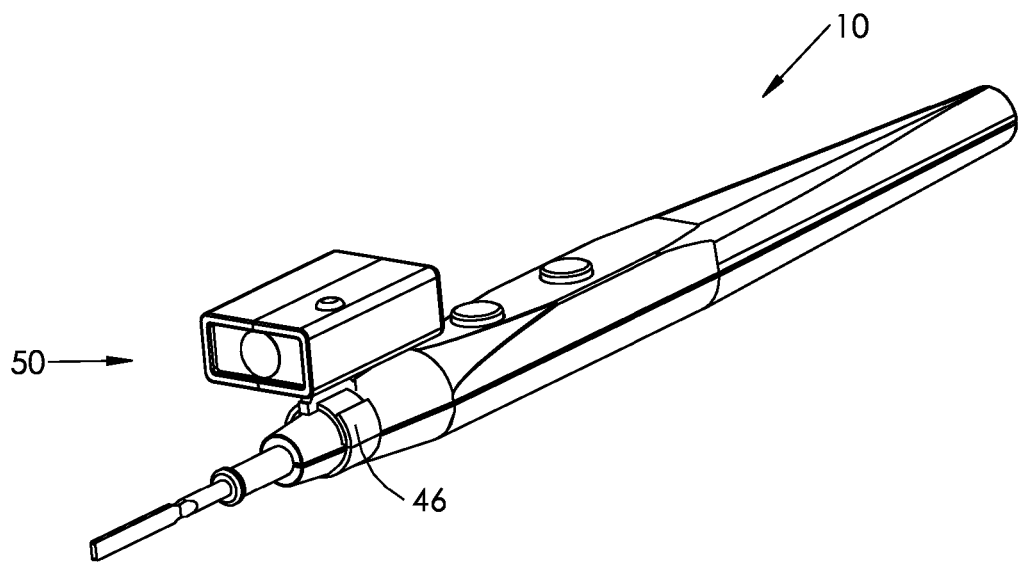
Figure 24:
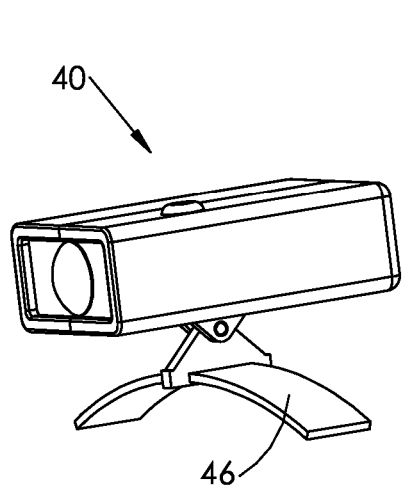
Figure 25:
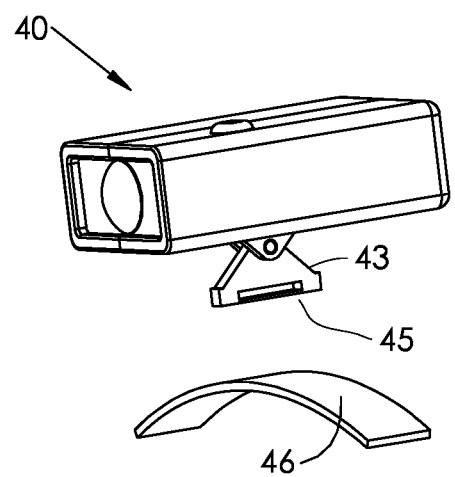
Figure 26:
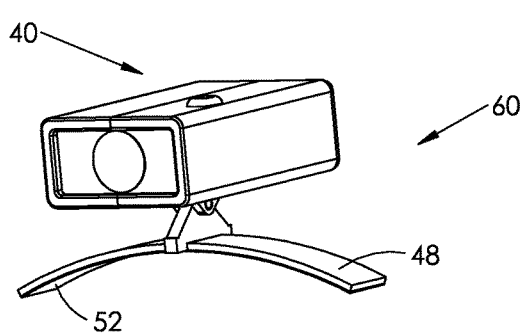
Figure 27:
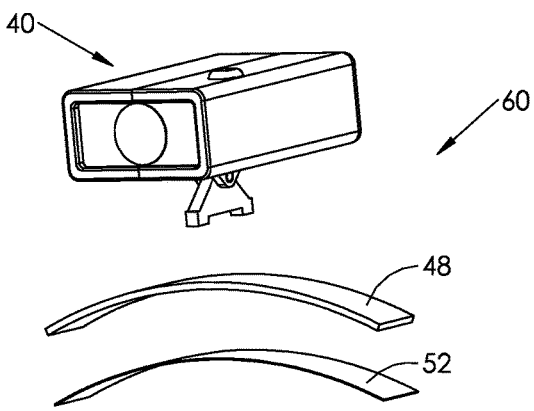
Figure 29:
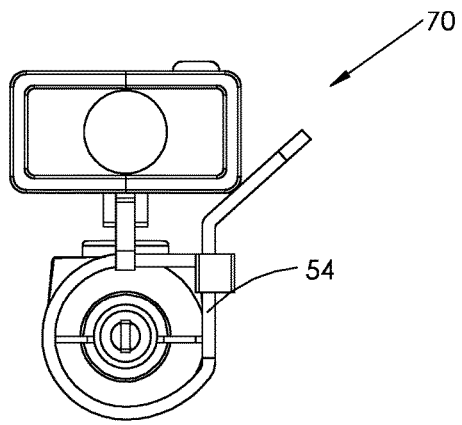

Referring to FIGS. 26 and 27, there is illustrated yet another embodiment of a lighting device of the subject invention which is designated generally by reference numeral 60, and it includes a lighting sub-assembly 40 and a strip of adhesive 48 for attachment to a handheld surgical instrument 10. More particularly, the sub-assembly 40 includes a pivoting connective plate or post 47 with a notch 49 for accommodating the strip of adhesive 48, which is covered by a removable lining 52.

Referring to FIGS. 28 through 36, there is illustrated another embodiment of a lighting device of the subject invention which is designated generally by reference numeral 70, and it includes a lighting sub-assembly 40 and a cable-tie type strip 54 for attachment to a handheld surgical instrument 10. More particularly, the sub-assembly 40 includes a pivoting connective plate or post 56 for supporting the cable-tie strip 54. The cable tie strip 54 has a plurality of teeth 62 that are adapted and configured to interact with a flexible locking tooth 58, as best seen in FIGS. 33 through 36.

Figure 37:
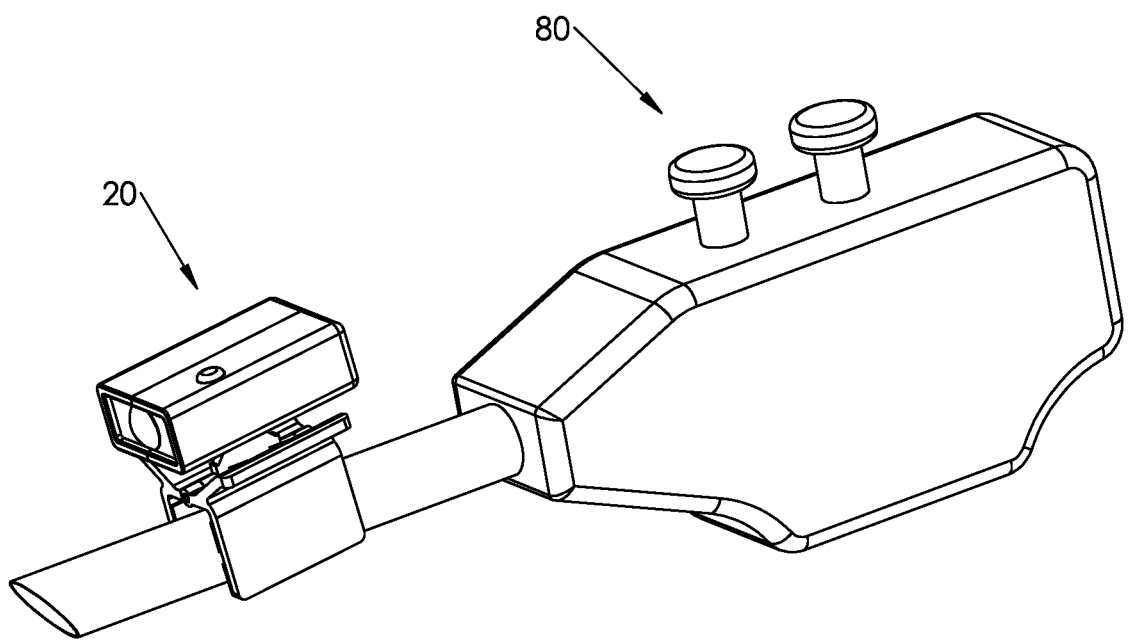
Figure 38:
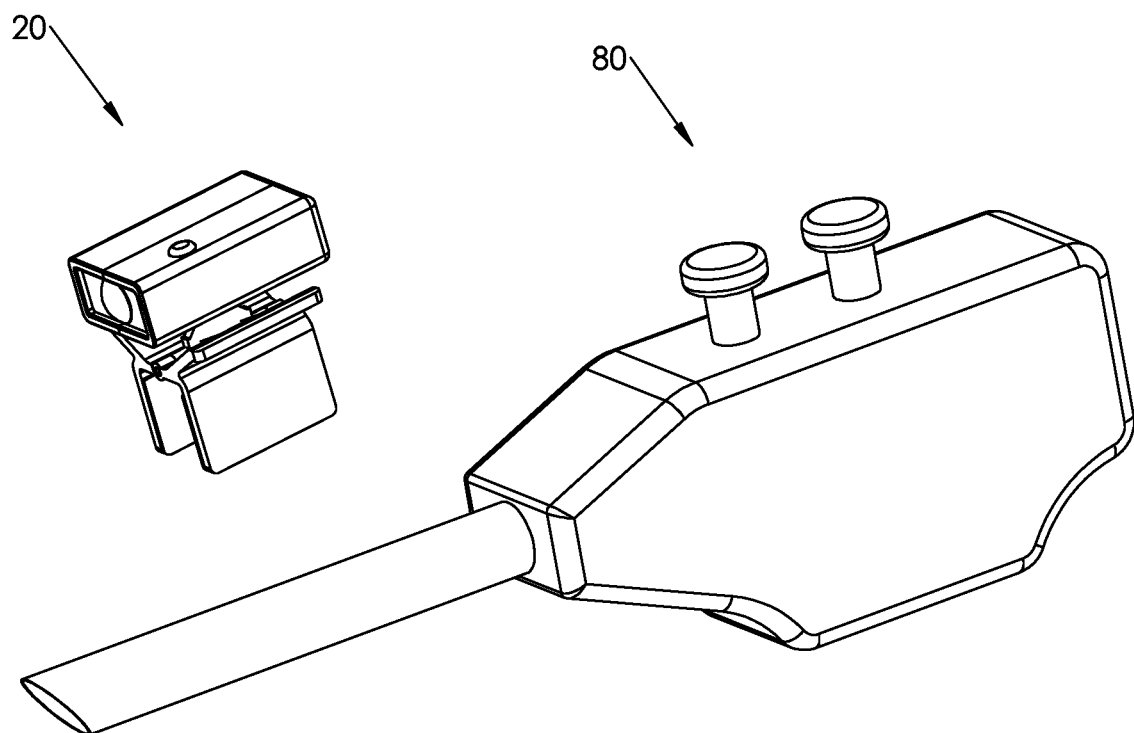
Figure 39:
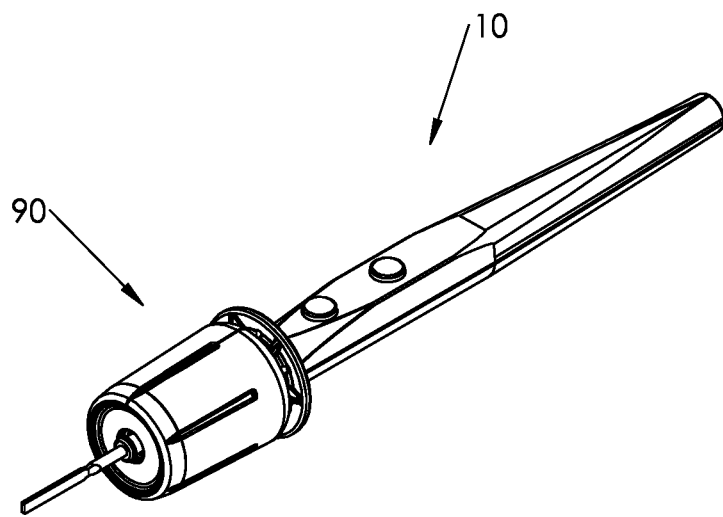
Figure 40:
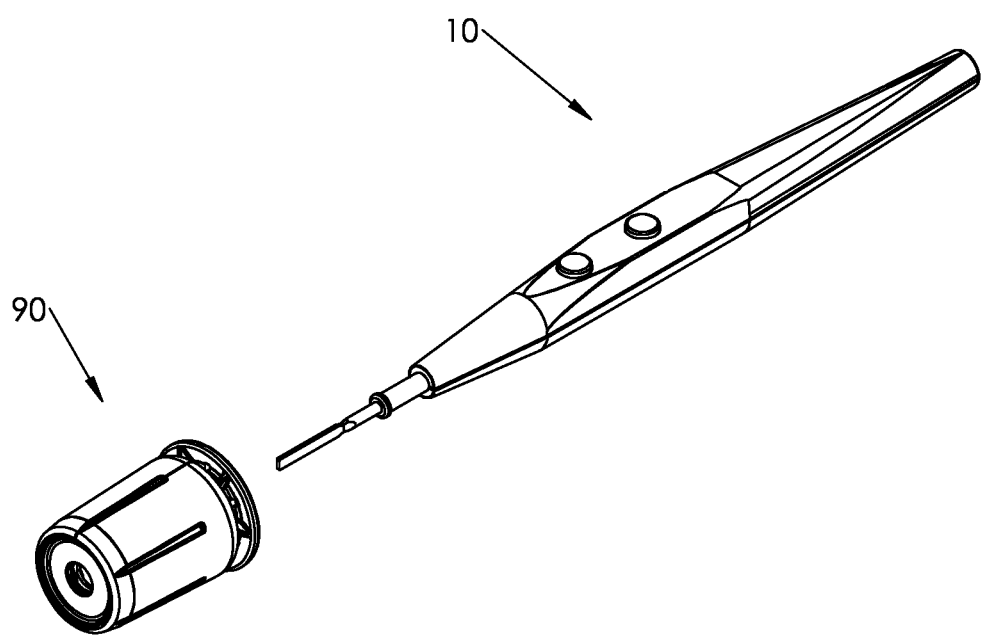
Figure 41:
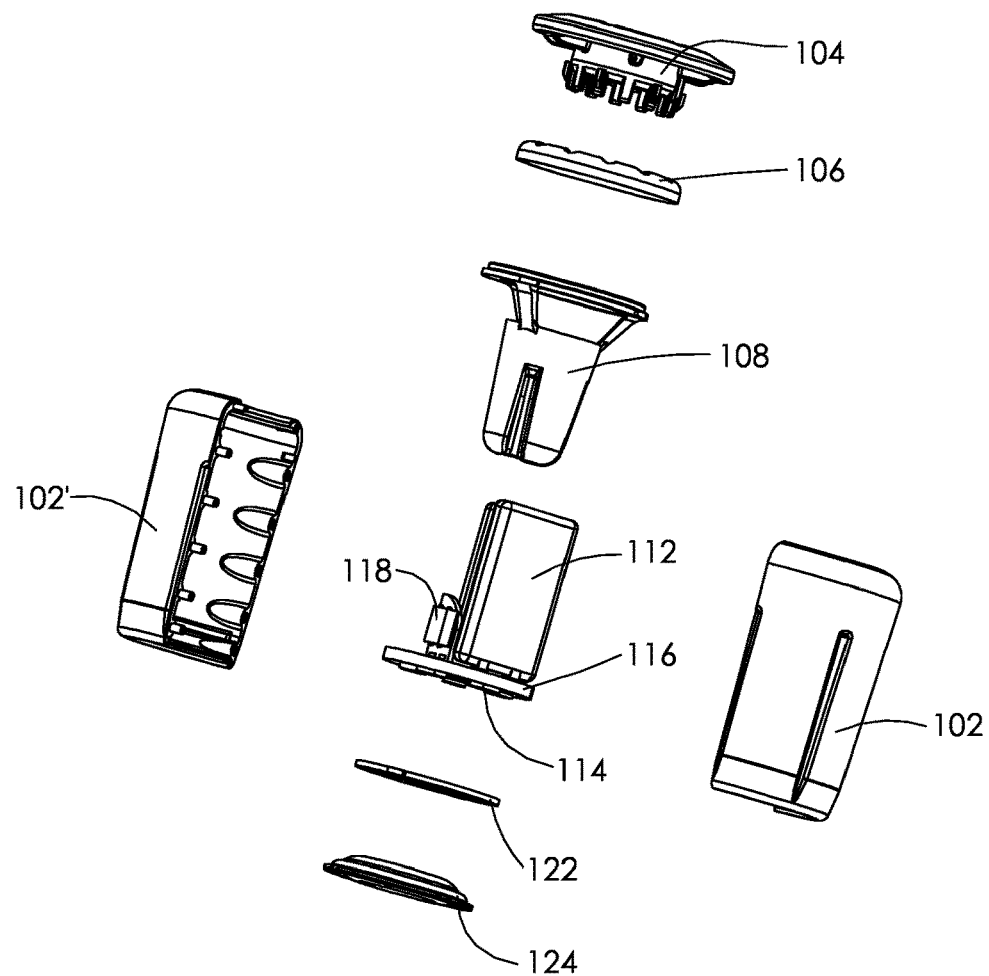
Figure 42:
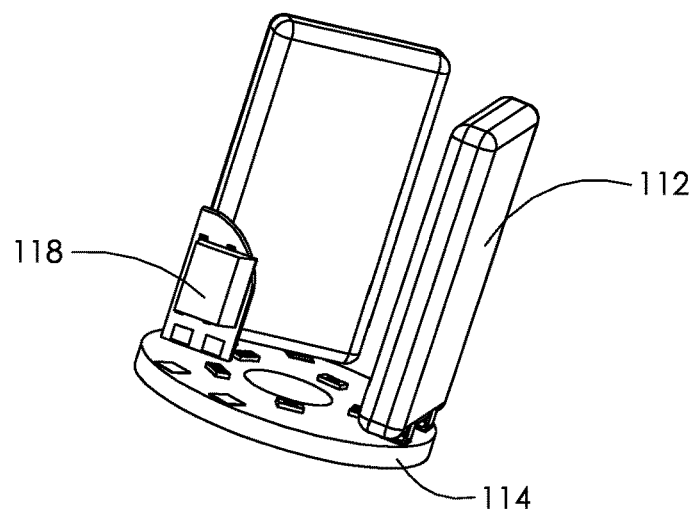
Figure 43:
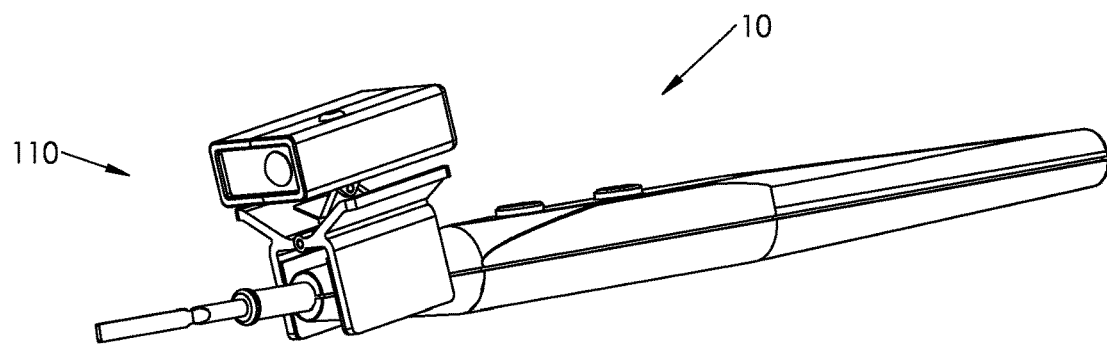
FIG. 43 through 49 illustrate another embodiment of the device of the subject invention, which includes a miniaturized camera and a clamping assembly for attaching the device to a handheld surgical instrument.
Figure 44:
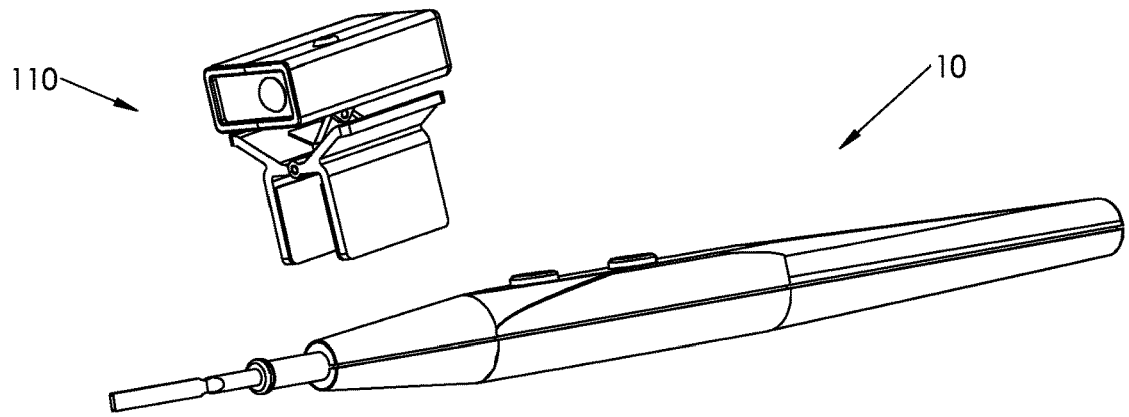
Figures 45, 46:
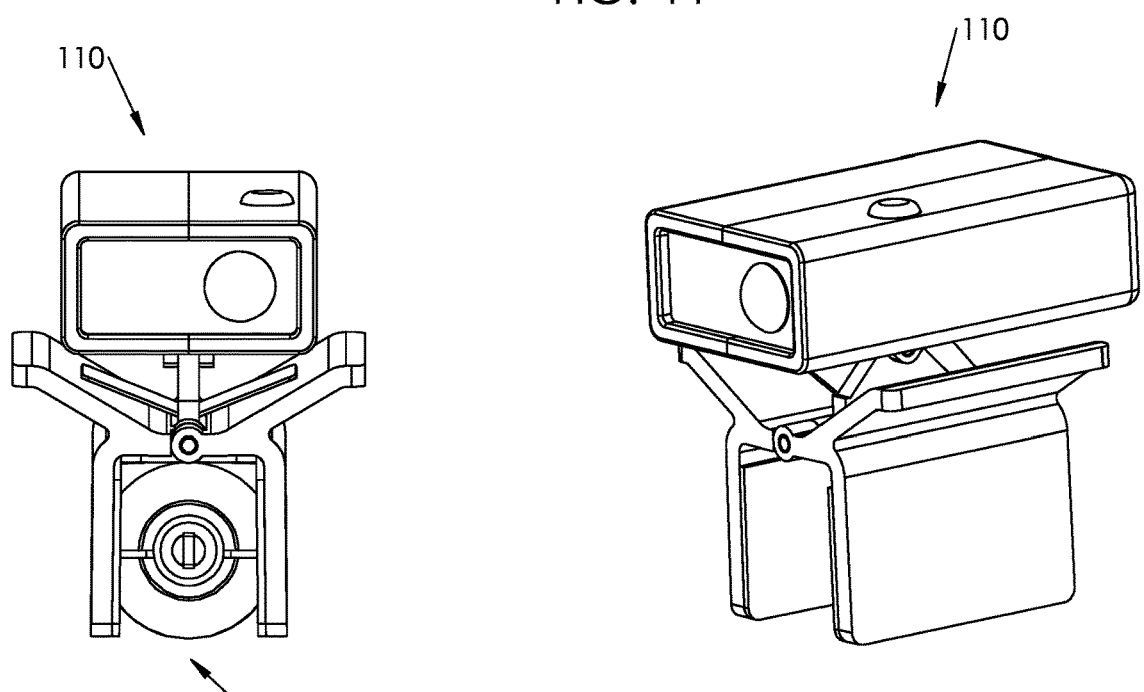
Figure 47:
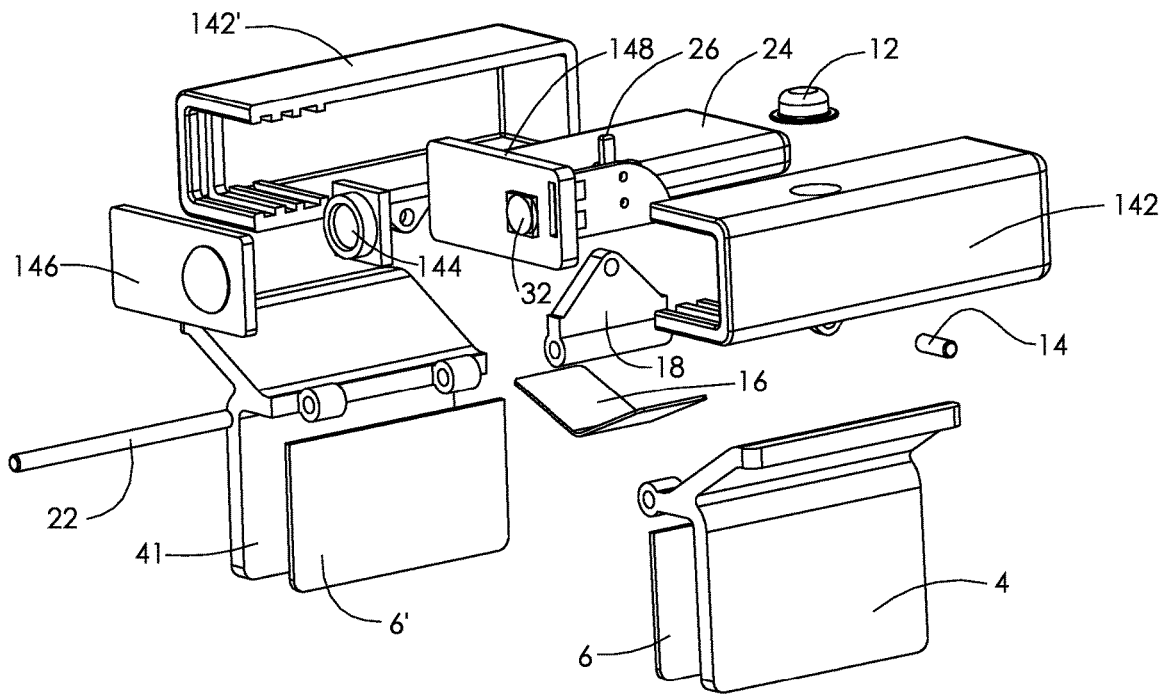
Figure 48:
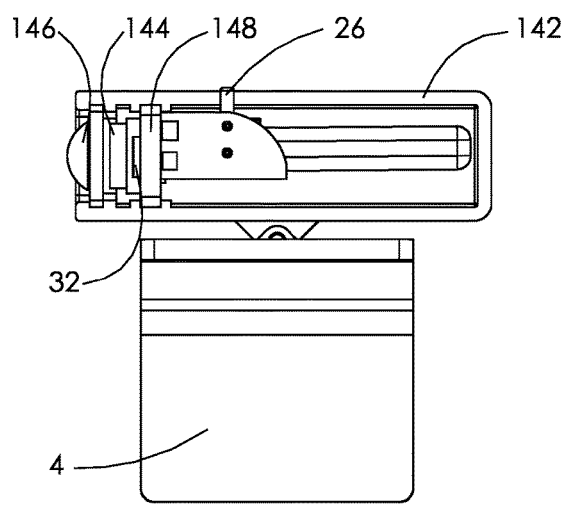
Figure 49:
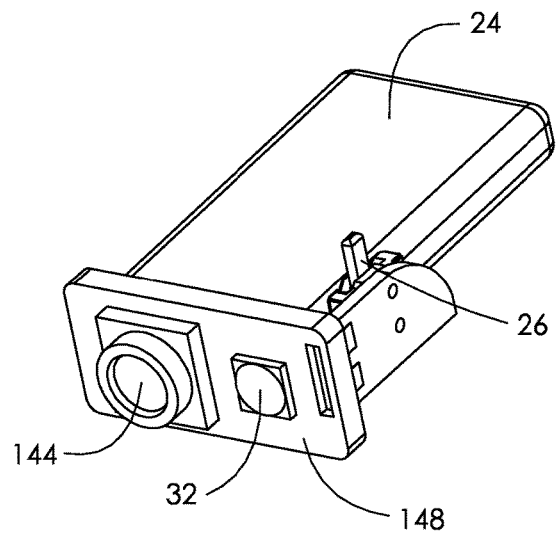
Figure 50:
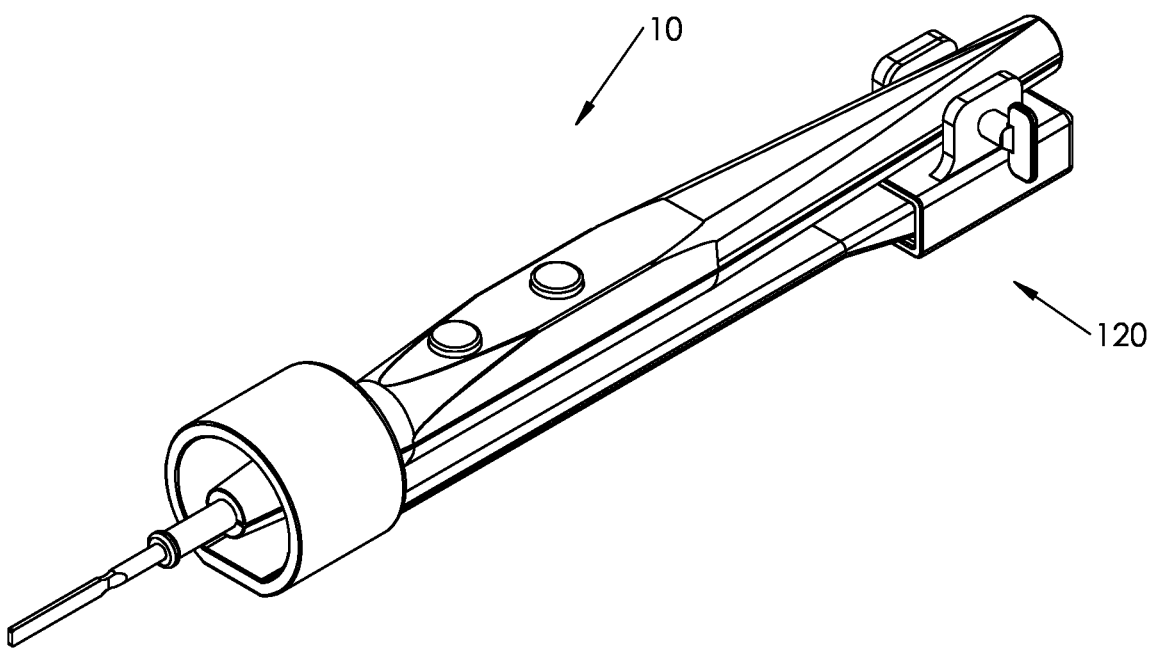
FIGS. 50 through 57 illustrate yet another embodiment of a lighting device for a handheld surgical instrument, which includes a subassembly attachment formed from a polymer material that functions as a waveguide.
Figure 51:
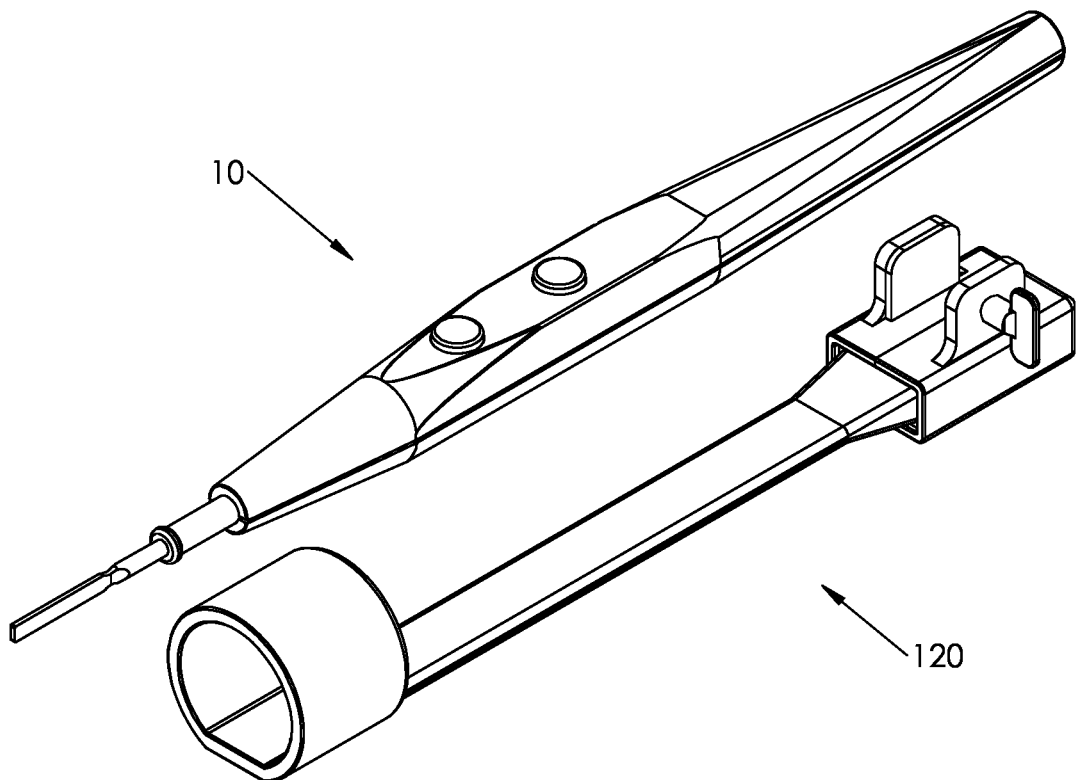
Figure 52:
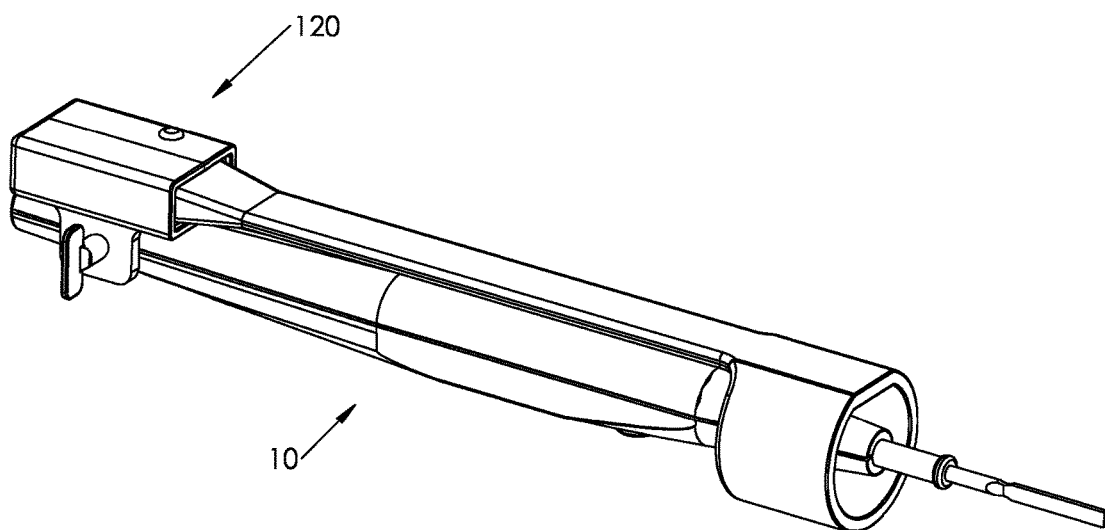
Figure 53:
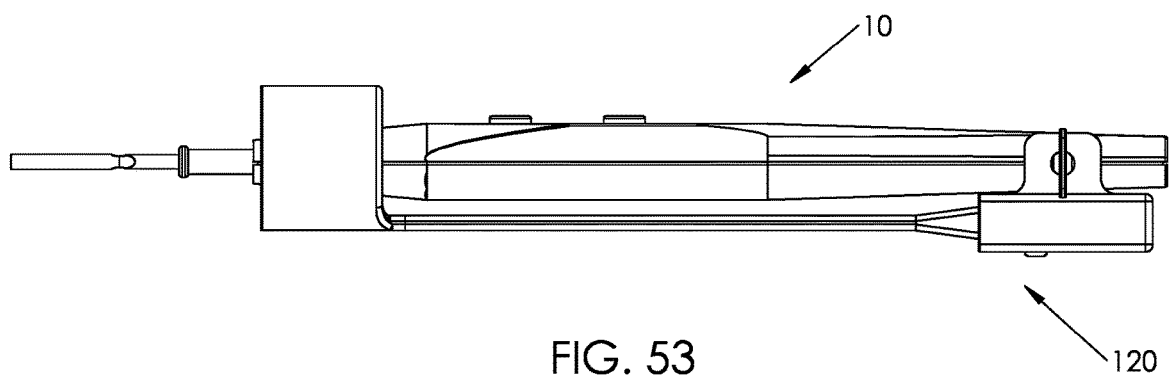

Referring now to FIGS. 37 and 38, there is illustrated the lighting device 20 of the subject invention, which was described in detail above with reference to FIGS. 1 through 14, but here it is shown in conjunction with a suction/irrigation instrument 80 rather than a handheld electrosurgical instrument 10. Thus, those skilled in the art should readily appreciate that the lighting devices of the subject invention can be utilized with a variety of different surgical instruments, including without limitation electrosurgical instruments and suction/irrigation devices.

Referring now to FIGS. 39 through 42, there is illustrated another embodiment of the lighting device of the subject invention that is designated generally by reference numeral 90 and is adapted and configured to receive the distal end portion of a handheld surgical instrument 10. The lighting device 90 has a generally cylindrical two-part housing 102, 102' with a proximal end cap 104 and ring 106 having teeth for mechanically engaging the distal end portion of the surgical instrument 10. An inner body portion 108 is located within the housing 102, 102' for receiving and accommodating the distal end portion of the surgical instrument 10.

A PCB 116 is located within the distal end portion of the housing 102, 102' and it has a plurality of LED light sources 114 on a front surface thereof for illuminating a surgical site. A plurality of battery cells 112 are connectively supported on a rear surface of the PCB for powering the LED light sources 114. A lens 124 is located in front of the LED light sources 114 and a spacer 122 is positioned between the lens and the PCB 116 to provided clearance for the light sources 114. A non-contact switching mechanism 118 is operatively associated with the rear surface of the PCB 116 for activating the LED light sources 114.

The non-contact switching mechanism 118 would be selected from the group of switching mechanisms consisting of a Hall-effect sensor, a proximity sensor and a photosensor. A Hall effect sensor is a transducer that varies its output voltage in response to a magnetic field. Hall-effect sensors are used for proximity switching, positioning, speed detection, and current sensing applications. In a Hall effect sensor, a thin strip of metal has a current applied along it. A proximity sensor often emits an electromagnetic field or a beam of electromagnetic radiation (infrared, for instance), and looks for changes in the field or return signal. The object being sensed is often referred to as the proximity sensor's target. Different proximity sensor targets demand different sensors.

Referring now to FIGS. 43 through 49, there is illustrated yet another embodiment of the lighting device of the subject invention that is designated generally by reference numeral 110 and is adapted and configured for attachment to the distal end portion of a handheld surgical instrument 10. The lighting device 110 is substantially similar to the lighting device 20 described above with reference to FIGS. 1 through 14, except that the lighting device 110 includes a miniaturized camera 144 in addition to an LED lighting device 32, to provided real time imaging of the operative site. More particularly, the lighting device 110 includes a generally rectangular two-part housing 142, 142' that contains a rectangular PCB 124 supporting the LED light source 32 on a front surface thereof, but it is located off-center to accommodate the camera 144. Similarly, the lighting device 110 includes a lens plate 146 with a lens surface that is located off-center to accommodate the position of the LED light source 32 on PCB 148.

Referring now to FIGS. 50 through 57, there is illustrated yet another embodiment of a lighting device that is designated generally by reference numeral 120 and is adapted and configured for use in conjunction with a handheld surgical instrument 10. The lighting device 120 includes a lighting sub-assembly having a generally rectangular two-part housing 202, 202' that encloses a rectangular PCB 214 having a pair of LED light sources 216 on a front surface thereof and having a switch 218 and a battery cell 222 associated with a rear surface thereof. The switch 218 is activated by a push button 212 associated with housing portion 202.

Figure 54:
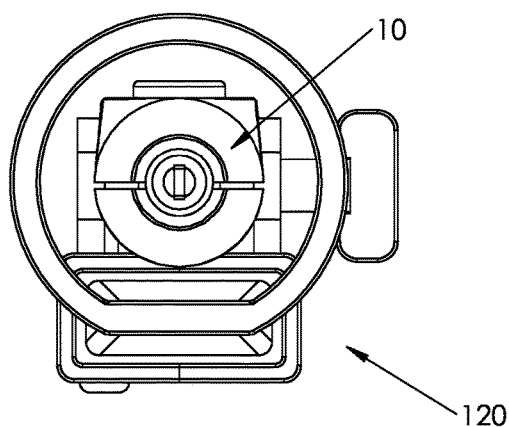
Figure 55:
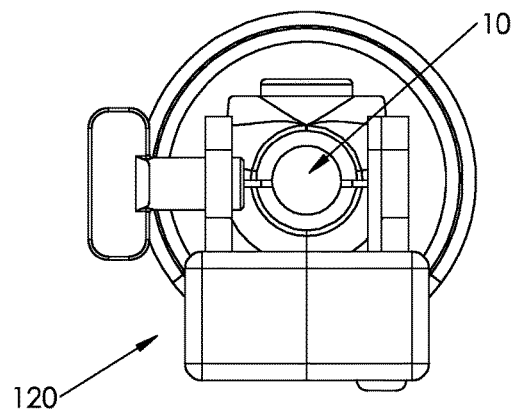
Figure 56:
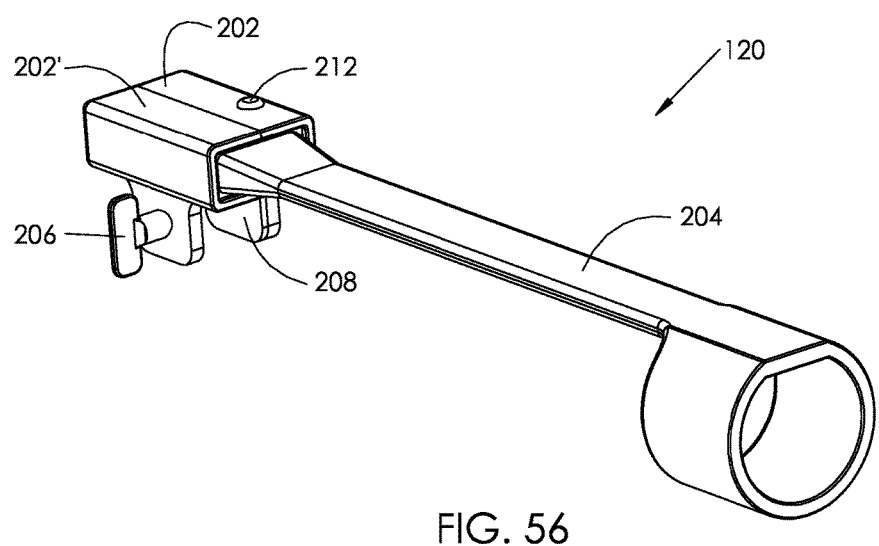
Figure 57:
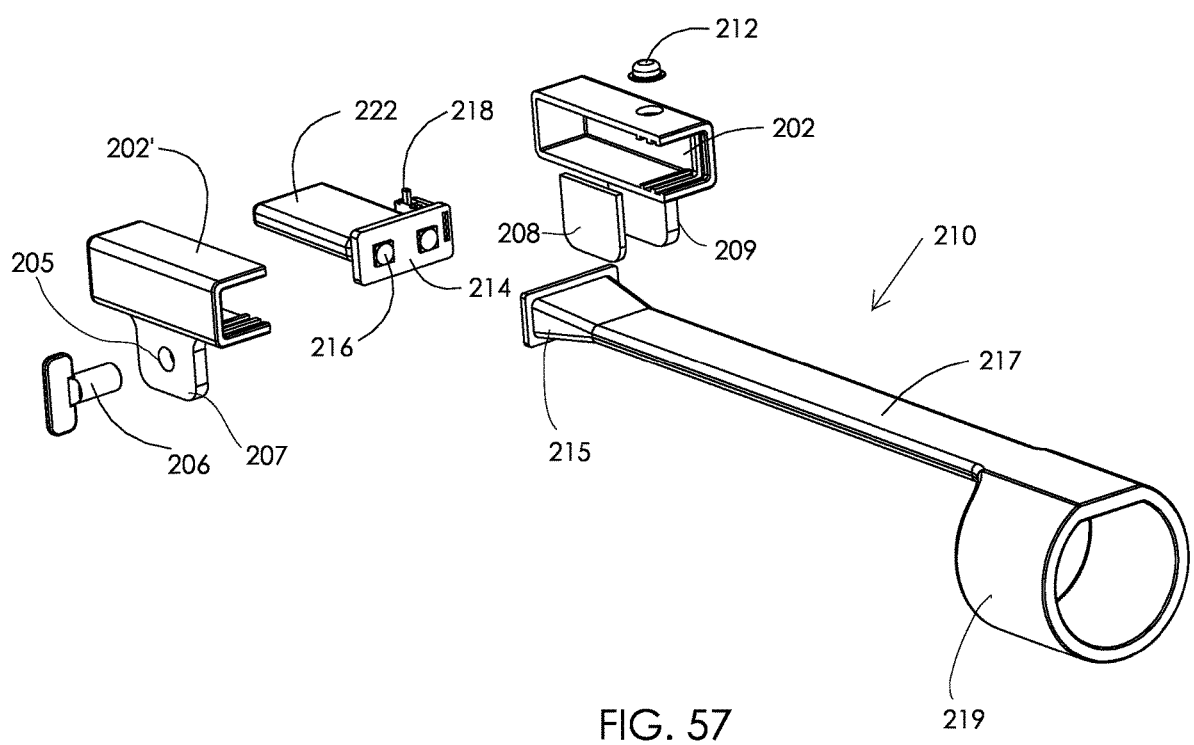
Figure 58:
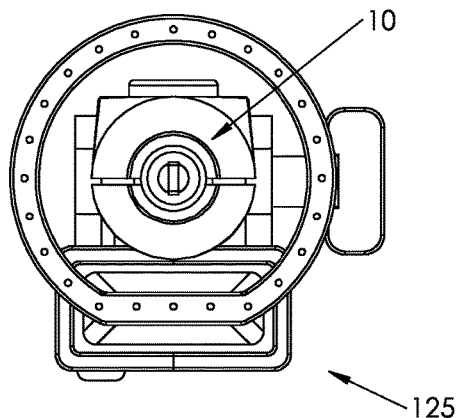
FIGS. 58 through 61 illustrate another embodiment of a lighting device for a handheld surgical instrument, which includes a subassembly attachment having fibers that function as a waveguide.

The housing 202, 202' of the lighting sub-assembly also has an attachment mechanism for detachably securing the lighting device 120 to a proximal end portion of the surgical instrument 10. The attachment mechanism includes an adjustable screw 206 that is supported in an aperture 205 formed in a first flange 207 extending from the bottom surface of housing portion 202' and second flange 209 extending from the bottom surface of housing portion 202 which has a resilient pad 208 on an interior surface thereof. In use, as best seen in FIGS. 54 and 55, a proximal end portion of a surgical instrument 10 is compressed between the end of the screw 206 in flange 207 and the pad 208 of flange 209.

Lighting device 120 further includes an elongated light guide sub-assembly 210 that includes a tapered proximal retainer portion 215 for engagement with the distal end of the housing 202, 202' and an elongated body portion 217 that extends distally from the proximal retainer portion 215 to a distal sleeve portion 219 that is adapted and configured to surround the distal end portion of a surgical instrument 10.

The body portion 217 and the distal sleeve portion 219 of the light guide sub-assembly 210 are integral with one another and formed from a polymer material that functions as a waveguide. More particularly, the body portion 217 and sleeve portion 219 contain a polymer material that transmits light from the LED light sources 216, through the body portion 219 to the distal end of the sleeve portion 219. In essence, the polymer functions as a waveguide (see, for example, U.S. Pat. Nos. 7,510,524 and 10,068,173).

Figure 59:
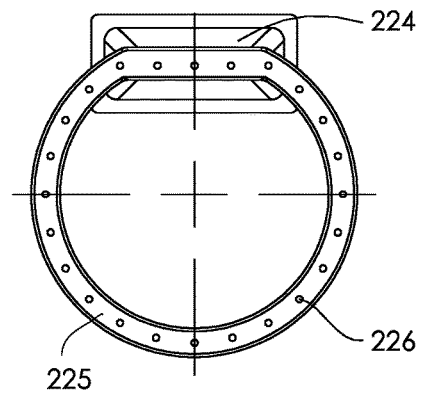
Figure 60:
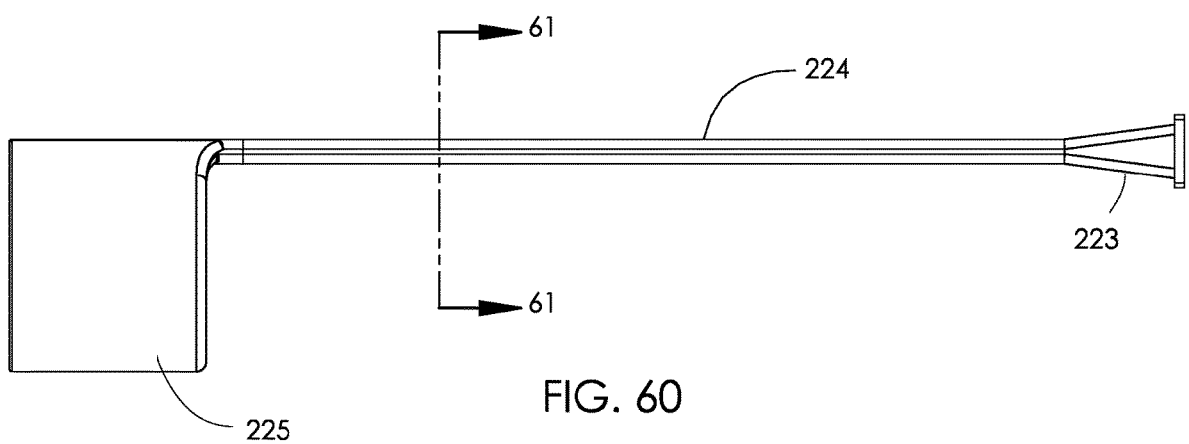
Figure 61:
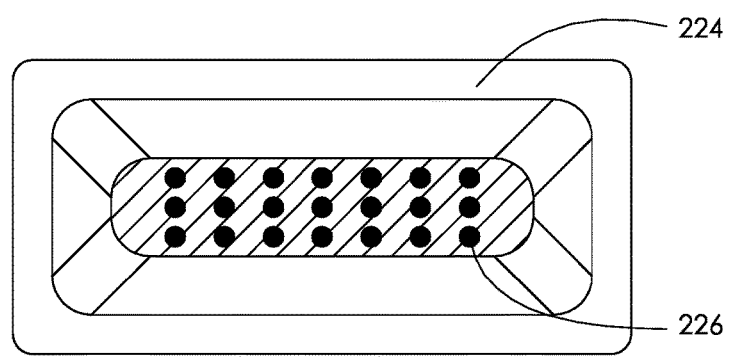
Figure 62:
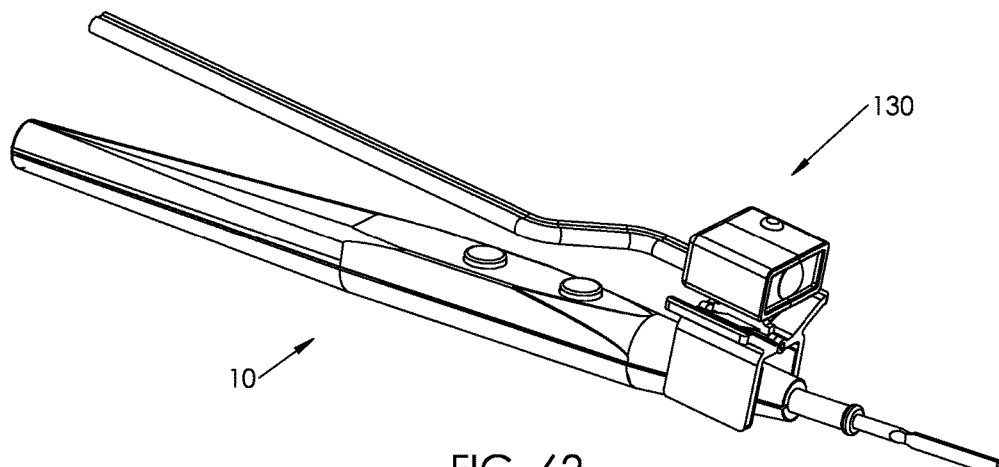
FIGS. 62 through 70 illustrate another embodiment of a lighting device for a handheld surgical instrument, which a clamping mechanism and an electrical wire for connecting with an electrical outlet to power the lighting device.
Figure 63:
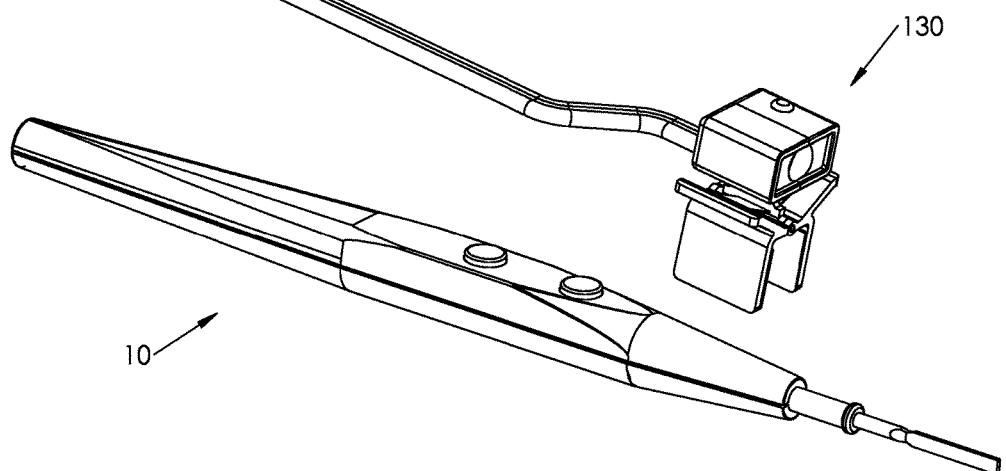
Figure 64:
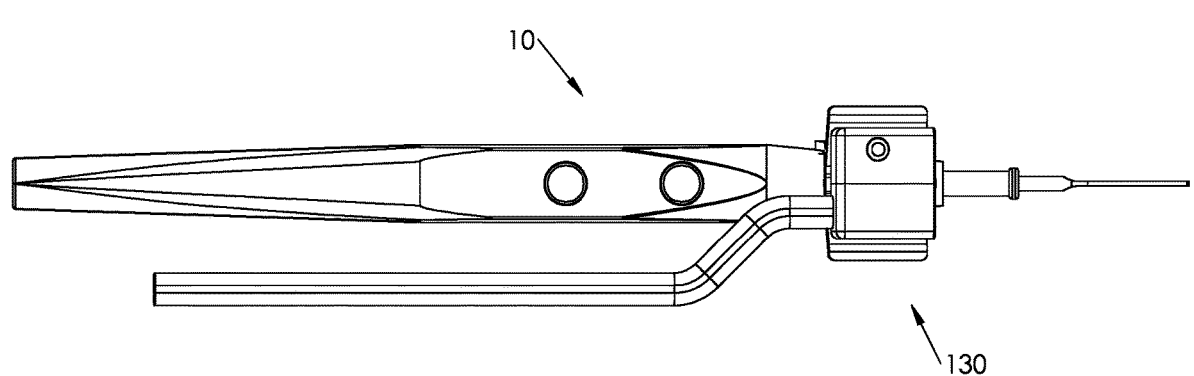
Figure 65:
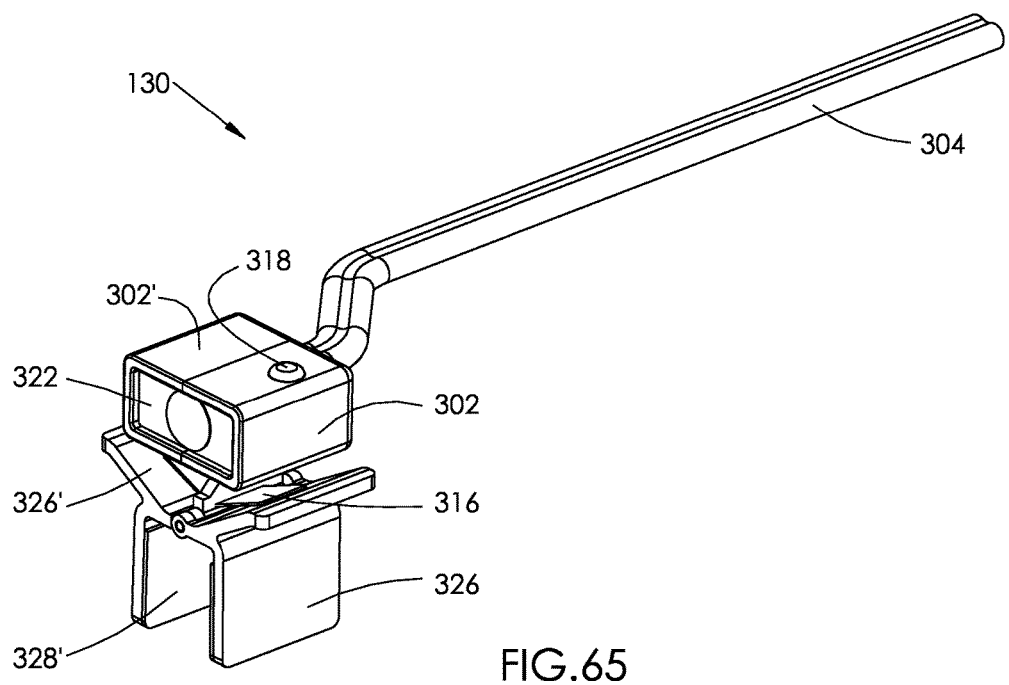
Figure 66:
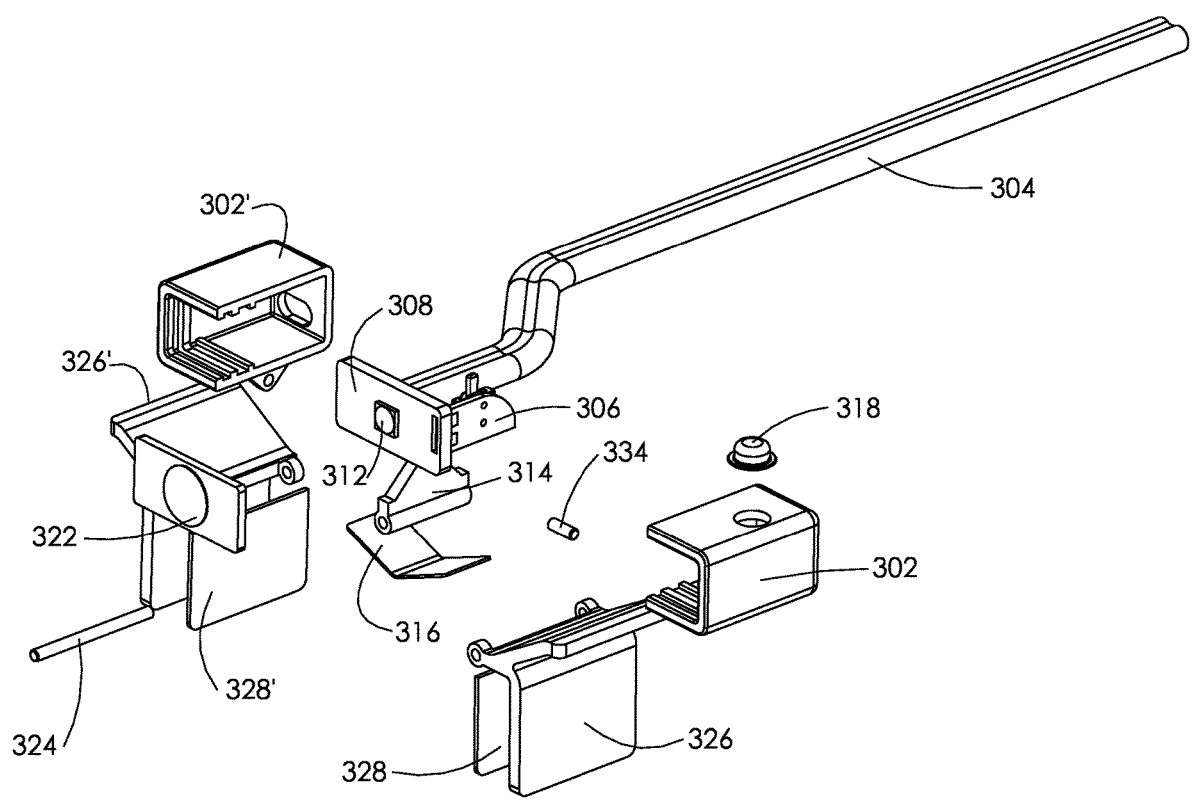
Figure 67:
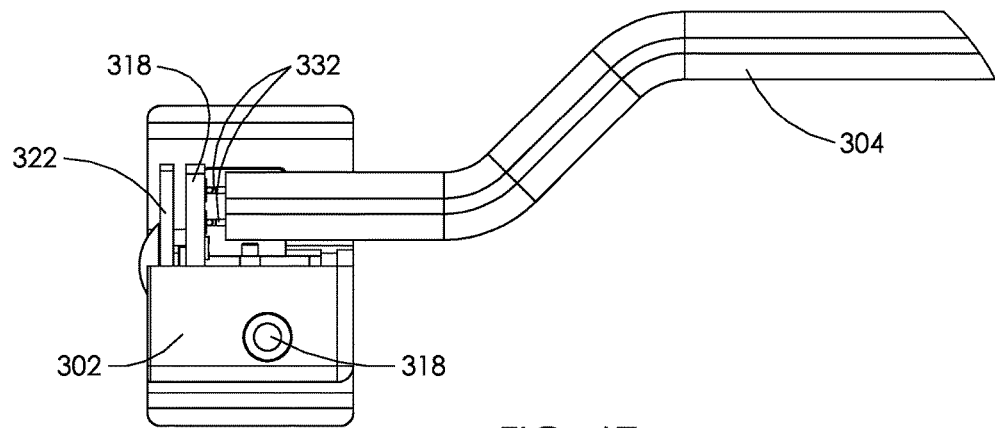

Referring to FIGS. 58 through 61, there is illustrated another embodiment of a light guide sub-assembly designated generally by reference numeral 125, which is configured for use with the lighting device 120. Sub-assembly 125 includes a proximal retainer portion 225, an elongated body portion 224 and a distal sleeve portion 225, wherein the body portion 224 and the sleeve portion 225 contain a plurality of optical fibers 226 that transmit light from the LED light sources 216, through the body portion 224 to the distal end of the sleeve portion 225. Preferably, the optical fibers 226 are distributed in spaced apart relationship about the periphery of the sleeve, as best seen in FIG. 59.

FIGS. 62 through 70 illustrate another embodiment of a lighting device for a handheld surgical instrument that is designated generally by reference numeral 130 and is adapted and configured for attachment to the distal end portion of a handheld surgical instrument 10. The lighting device 130 is substantially similar to the lighting device 20 described above with reference to FIGS. 1 through 14, except that the lighting device 110 includes an electrical wire 304 for connecting with an electrical outlet to power the lighting device. In all other respects, the device is nearly identical to lighting device 20 in that it includes a two-part housing 302, 302' containing a lens 322 and a PCB 308 with a LED light source 312 on a front surface thereof and a switch mechanism 306 on a rear surface thereof that is activated by a push button actuator 318.

Figure 68:
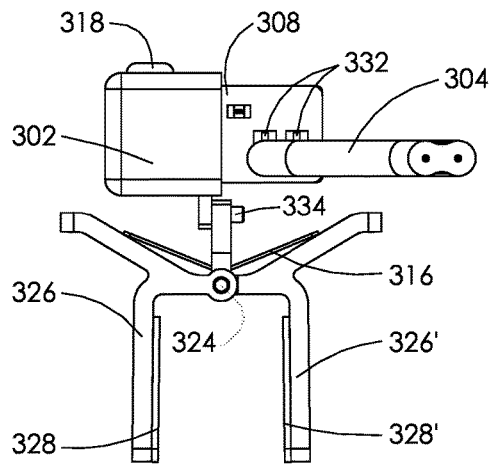
Figure 69:
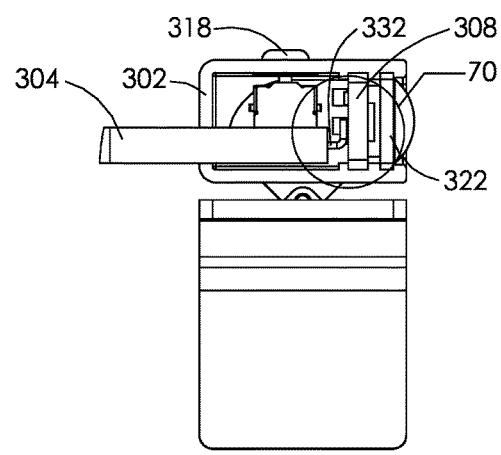
Figure 70:
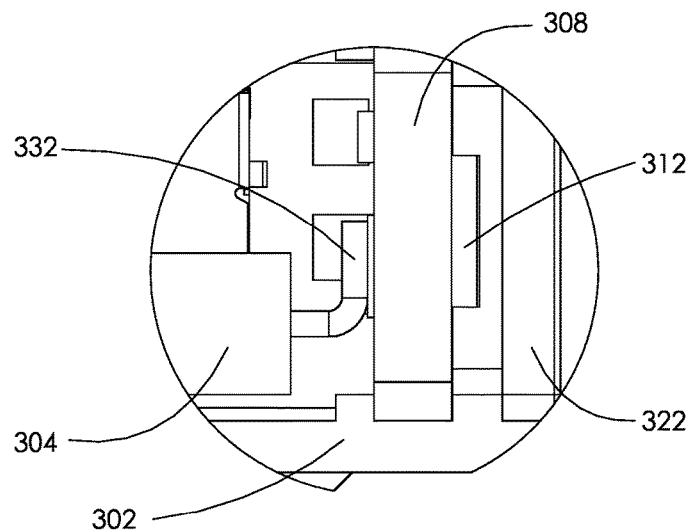
Figure 71:
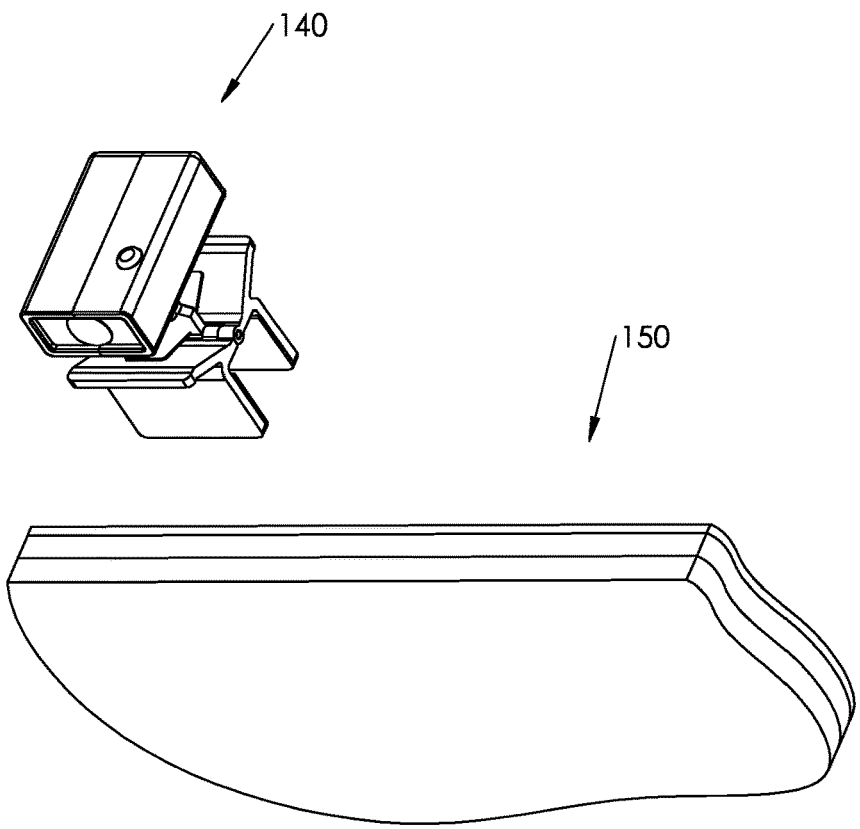
Figure 72:
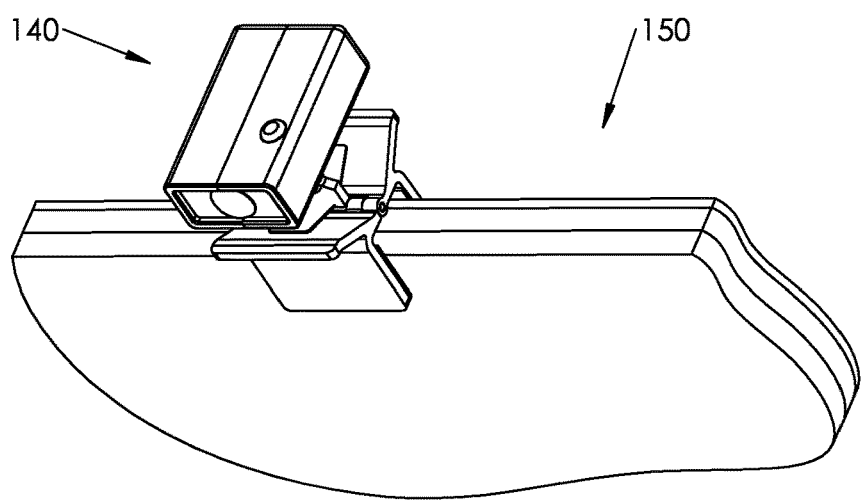
Figure 73:
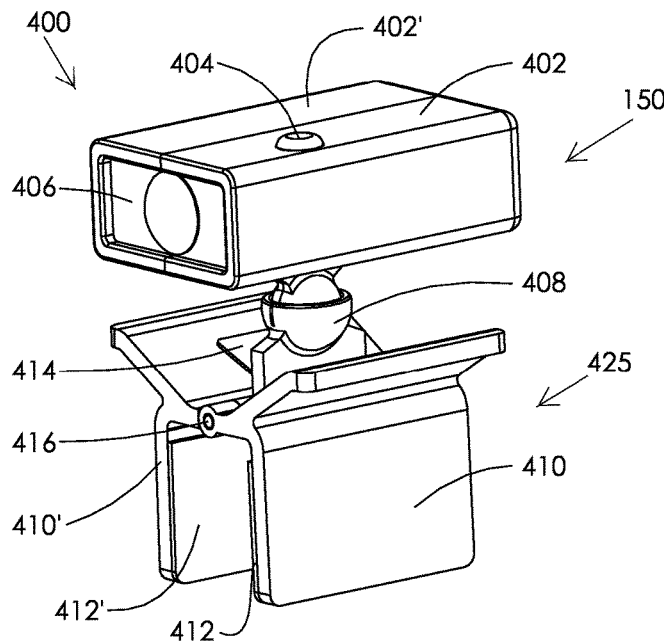
Figure 74:
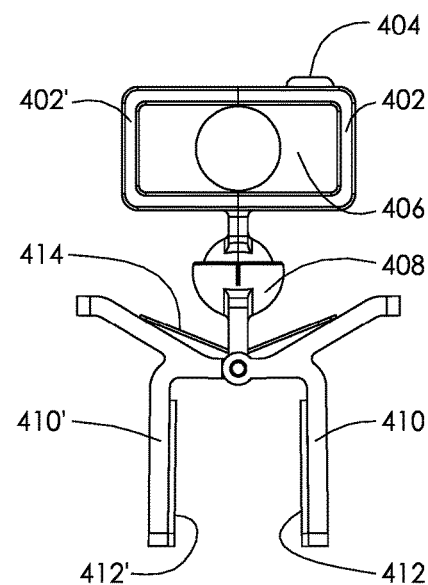
Figure 75:
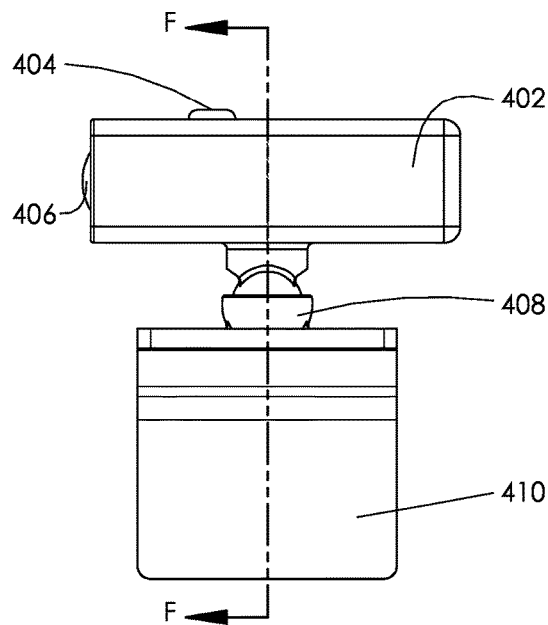
Figure 76:
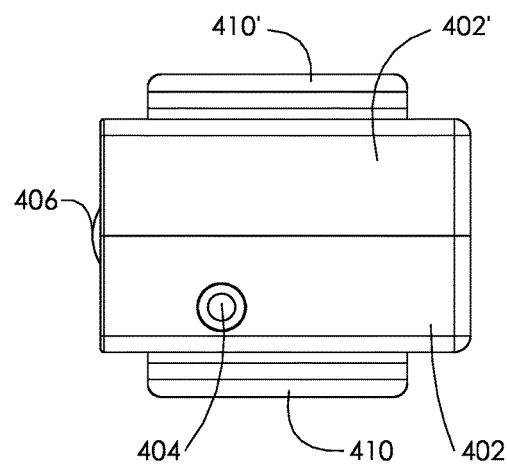
Figure 80:
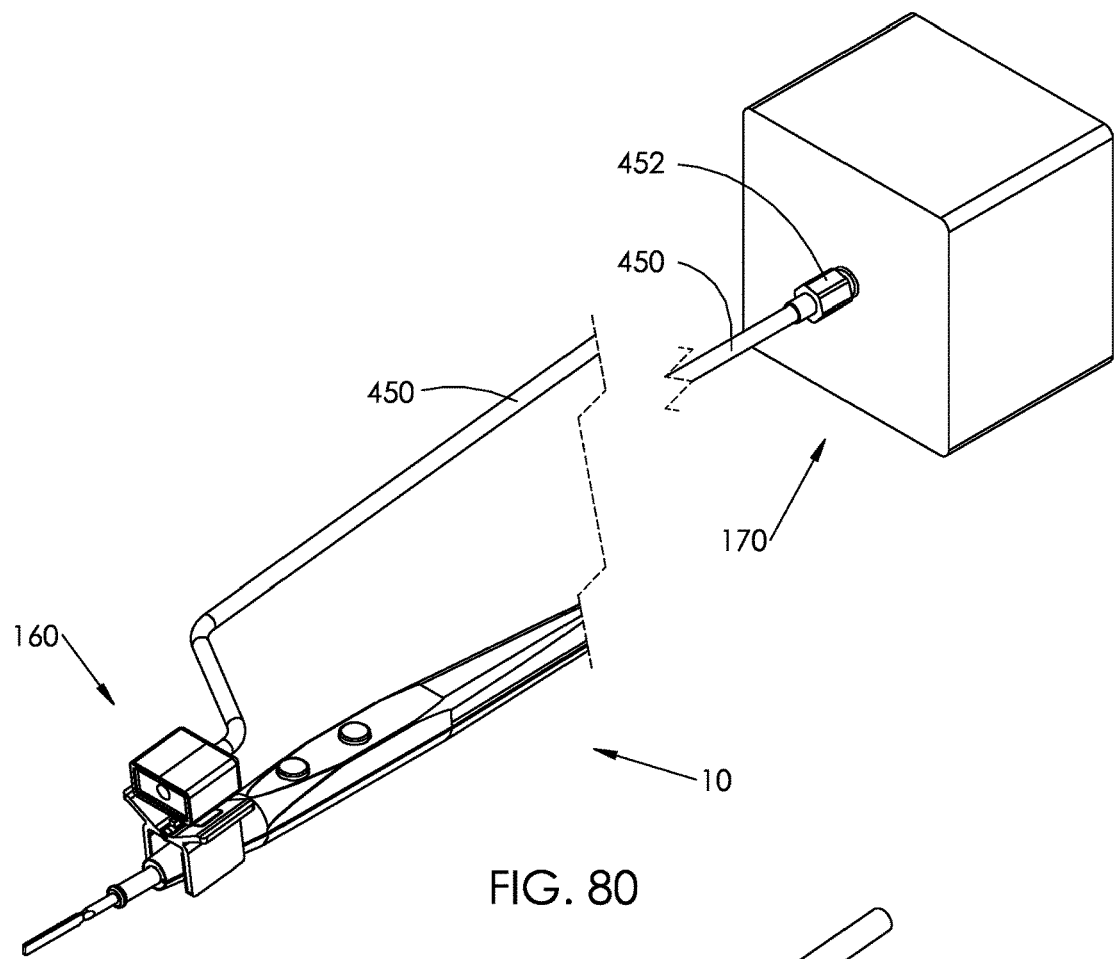
FIGS. 80 through 83 illustrate another embodiment of the lighting device of the subject invention, which includes a clamping mechanism for attaching the device to a handheld surgical instrument assembly, and a fiber cable attached to a remote light source.
Figure 81:
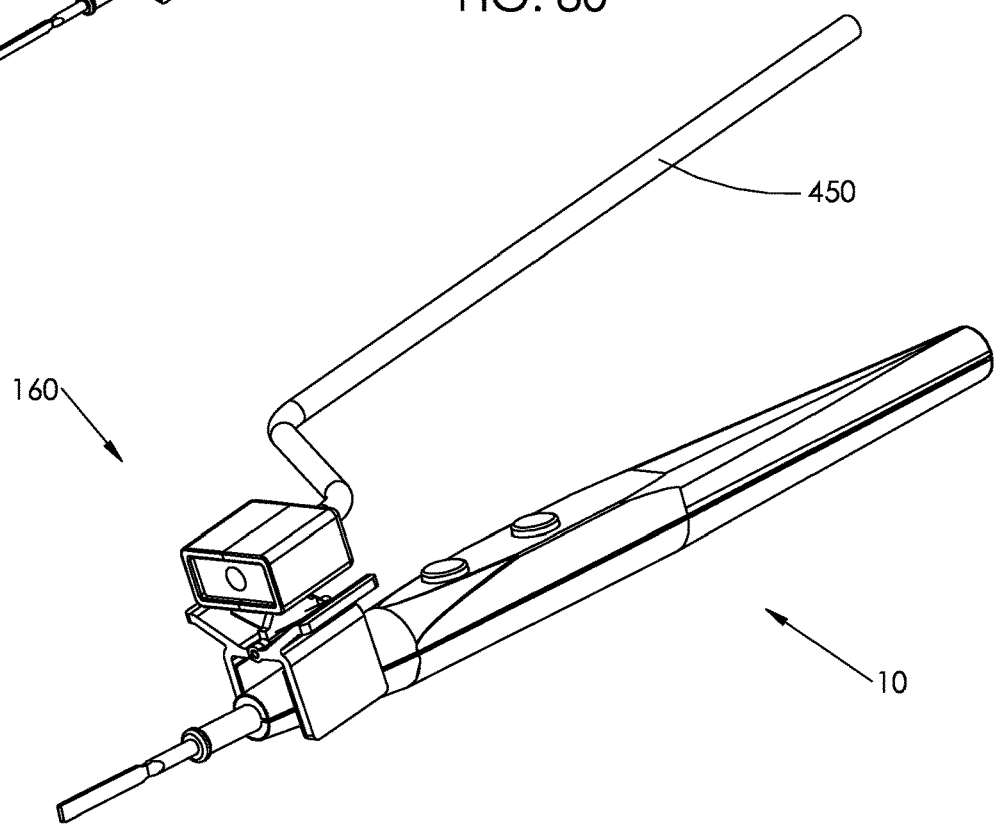
Figure 82:
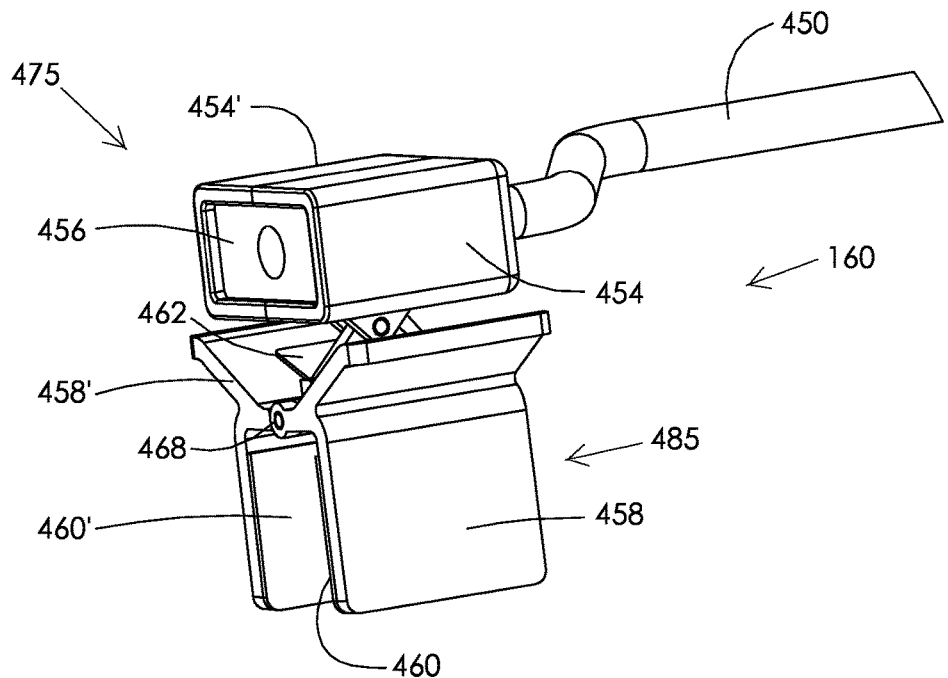
Figure 83:
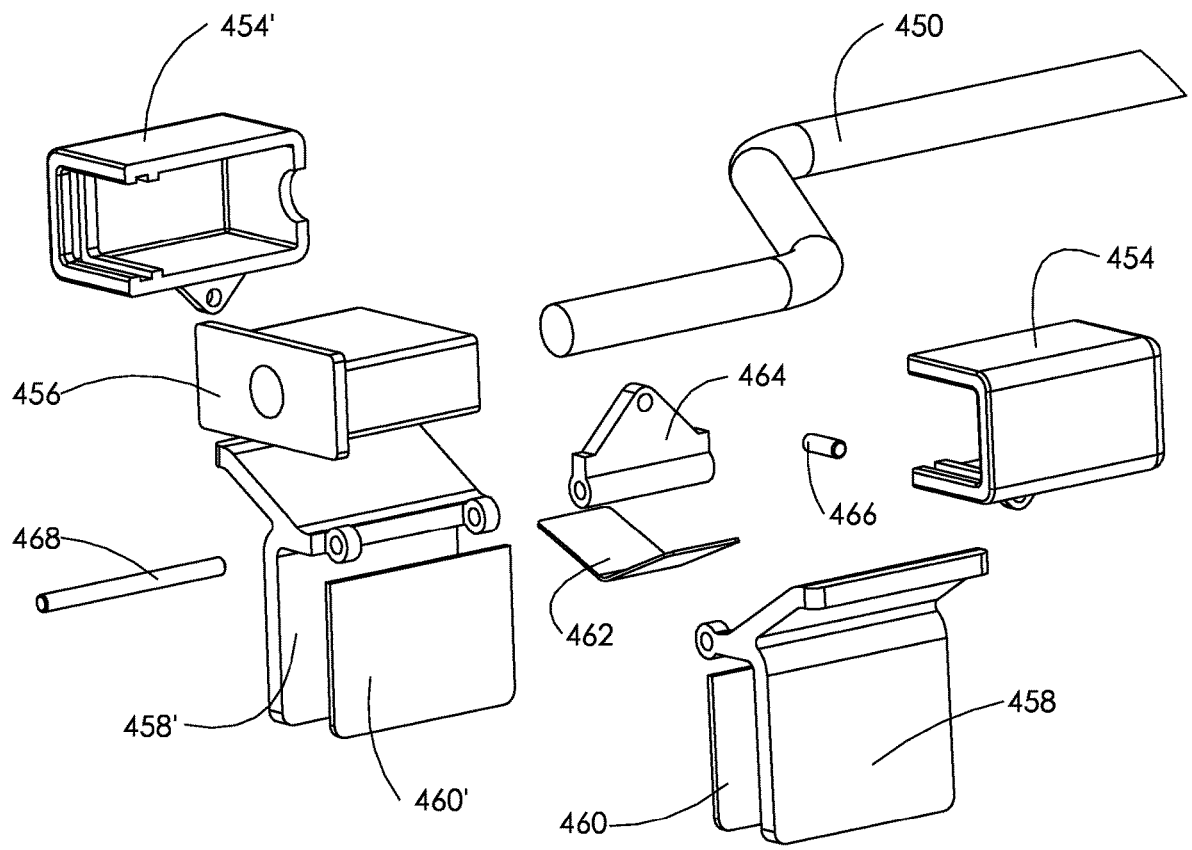
Figure 84:
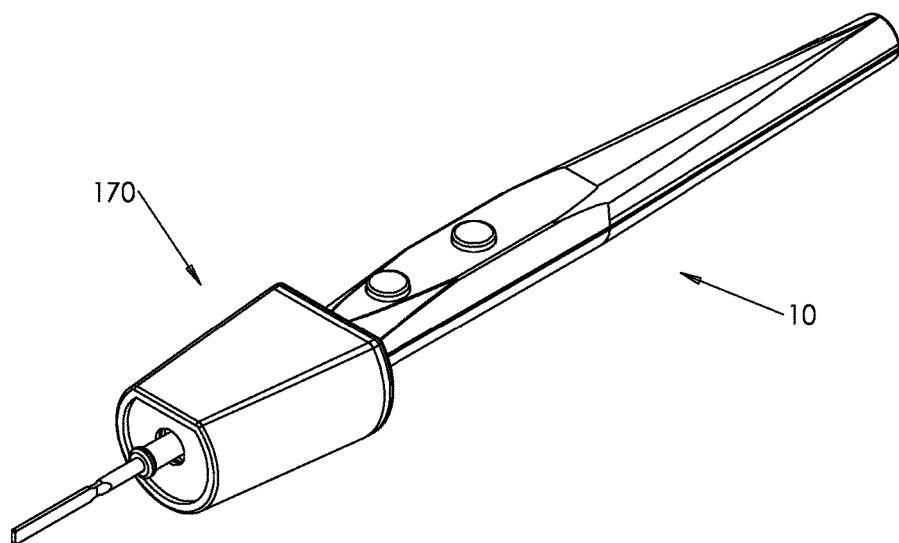
Figure 85:
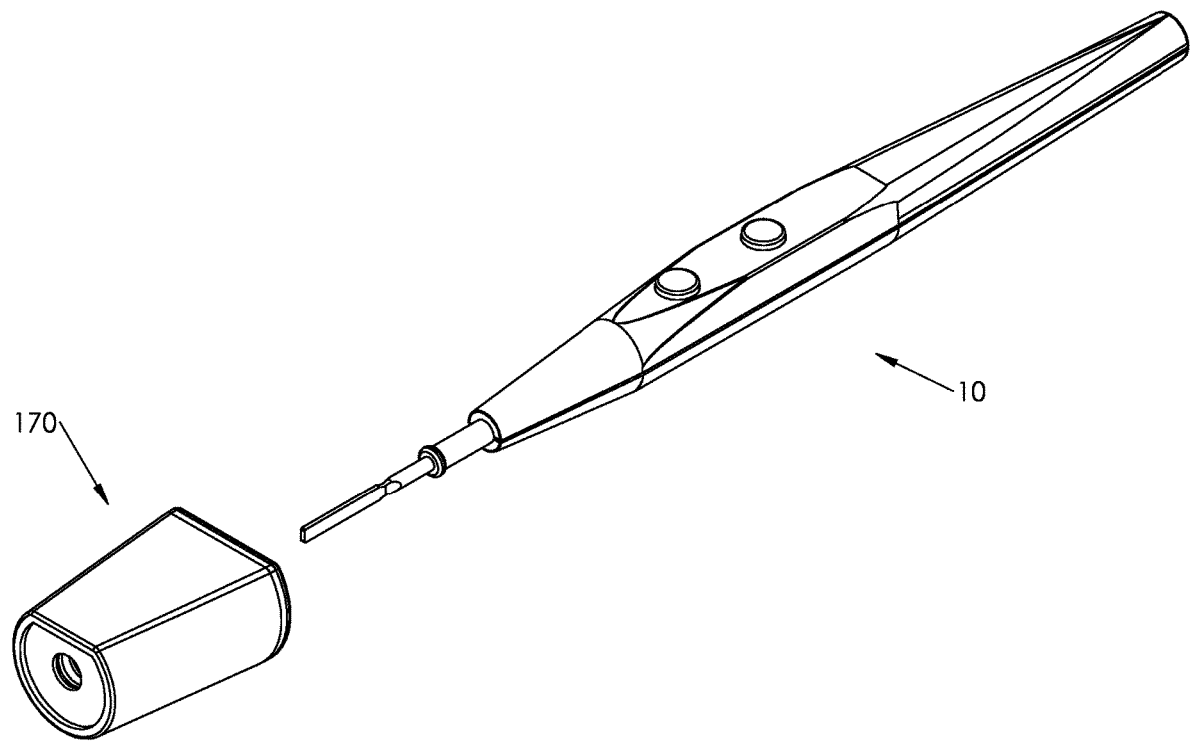
Figure 91:
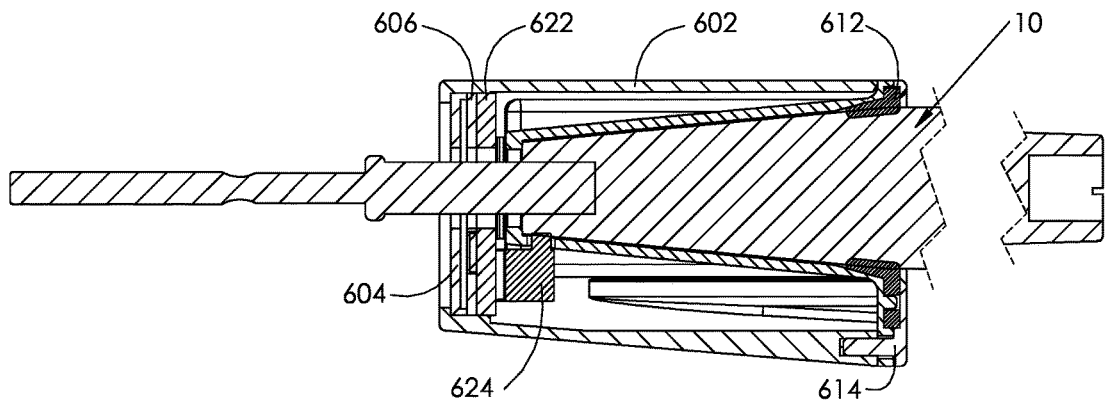
Figure 92:
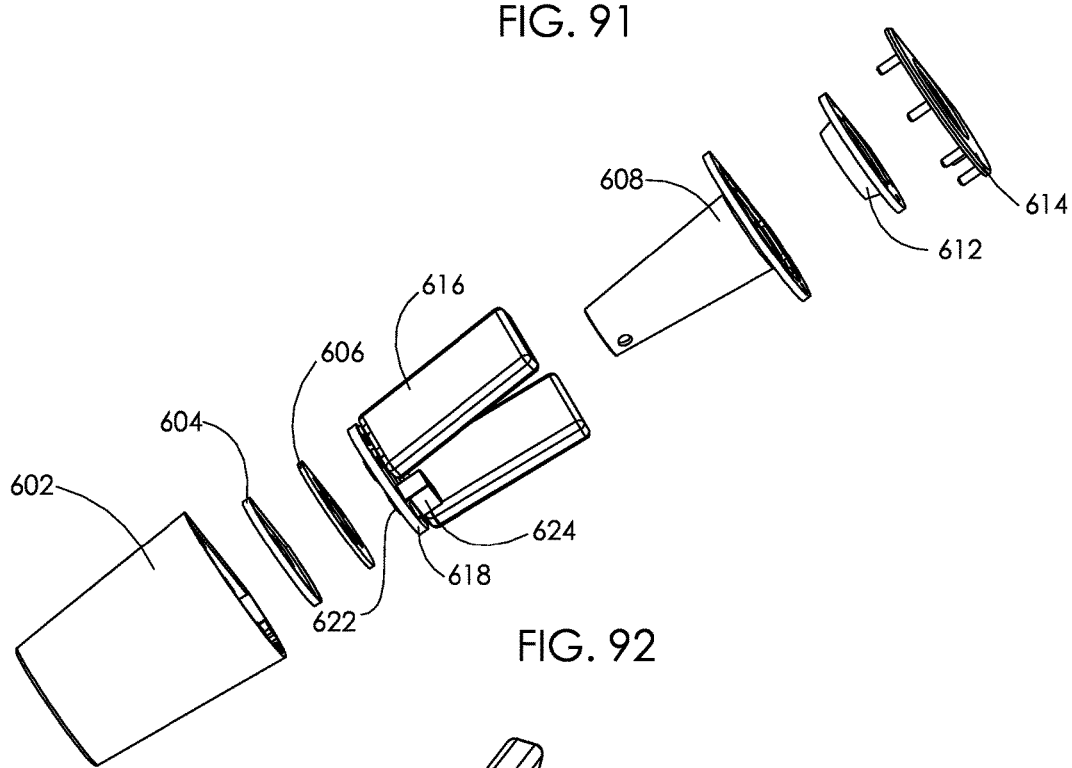
Figure 93:
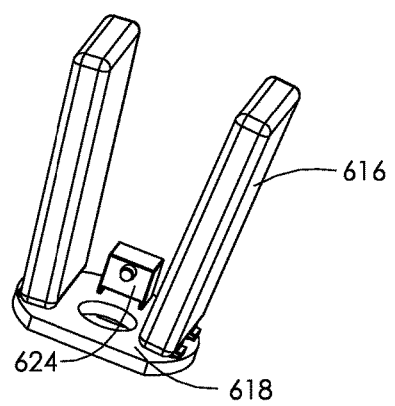
Figure 94:
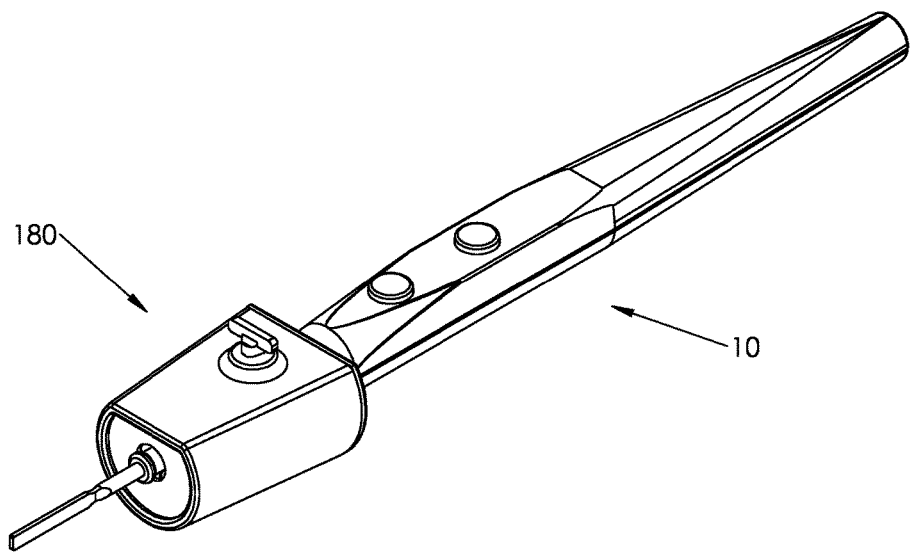
Figure 95:
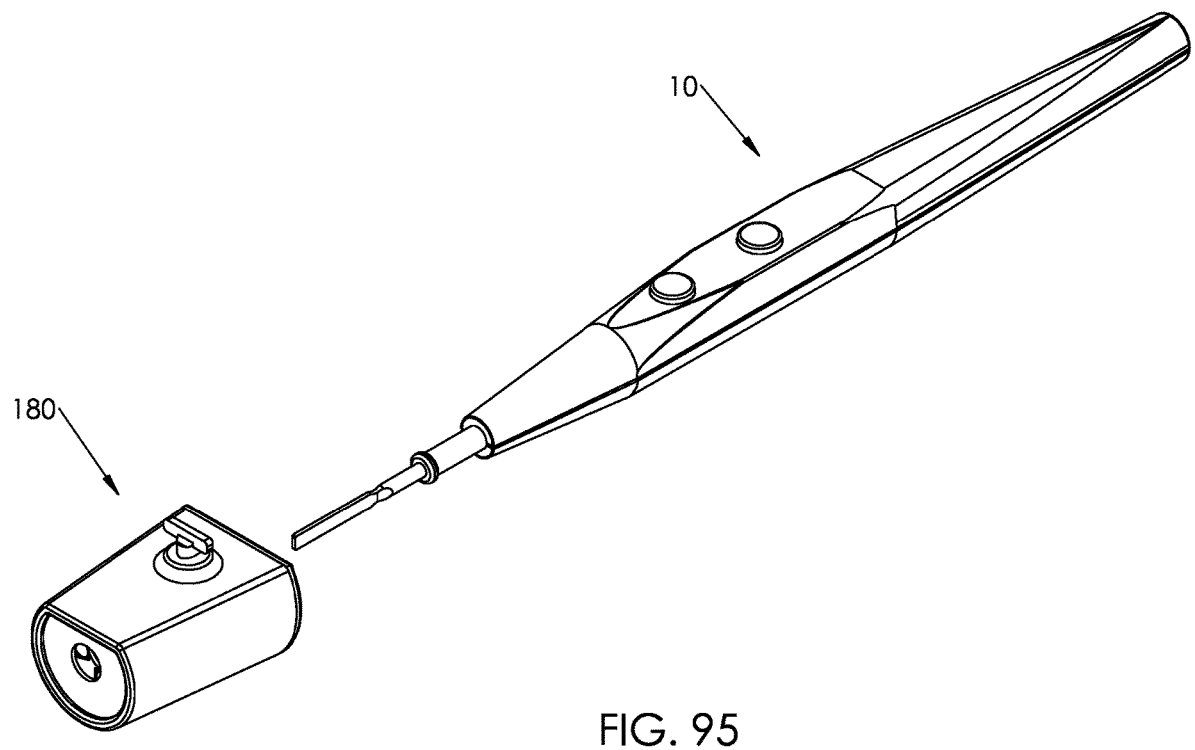
Figure 102:
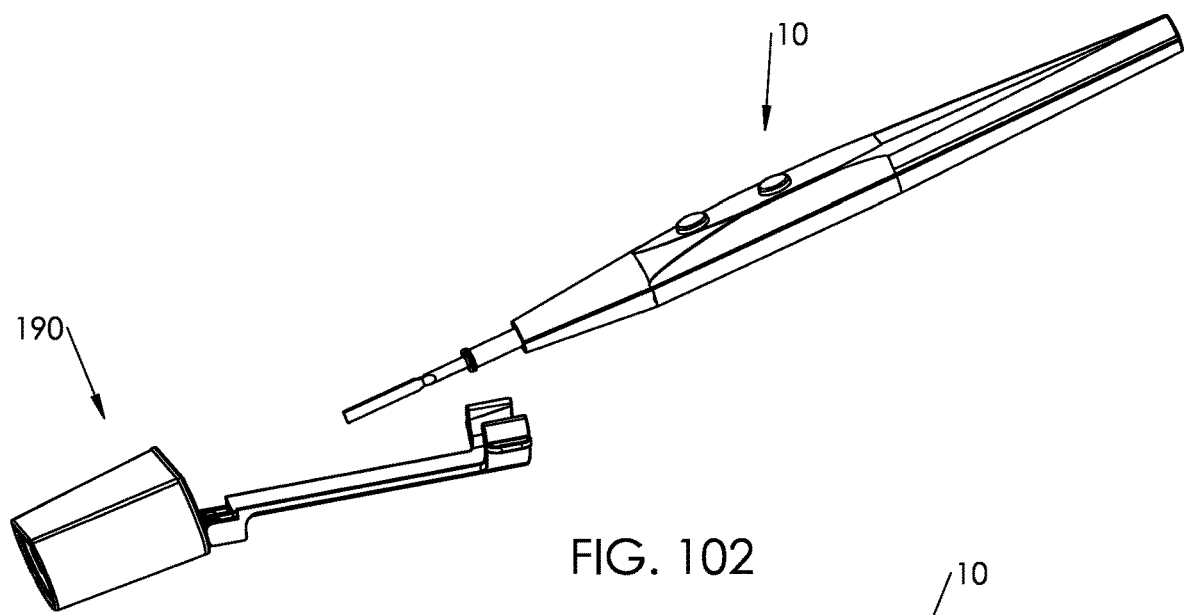
FIGS. 102 through 110 illustrate another embodiment of a lighting device which includes a pivoting tail bar with an engagement clasp for securing the device to the body of a handled surgical instrument.
Figure 103:
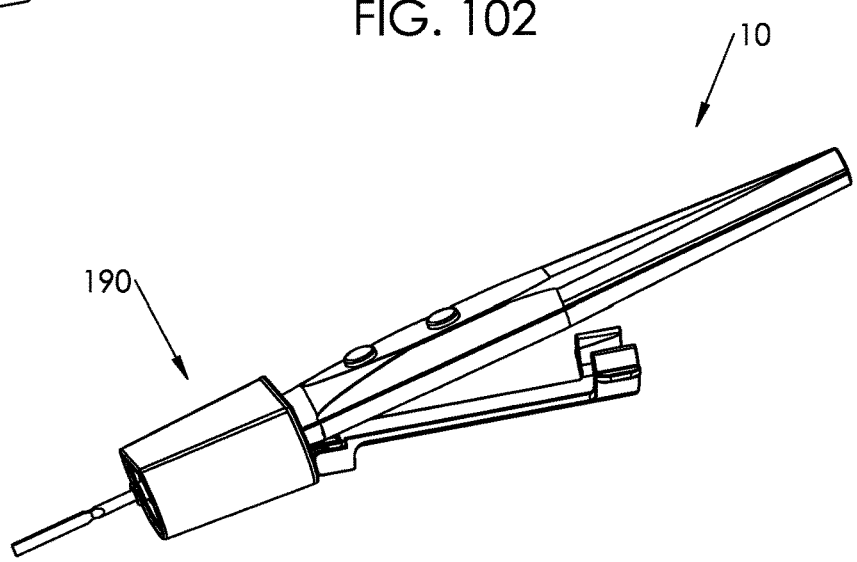
Figure 104:
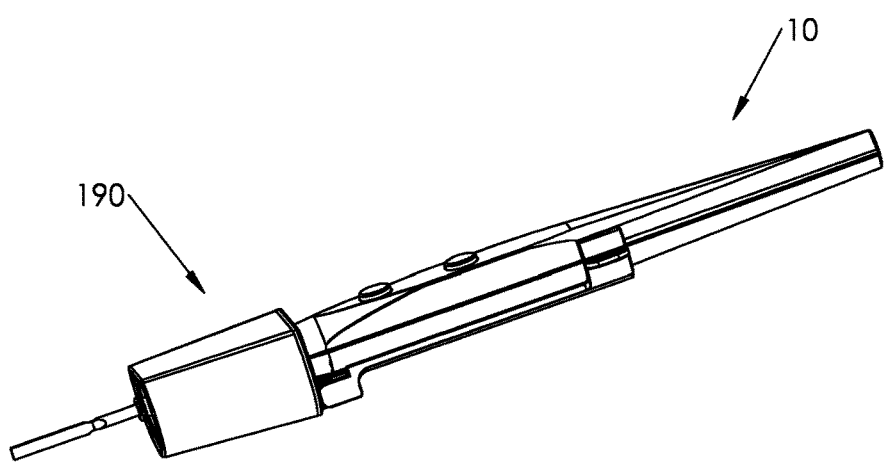
Figure 105:
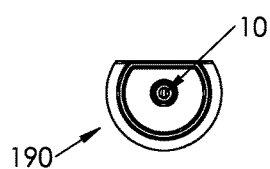
Figure 106:
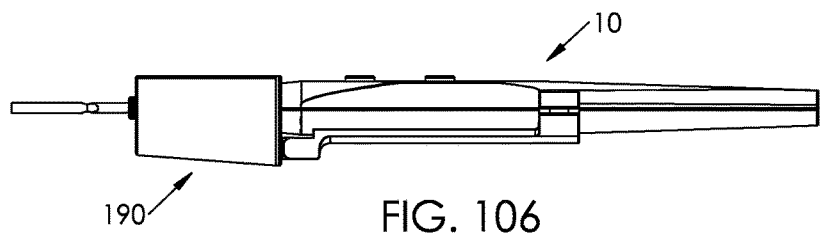
Figure 107:
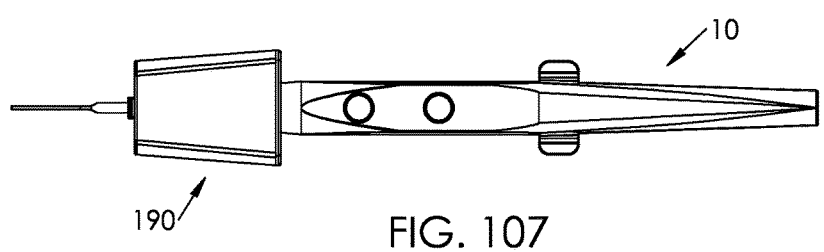
Figure 108:
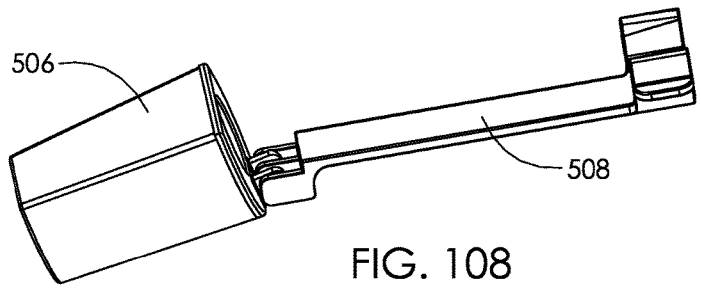
Figure 109:
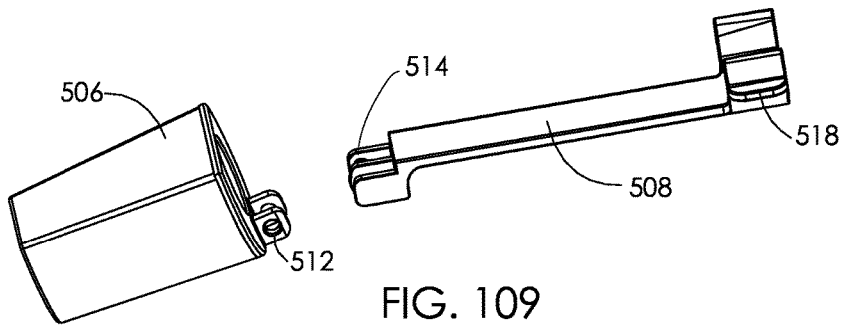
Figure 110:
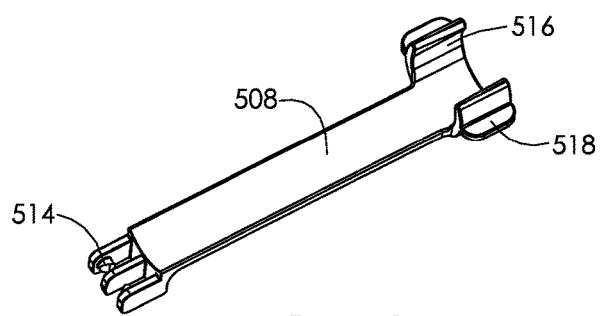
Figure 111:
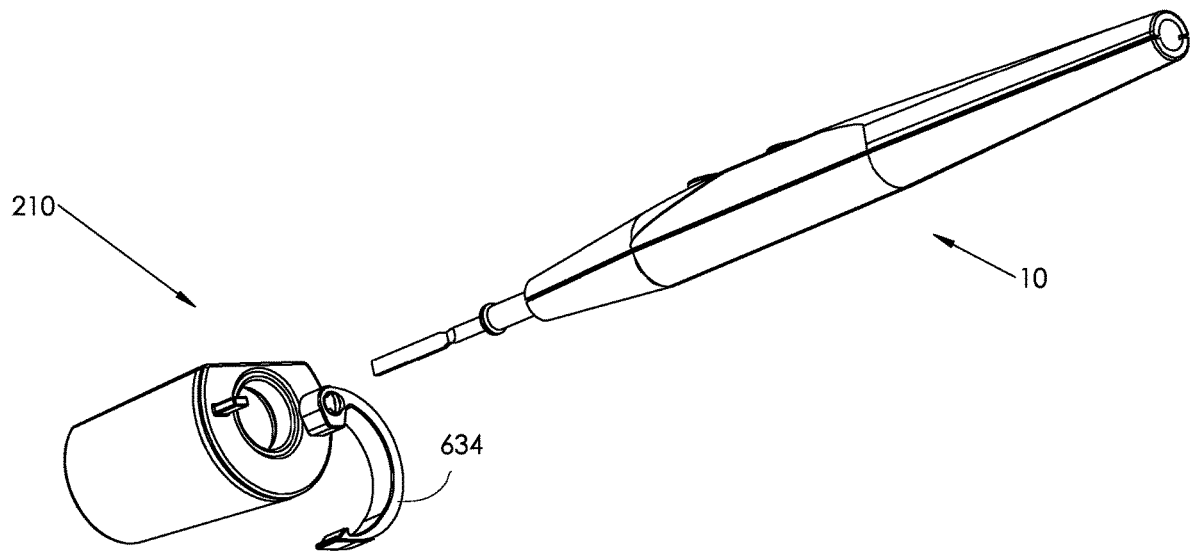
FIGS. 111 through 119 illustrate an embodiment of a lighting device that includes a pivoting securement arm for engaging a distal end portion of a handheld surgical instrument.
Figure 112:
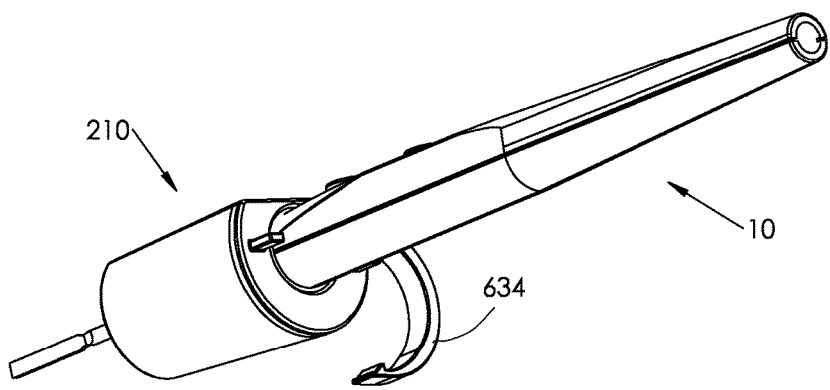
Figure 113:
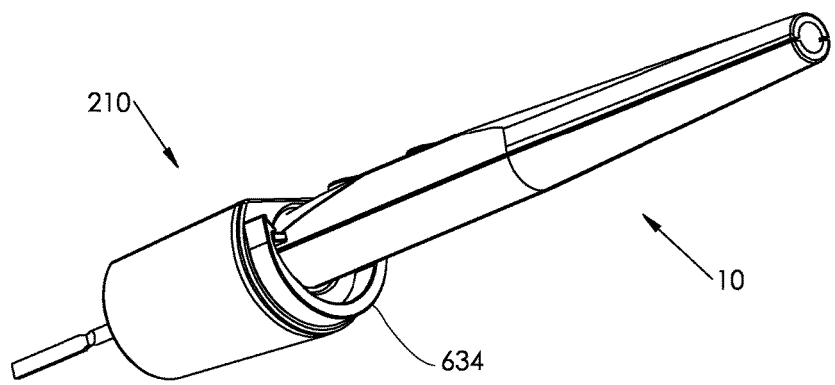
Figure 114:
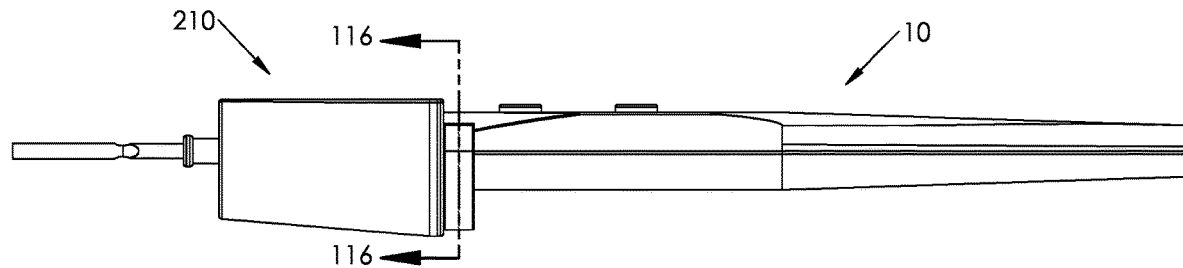

The electrical wire 304 communicates with contacts 332 on the rear surface of PCB 308, as best seen in FIGS. 68 and 69. The lighting device 130 also includes an attachment sub-assembly having a pair of engagement wings 326, 326 with respective interior compression pads 328, 328' that are spring biased into a clamping position by a torsion spring 316 and pivotably connected to a flange 314 by an elongated pin 324, where the flange itself is pivotably connected to the housing 302 by a transverse pin 334.

Referring now to FIGS. 71 through 79, there is illustrated another embodiment of a lighting device which is designated generally by reference numeral 140 and is adapted and configured for attachment to body tissue of a patient to illuminate the operating site. Here, the lighting device 140 is substantially similar to the lighting device 20 shown in FIGS. 1 through 14, except that the pivot axis of the clamping mechanism, which is defined by the elongated pivot pin (i.e., pivot pin 22), extends perpendicular to the longitudinal axis of the lighting sub-assembly, and thus the illumination axis of the lighting device.

It is further envisioned that this embodiment of the lighting device 140 could be used for attachment to a section of a surgical drape used during a surgical procedure involving an open operative site. It is envisioned that multiple lighting devices of the type shown in FIGS. 71 and 72 could be readily attached to a surgical drape and arranged around the perimeter of a surgical wound, and the devices could be angled in such a manner so as to create arena style lighting for the surgical site.

Referring now to FIGS. 73 through 79, there is illustrated yet another embodiment of the lighting device of the subject invention that is designated generally by reference numeral 150, wherein the lighting sub-assembly 400 is rotationally connected to the clamping sub-assembly 425 by a ball and socket joint so as to enable a surgeon to orient the illumination axis of the lighting device 150 with respect to the longitudinal axis of the surgical instrument 10.

As best seen in FIG. 77, the lighting sub-assembly 400 of lighting device 150 is substantially identical to the lighting sub-assembly of the lighting device 20 shown in FIGS. 1 through 14, in that it includes a two-part housing 402, 402' containing a lens 406 and a PCB 420 with an LED light source 422 on a front surface thereof and a battery cell 418 and switch mechanism 424 and on a rear surface thereof that is activated by a push button actuator 404. The clamping sub-assembly 425 of lighting device 150 includes a pair of engagement wings 410, 410' with respective interior compression pads 412, 412' that are spring biased into a clamping position by a v-shaped torsion spring 414 and they are pivotably connected to one another and to a connective flange 408 by an elongated pin 416. Here, the connective flange 408 incudes a bore 430 for receiving the pivot pin 416 and a hemi-spherical socket 428 for accommodating a two-part ball 426, 426 that extends respectively from the housing portions 402, 402' of lighting sub-assembly 400.

Referring to FIGS. 80 through 83, there is illustrated another embodiment of the lighting device of the subject invention that is designated generally by reference numeral 160 and includes a lighting sub-assembly 475 for illuminating a surgical site, a clamping sub-assembly 485 for attaching the device to a handheld surgical instrument 10, and an elongated light tube or fiber optic cable 450 attached by a coupling 452 to a remote light source 170. Alternatively, the fiber optic cable 450 could be attached to a capital equipment device housed outside the sterile field (e.g., a permanent or multiuse device).

Here, the lighting sub-assembly 475 includes a two-part housing 454, 454' containing a junction box 456 for receiving the distal end of the fiber optic cable 450 and the clamping sub-assembly 485 includes a pair of engagement wings 458, 458' with respective interior compression pads 460, 460' that are spring biased into a clamping position by a v-shaped torsion spring 462 and they are pivotably connected to one another and to a connective flange 464 by an elongated pin 468, and the connective flange is pivotably connected to the lighting sub-assembly 475 by a transverse pin 466.

Referring now to FIGS. 84 through 93, there is illustrated yet another embodiment of a lighting device for use with a handheld surgical instrument 10, which is designated generally by reference numeral 170 and which is similar to the lighting device 90 shown in FIGS. 39 through 42. But in this embodiment of the invention, the outer housing 602 of lighting device 170 has a generally frusto-conical configuration with a trapezoidal shaped upper surface. The planar upper surface is configured for planar alignment with an upper surface of the surgical instrument 10 so that a line of sight extending along the upper surface of the surgical instrument 10 remains unobstructed by the lighting device 170.

The housing 602 encloses an inner body portion 608 for accommodating the distal end portion of the surgical instrument 10, an PCB 618 with a plurality of LED light sources 622 on a front surface thereof and a contact switch 624 on a rear surface thereof for activating the LED light sources upon insertion of the distal end portion of the surgical instrument 10. A pair of battery cells 616 are also associated with the rear surface of the PCB 622 for powering the LED light sources 622.

A lens 604 is positioned in the distal end pf the housing 622 for focusing the light sources and a spacer or protector 606 is positioned between the lens 604 and the LED light sources. In lighting device 170, the LED light sources 622 extend about the distal end of the outer housing 602, behind lens 604 in an asymmetric configuration relative to a longitudinal axis of the surgical instrument. A compliant securing ring 612 is positioned in the outer housing 602 adjacent the proximal end of the inner body portion 608 for mechanically engaging and retaining the distal end portion of the surgical instrument 10 within the lighting device 170, and a proximal end cap 614 maintains the compliant securing ring 612 in place.

Referring to FIGS. 94 through 101, there is illustrated another embodiment of the lighting device of the subject invention which is designated generally by reference numeral 180, and which is substantially similar to the lighting device 170 shown in FIGS. 84 through 93, at least with respect to the geometry of the outer housing. In this embodiment, the lighting device 180 includes a manually adjustable securement screw 504 that is located on the planar upper surface of the outer body portion 502. The securement screw 504 is adapted and configured to selectively engage the distal end portion of the surgical instrument 10 when it is inserted into the lighting device 180.

Referring now to FIGS. 102 through 110, there is illustrated yet another embodiment of the lighting device of the subject invention which is designated generally by reference numeral 190 which includes a pivoting tail bar 508 for securing the device 190 to the body of a handled surgical instrument 10. The tail bar 508 includes a distal boss structure 514 for pivotably engaging with a proximal boss structure 512 that extends from the proximal end of the housing 596 of lighting device 190. A deflectable clasp 516 is formed at the proximal end of the tail bar 508 for mechanically engaging the body of the surgical instrument 10. The deflectable clasp 516 includes opposed flanges 518 for spreading apart and disengaging the clasp 516 from the surgical instrument 10.

Referring to FIGS. 111 through 119, there is illustrated another embodiment of a lighting device of the subject invention which is designated generally by reference numeral 210 which is substantially similar to the lighting device 170 shown in 84 through 93, but lighting device 210 further includes a pivoting securement arm 634 that is adapted and configured to mechanically or compressively engage a distal end portion of a handheld surgical instrument 10.

Figure 115:
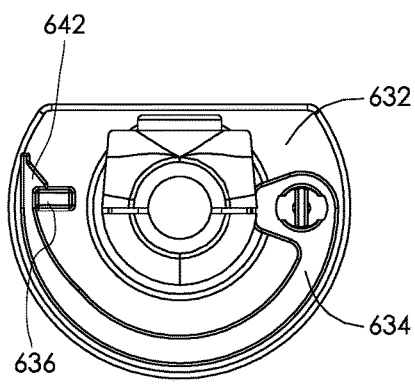
Figure 116:
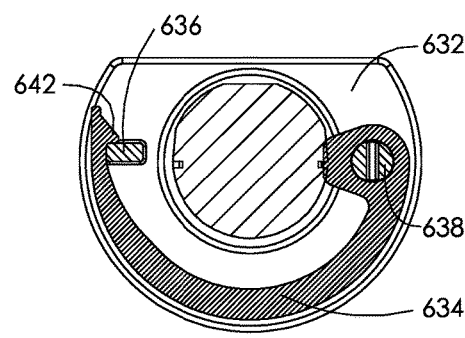
Figure 117:
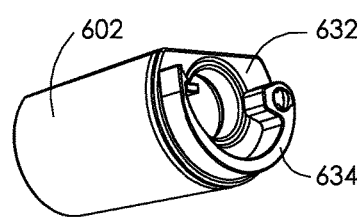
Figure 118:
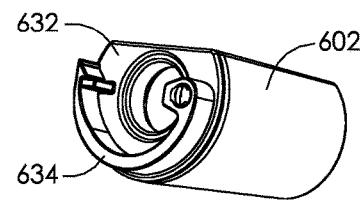
Figure 119:
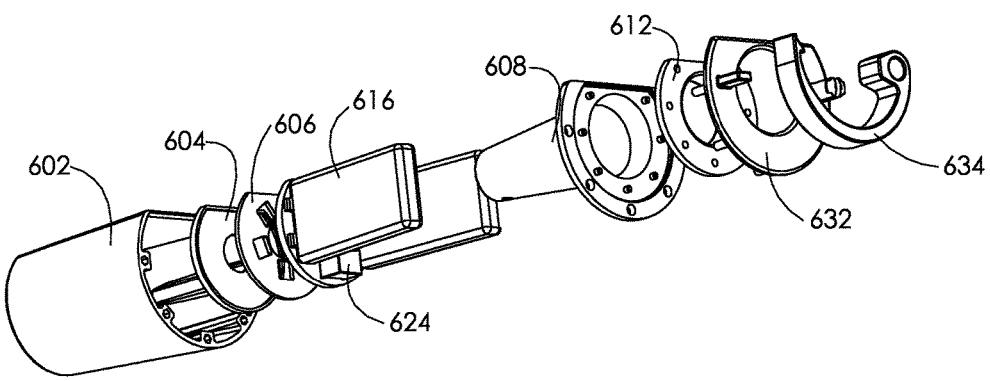

More particularly, the securement cam arm 634 is rotational attached to a proximal end cap 632 of the outer body portion 602 for rotating about a pivot pin 638 on an axis that extends parallel to a longitudinal axis of the surgical instrument 10. The free end of the securement arm 634 has a tang 642 for capturing a locking flange 636 that projects proximally from the surface of end cap 632 to retain the arm 634 in a retaining position, as best seen in FIGS. 115 and 116.

Currently, to prevent burns or accidental activations, it is known to place an electrosurgical instrument into a holster when it's not being used. Sometimes this holster is tied to or hung on the surgical drapes near the patient for easy access for the surgeon. These holsters are designed to fit the instrument with a lighting device attached thereto, and also turn off the lighting device so the user is able to preserve battery life when the device is not in use.

Referring to FIGS. 1A through 16A, there is illustrated a new and useful system for performing a surgical procedure which includes a battery powered lighting device 1020 configured for attachment on the distal end portion of a handheld surgical instrument 10 and an elongated holster 1030 for accommodating the surgical instrument 10 with the lighting device 1020 attached thereto.

As best seen in FIGS. 11A through 16A, the lighting device 1020 includes right and left body portions 1002 and 1002' housing an inner body portion 1008 and a having a proximal end cap 1004 with a central aperture for receiving the distal end portion of the lighting device 10. A stamped engagement ring 1006 having circumferentially spaced apart teeth is positioned adjacent the end cap 1004 for mechanically engaging the surgical instrument 10 upon insertion thereof into the inner body portion 1008.

A PCB 1024 is located within the distal end of the body 1002, 1002' of lighting device 1020 and it has a plurality of circumferentially spaced apart LED light sources 1018 on a front surface thereof and a primary switch 1022 is positioned on the rear surface of the PCB 1024 for activating the LED light sources 1018 upon insertion of the surgical instrument 10 into the lighting device 1020. A plurality of battery cells 1026 are also associated with the rear surface of the PCB 1024 for powering the LED light sources 1018, and a lens 1014 is located in front of the LED light sources 1018.

Figure 5A:
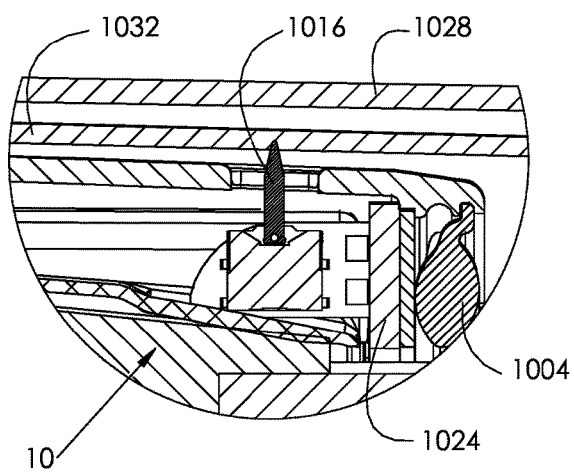
Figure 6A:
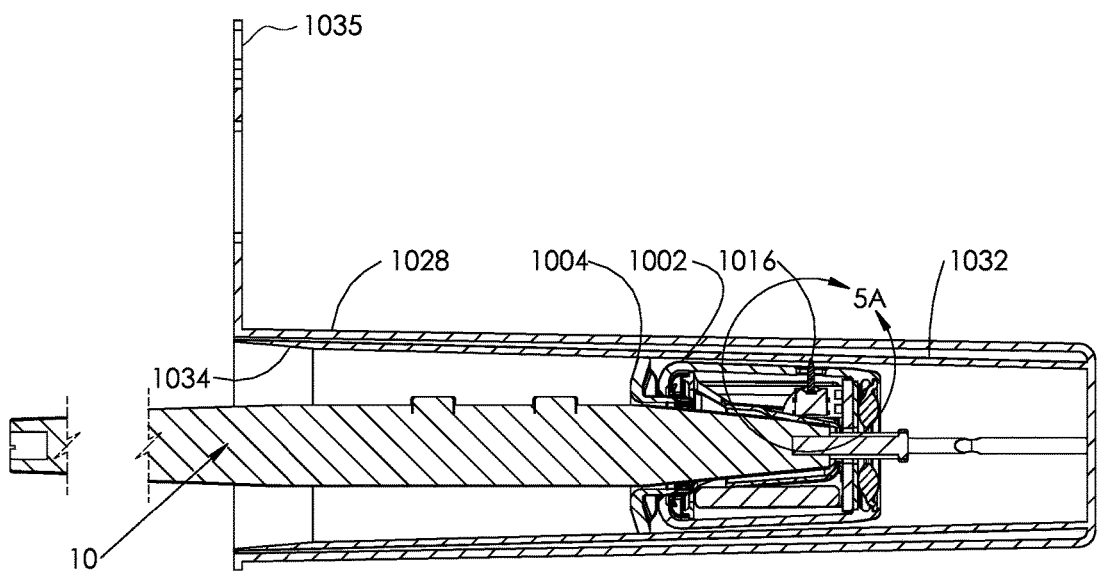
Figure 4C:
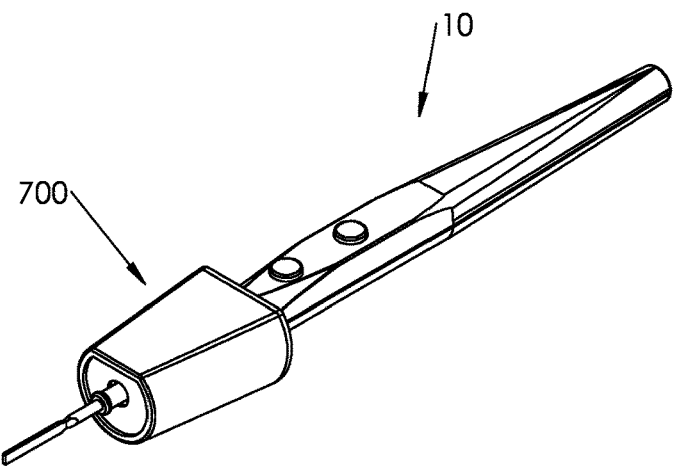
Figure 5C:
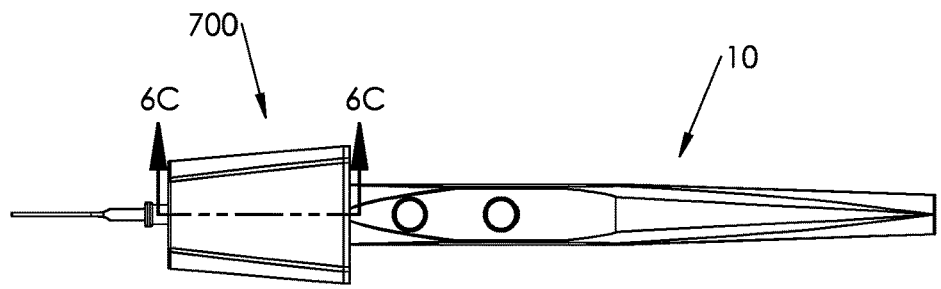

A second switch 1016 is also provided on the rear surface of the PCB 1024 for controlling the LED light sources 1018 when the surgical instrument 10 and lighting device 1020 are inserted into the holster 1030 together. In particular, as shown in FIGS. 5A and 6A, the holster body 1028 includes an inner reception bore 1032 that defines a generally cylindrical peripheral contact surface which mechanically interacts with the switch 1016 to turn off the LED light sources 1018 when the assembly is received therein.

Figure 10A:
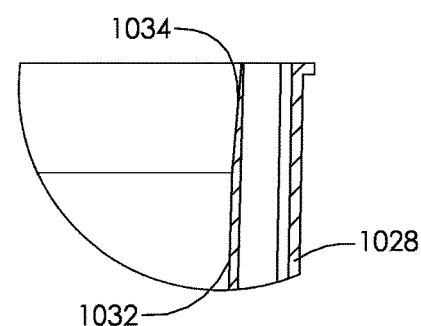
Figure 7B:
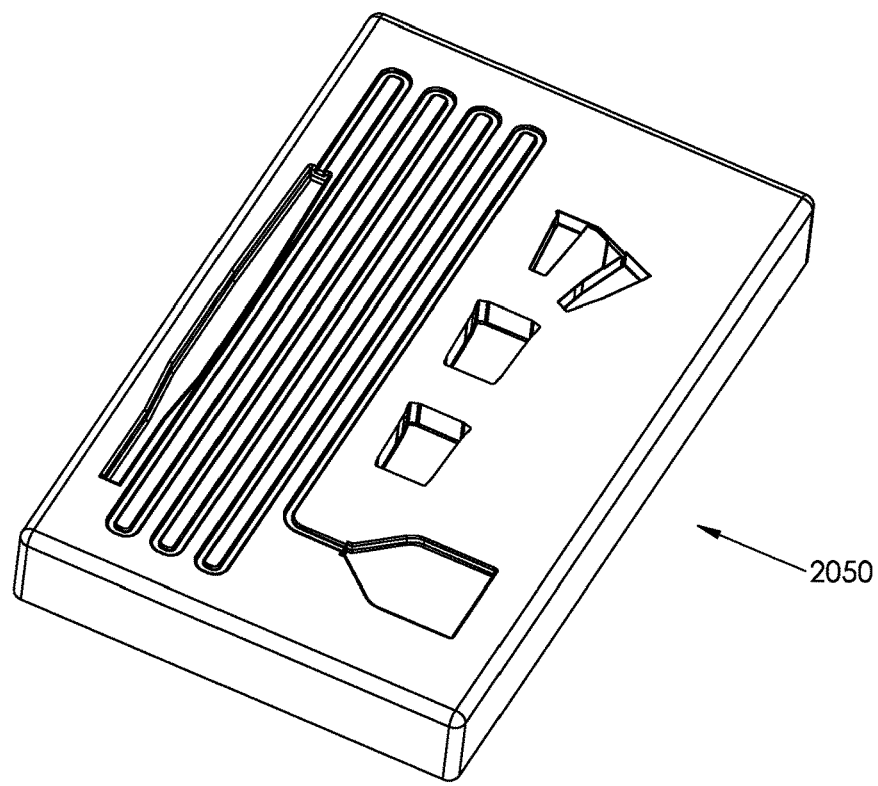
Figure 8B:
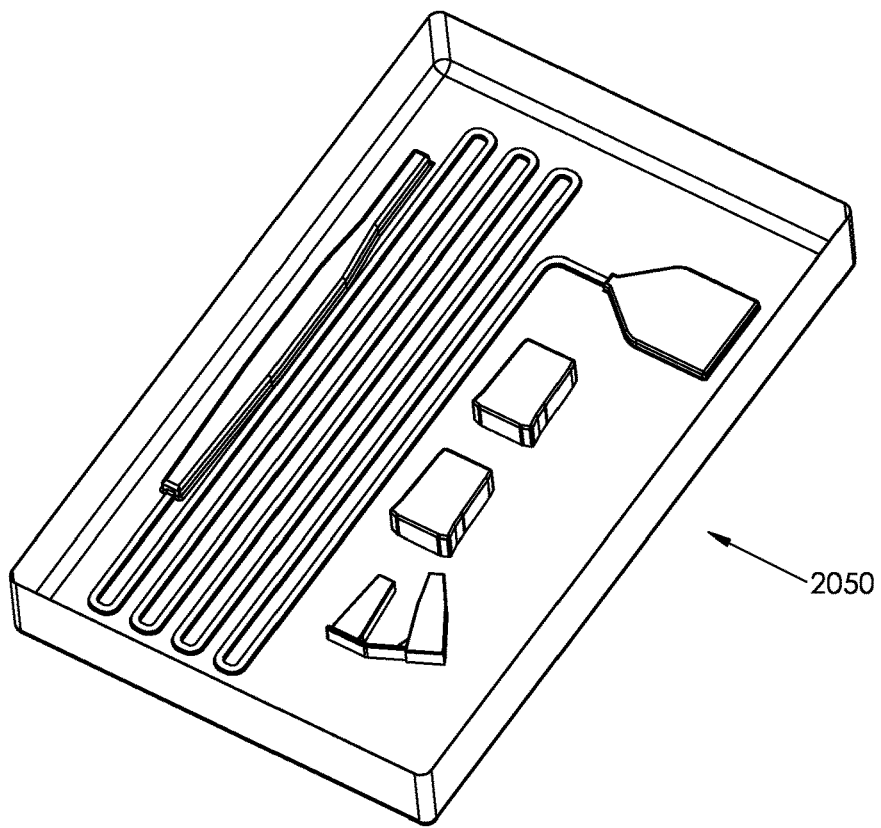
Figure 7C:
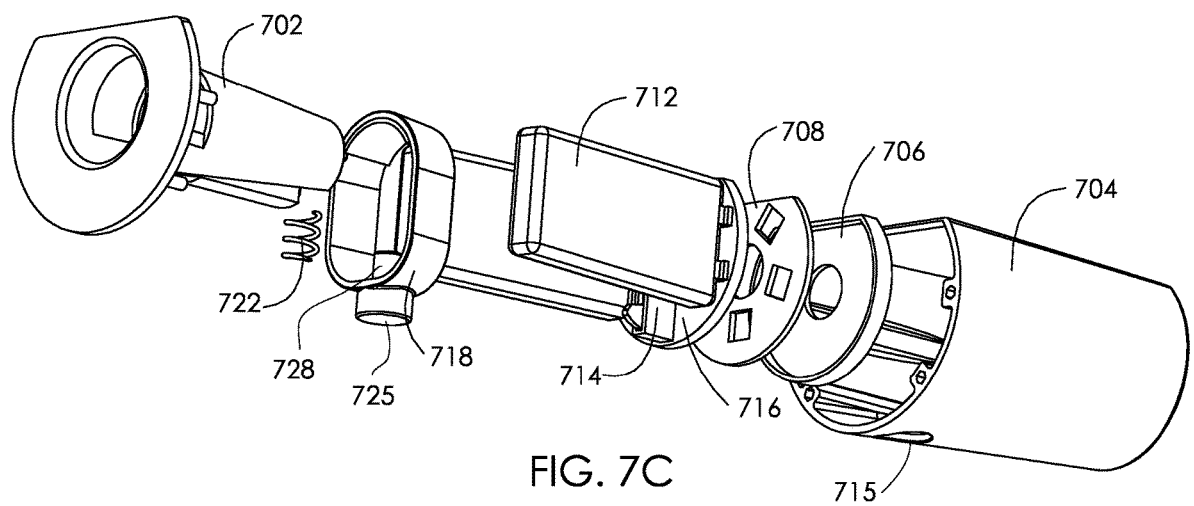
Figure 8C:
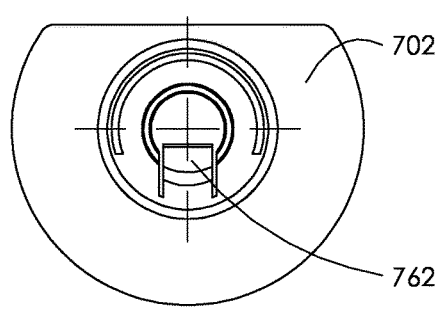
Figure 9C:
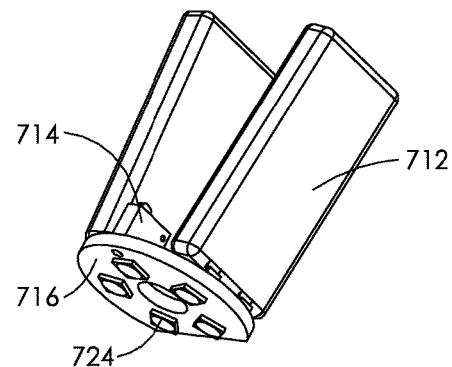

As best seen in FIGS. 9A and 10A, the inner reception bore 1032 has a chamfered leading edge 1034 for easier insertion of the instrument 10 and lighting device 1020 into the holster 1030. The holster body 1028 also includes an upper retention flange 1035 adapted and configured to accommodate a strap or tether so the holster 1030 can be supported on or attached to a surgical drape or the like.

Referring to FIGS. 17A through 33A, there is illustrated another embodiment of a system for performing a surgical procedure which includes a battery powered lighting device 1040 configured for attachment on the distal end portion of a handheld surgical instrument 10 and an elongated holster 1050 for accommodating the surgical instrument 10 with the lighting device 1040 attached thereto.

In this embodiment, the lighting device 1040 is substantially similar to the lighting device 102 shown in FIGS. 11A-16A, in that it includes right and left body portions 1052 and 1052' housing an inner body portion 1008 and having a proximal end cap 1004 and an engagement ring 1006. A PCB 1024 is located within the distal end of the body 1052, 1052' and it has LED light sources 1018 on a front surface thereof and a primary switch 1022 is positioned on the rear surface thereof for activating the LED light sources 1018 upon insertion of the surgical instrument 10 into the lighting device 1040. A plurality of battery cells 1026 are also associated with the rear surface of the PCB 1024 for powering the LED light sources 1018, and a lens 1014 is located in front of the LED light sources 1018, as best seen in FIGS. 31A through 33A.

Figure 28:
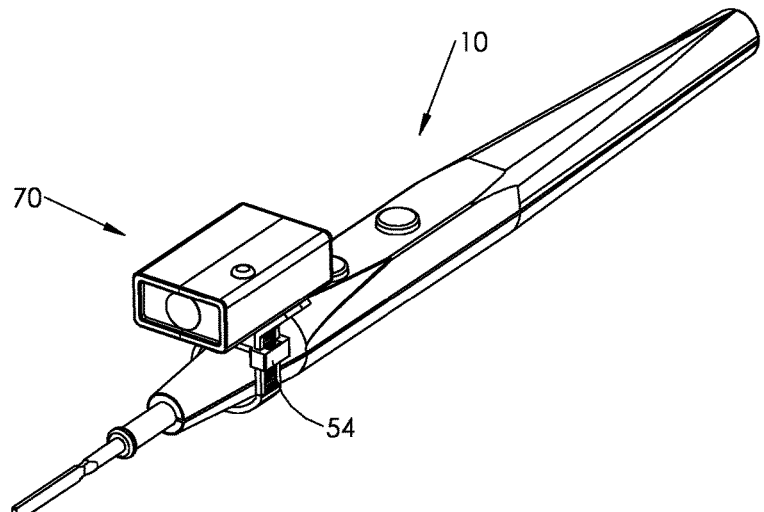
FIGS. 28 through 36 illustrate yet another embodiment of a lighting device which includes a cable-tie type strip for attachment to a handheld surgical instrument.
Figure 28A:
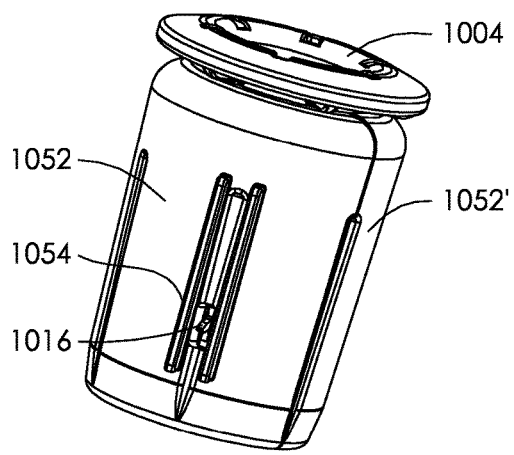
Figure 29A:
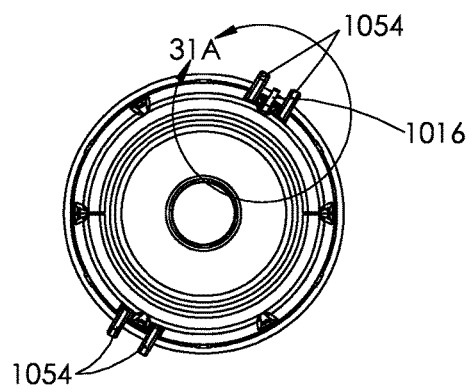
Figure 28C:
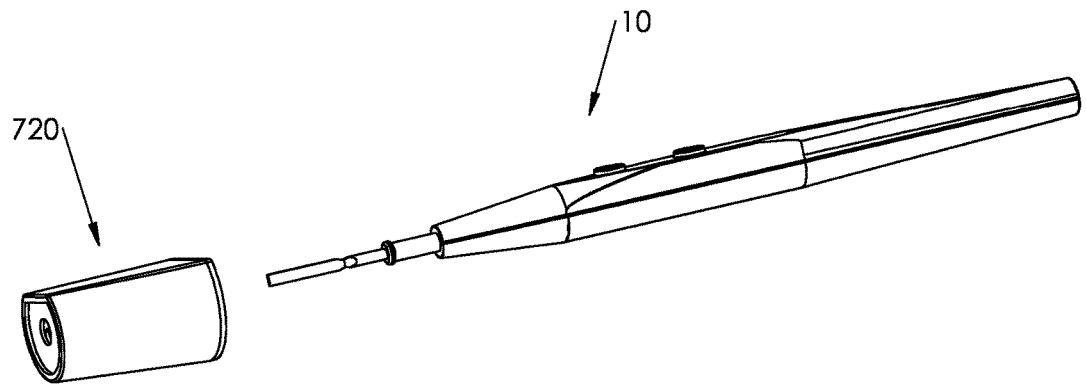
Figure 29C:
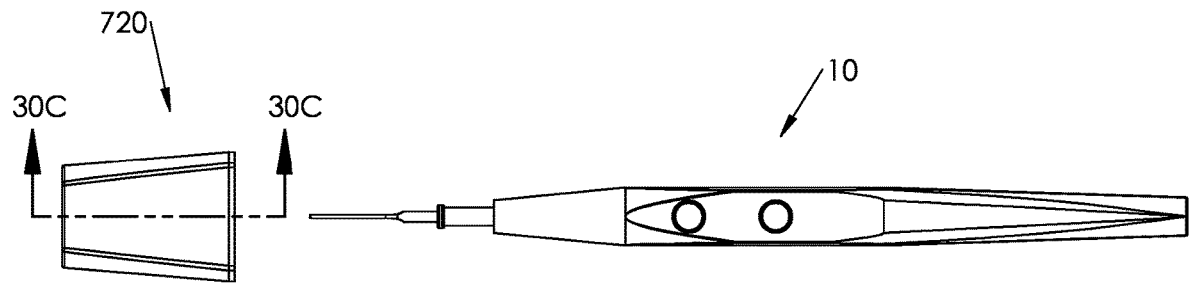

In this embodiment of the invention, the second switch 1016 for controlling the LED light sources 1018 is located in an exterior channel formed between two spaced apart guiding ribs 1054 that project radially outwardly from the outer surface of the body portion 1052, as best seen in FIGS. 19A and 28A. As shown in FIG. 29A, a second set of guiding ribs 1054 is associated with the body portion 1052' for guidance purposes with respect to the holster 1050.

More particularly, as shown in FIGS. 20A through 22A, when the surgical instrument 10 and lighting device 1040 are inserted into the interior of holster body 1056, an interior rib structure 1058 aligns with and slides between the guiding ribs 1054 of body portion 1052 to interact with the switch 1016 located therebetween to turn off the LED light sources 1018 on PCB 1024. At the same time, the guiding ribs 1054 of body portion 1052' align with the channel formed between the opposed rib structures 1058, which is shown in FIGS. 23A through 27A.

As best seen in FIG. 26A, the inner holster body 1056 also has a chamfered leading edge for easier insertion of the instrument 10 and lighting device 1040 into the holster 1050. The holster body 1056 also includes an upper retention flange 1055 adapted and configured to accommodate a strap or tether so the holster 1050 can be supported on or attached to a surgical drape or the like.

The subject invention is also directed to a series of different kits for use in a surgical procedure. In one of these kits illustrated in FIGS. 1B through 4B, there is a preformed package 2030 that contains a handheld electrosurgical instrument 10 and a battery powered lighting device 2020. In another embodiment of the kit shown in FIGS. 5B through 8B, there is a preformed package 2050 that contains a handheld electrosurgical instrument 10, two battery powered lighting devices 2020 and an adapter 2040 for mounting a lighting device 2020 on the surgical instrument 2020.

Here, the lighting device 2020 could have has an interior switch for turning the lighting device on when it is attached to the adapter 2040. FIGS. 9B through 12B, illustrate a kit that includes a preformed package 2060 which only contains a battery powered lighting device 2020 and an adapter 2040 for mounting the lighting device 2020 on a surgical instrument.

Referring to FIGS. 13B through 16B, there is illustrated another embodiment of a kit that includes a preformed package 2080 containing a handheld electrosurgical instrument 10, a battery powered lighting device 2020 and a holster 2070 for receiving the instrument 10 with the lighting device 2020 attached thereto. Referring now to FIGS. 17B through 20B, there is illustrated yet another embodiment of a kit that includes a preformed package 2090 containing a handheld electrosurgical instrument 10, a battery powered lighting device 2020, a holster 2070 and one or more sets of a surgical matrix material 2110 for use during the surgical procedure. The matrix material can be selected form a group of from brands such as: Alloderm, Allomax, FlexHD. These matrix materials are used often in breast reconstruction and other plastic surgeries. Thus, the kit in FIGS. 17B through 20 would enable a breast reconstruction procedure.

Turning now to FIGS. 1C through 14C, the subject invention is also directed to a lighting device 700 for attachment to a handheld surgical instrument 10 that includes an elongated outer housing 704 having opposed proximal and distal ends and an inner body 702 disposed within the outer housing 704 and defining an elongated interior cavity having a proximal opening for receiving a distal end portion of the surgical instrument 10. The housing 704 of lighting device 700 is of the type described above that includes a frusto-conical configuration with a trapezoidal shaped planar upper surface to provide an unobstructed line of sight for a surgeon.

As best seen in FIGS. 7C through 9C, a PCB 716 is positioned at the distal end of the housing 704 of lighting device 700, and a plurality of LED light sources 724 are embedded in the front surface of the PCB 716. One or more of these LED light sources 724 can provide light in a UV spectrum range to promote benefits such as a reduction in bacteria at the surgical site. A cover 708 is associated with the front surface of PCB 716 to protect the LED light sources 724 and a lens 706 is positioned in front of the cover 708 to direct the light from the LED light sources 724. A plurality of battery cells 712 are associated with the rear surface of PCB 716 for powering the LED light sources 724, and a mechanical switch 714 is also associated with the rear surface of the PCB 716 for activating the LED light sources upon the insertion of the distal end portion of surgical instrument 10 into the interior cavity of the inner body 702, as explained in detail below.

Figure 10C:
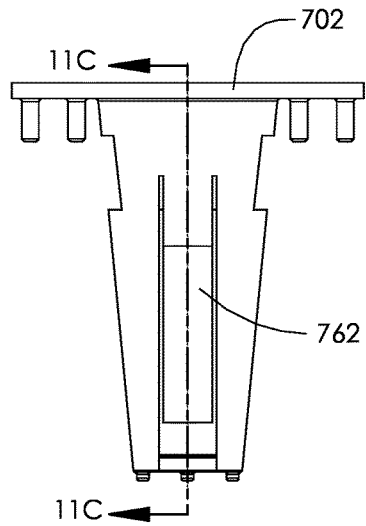
Figure 11C:
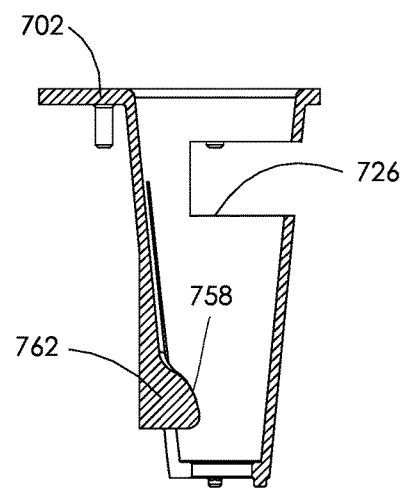

As best seen in FIGS. 10C and 11C, a deflectable contact leg 762 is formed integral with the inner body 702. The contact leg 762 is configured in a cantilevered manner to contact the switch 714 on PCB 716 upon the insertion of the distal end portion of the surgical instrument 10 into the interior cavity of the inner body 702 to mechanically activate the LED light source 724. The contact leg 762 includes a radially inwardly projecting foot 758 at a distal end thereof that forms a ramped camming surface for easing the insertion of the distal end portion of the surgical instrument 10 into the interior cavity of the inner body 702.

The lighting device 700 further includes a spring biased engagement ring 718 that is disposed within the outer housing 704. The engagement ring 718 is mounted for movement relative to the inner body 702 and the outer housing 704 between an axially aligned position shown in FIG. 6C, where it accommodates the easy insertion of the distal end portion of the surgical instrument 10 into the interior cavity of the inner body 702, and a slightly off-centered position shown in FIG. 3C, where it is normally at rest within the lighting device 700.

Figure 6C:
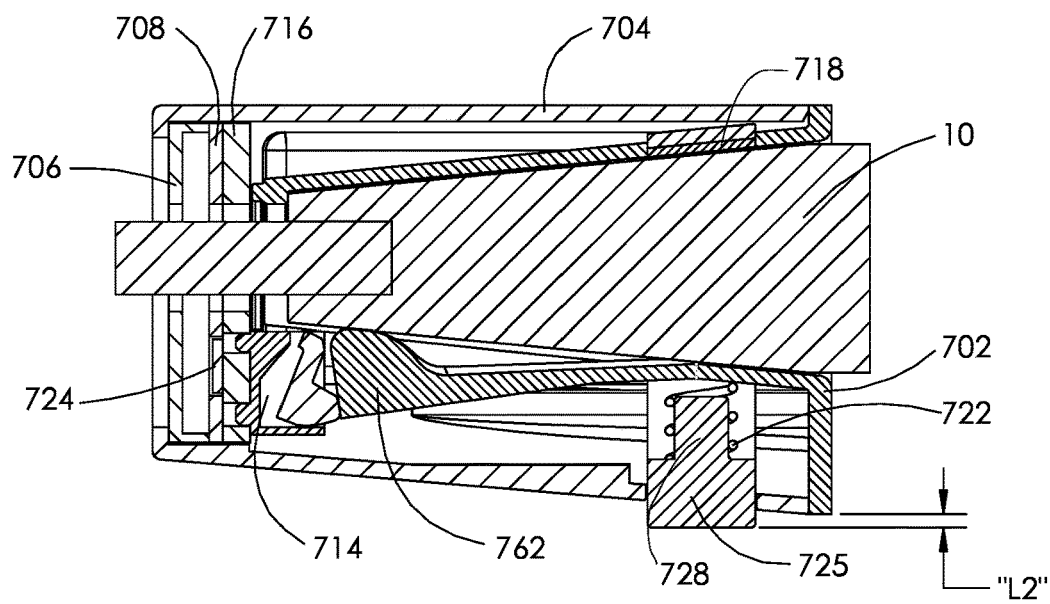
Figure 5B:
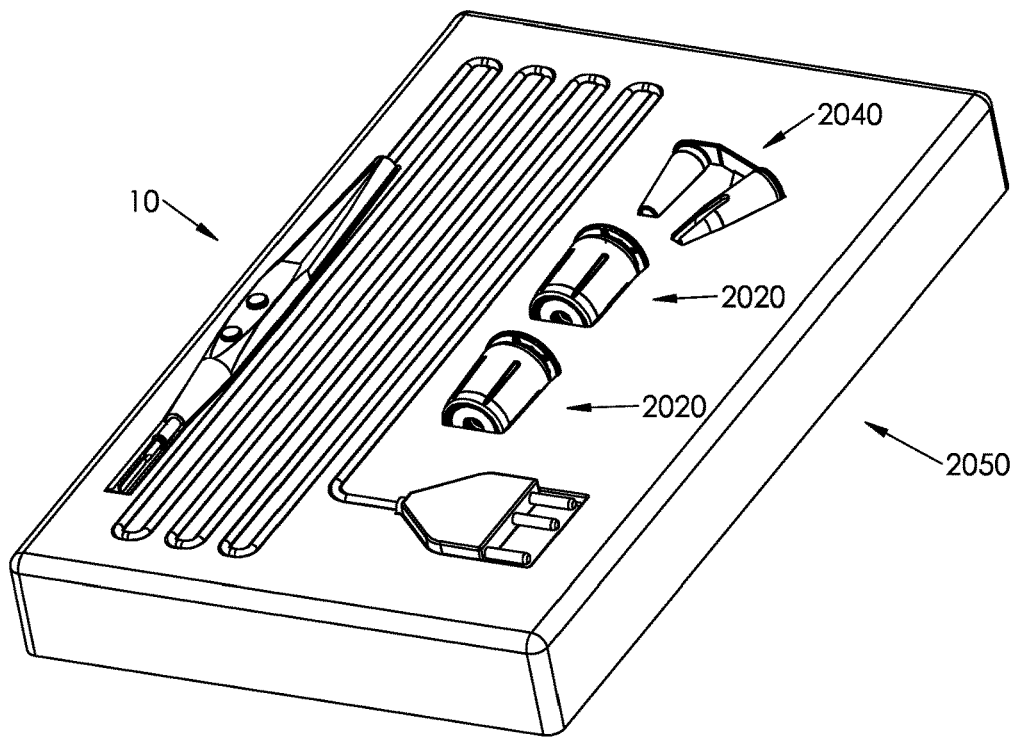
Figure 6B:
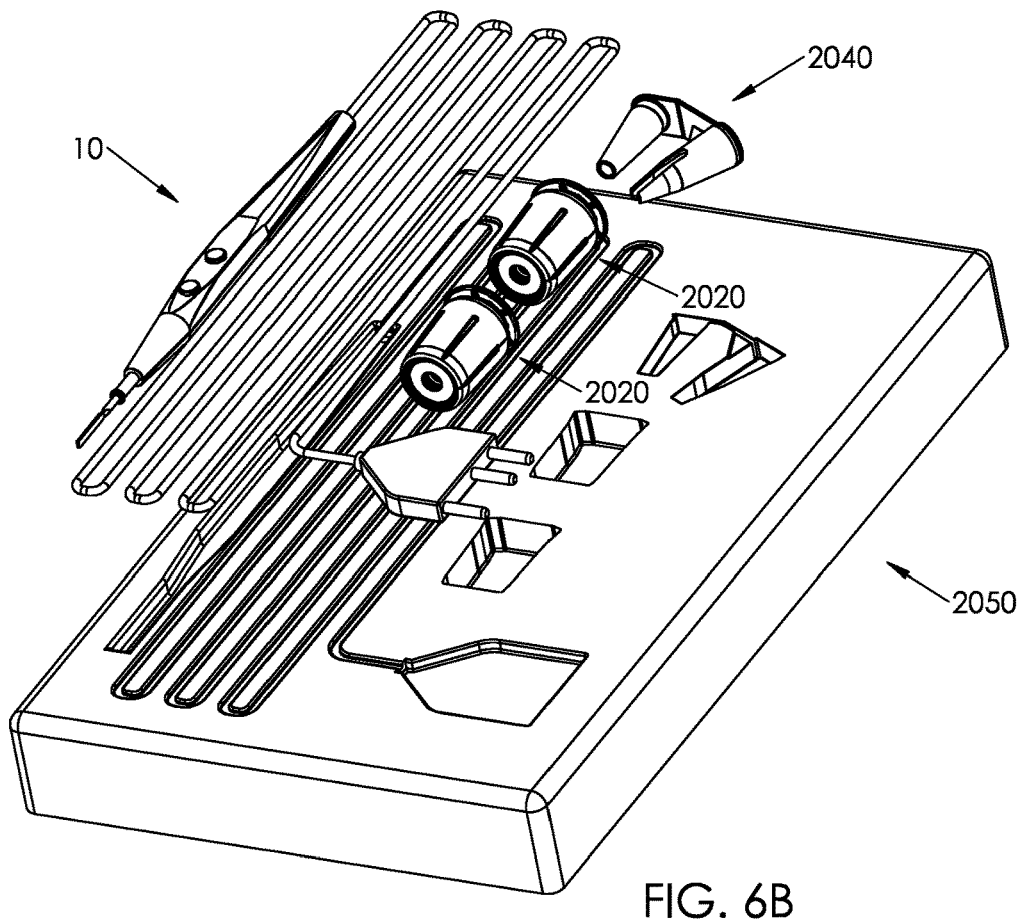
Figure 7A:
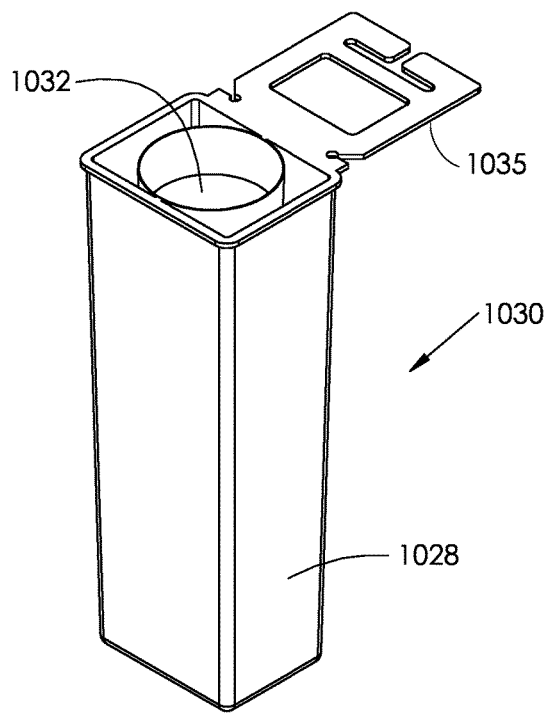
Figure 8A:
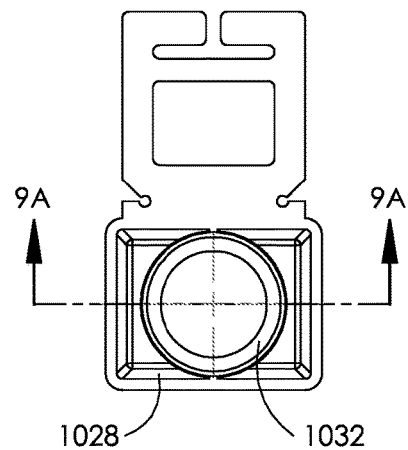

When the surgical instrument 10 is inserted into the lighting device 700, as shown in FIG. 6C, the mechanical retention of the distal end portion of the surgical instrument 10 by the engagement ring 718 is effectuated by the inner peripheral surface section 732 of the engagement ring 718. More particularly, surface section 732 has a compliant retention material thereon (e.g. a rubber or silicone material) that resiliently or adhesively retains the distal end portion of the surgical instrument 10, as illustrated in FIG. 6C. This retention material may be adhesively attached to the inner peripheral surface of the engagement ring 718 or it may be over-molded onto the engagement ring 718.

The inner body 702 of lighting device 700 includes an arcuate slot 726 for accommodating the engagement ring 718 within the outer housing 704, which is best seen in FIG. 11C. In use, when the engagement ring 718 is manually moved within the arcuate slot 726 from the axially off-centered position shown in FIG. 3C to the axially aligned position shown in FIG. 6C. This movement can be seen by comparing the distances L1 and L2 in FIGS. 3C and 6C, respectively.

Figure 3C:
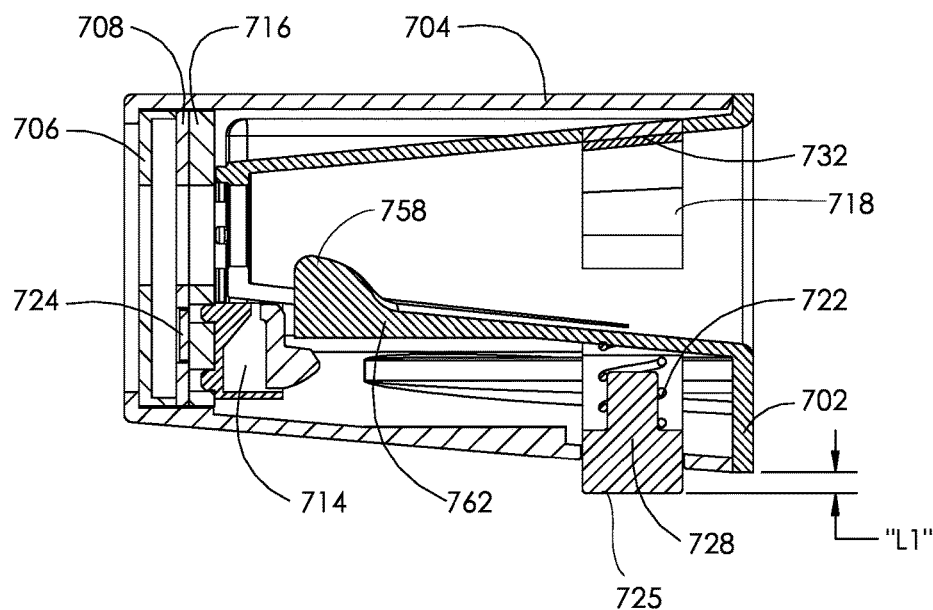
Figure 3B:
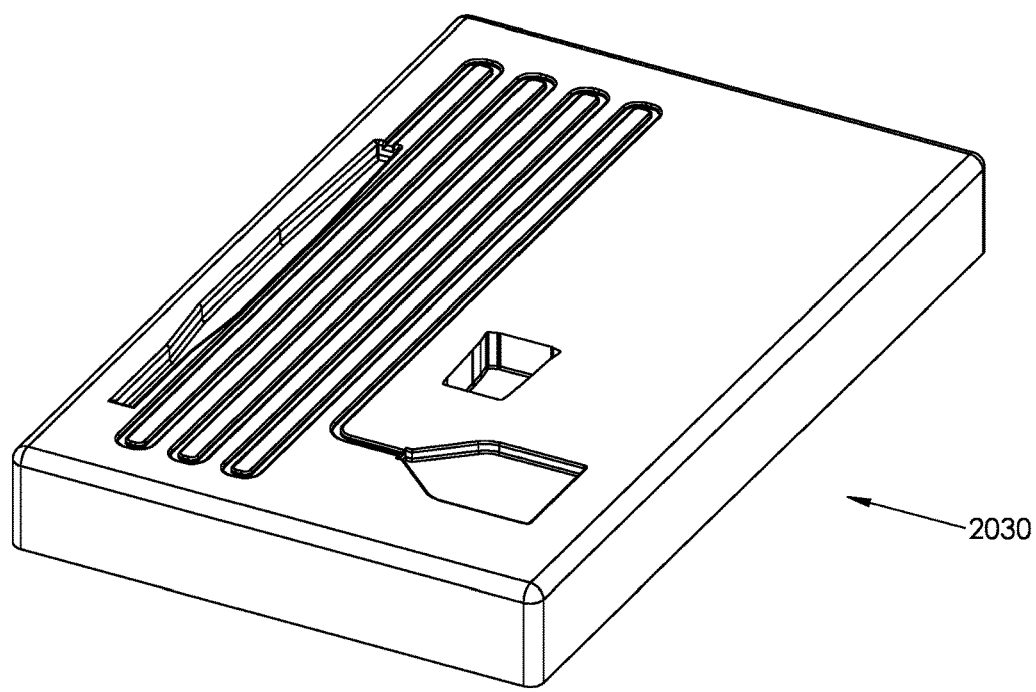
Figure 4B:
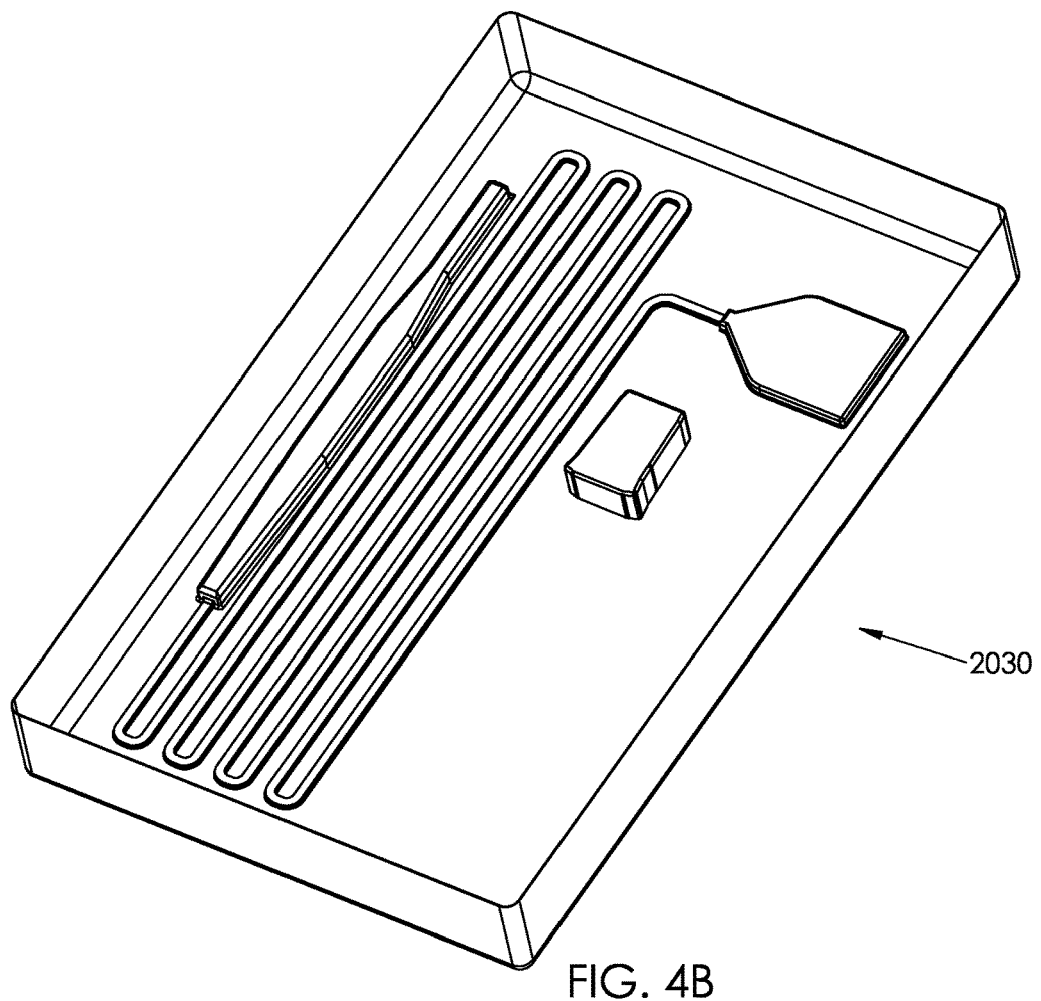
Figure 4:
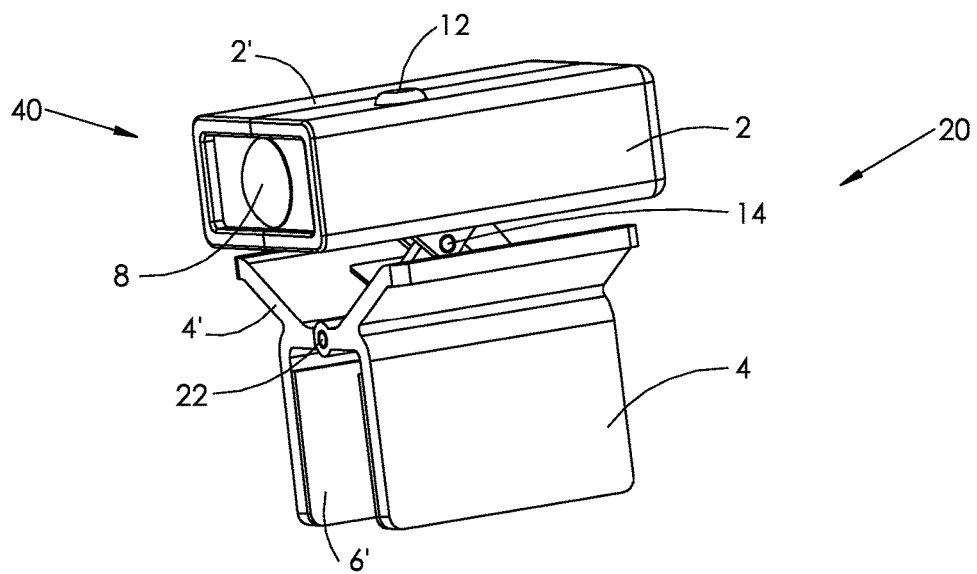

As best seen in FIGS. 12C through 14C, a projection or button 725 extends radially outwardly from the engagement ring 718, through an access port 715 in the outer housing 704 of lighting device 700 for manually moving the engagement ring 718 from the off-centered position of FIG. 3C to the centered position of FIG. 6C. More particularly, a coiled spring 722 is supported on a post 728 that extends radially inwardly from the inner peripheral surface of engagement ring 718.

Thus, the coiled spring 722 is positioned between an inner periphery of the engagement ring 718 and an exterior surface of the inner body 702. Here, the coiled spring 722 provides a spring force against the manual movement of the engagement ring 718 from the off-centered position of FIG. 3C to the centered or aligned position of FIG. 6C. In other words, the coiled spring 722 biases the engagement ring 718 into the normal resting position of FIG. 3C.

Referring to FIGS. 15C through 27C, there is illustrated another embodiment of the lighting device of the subject invention, which is designated generally by reference numeral 710. Lighting device 710 is substantially similar to the lighting device 700 illustrated in FIGS. 1C through 14C, but in this embodiment of the lighting device the engagement ring that retains the distal end portion of the surgical instrument 10 operates differently. Here, the engagement ring, which is designated generally by reference numeral 754 is normally biased into a resting position by a leaf spring 756 instead of the coiled spring 722 shown in FIG. 7C. The leaf spring 756, which is best seen in FIGS. 26C and 27C, is secured in a slot 764 formed on an exterior surface of the inner body 752 of lighting device 710. In this position, it is located between an outer periphery of the engagement ring 754 an interior surface of the outer housing 704.

Figure 20:
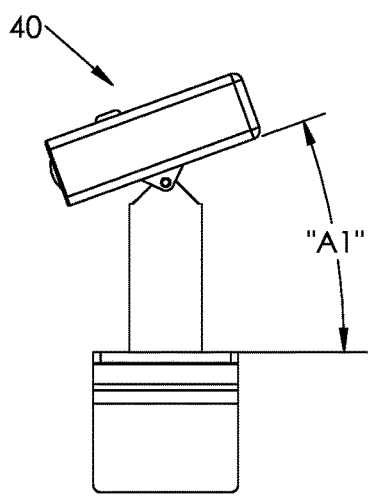
Figure 20C:
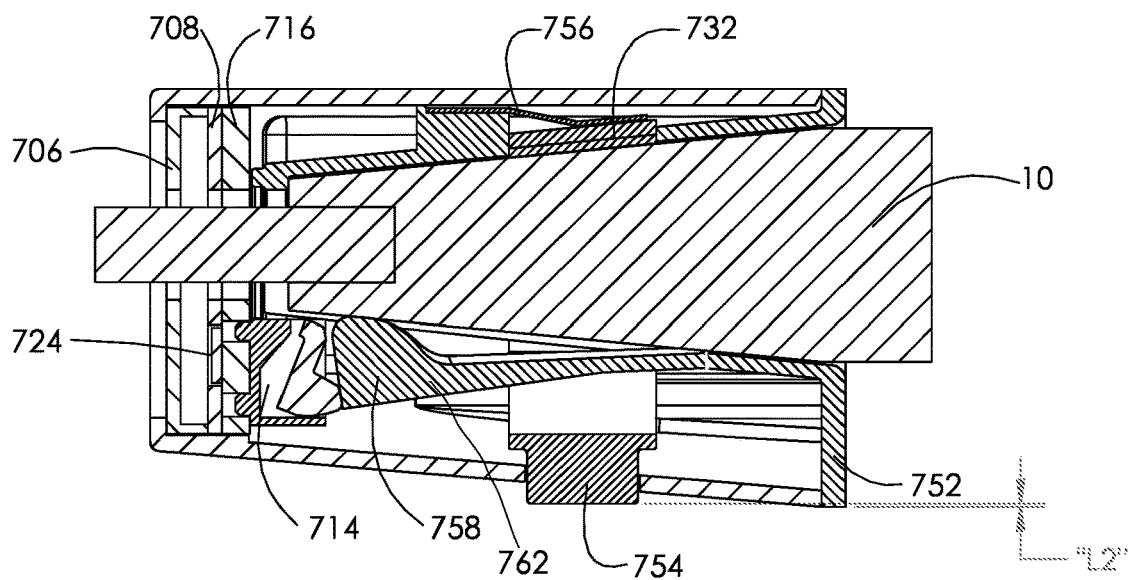
Figure 19B:
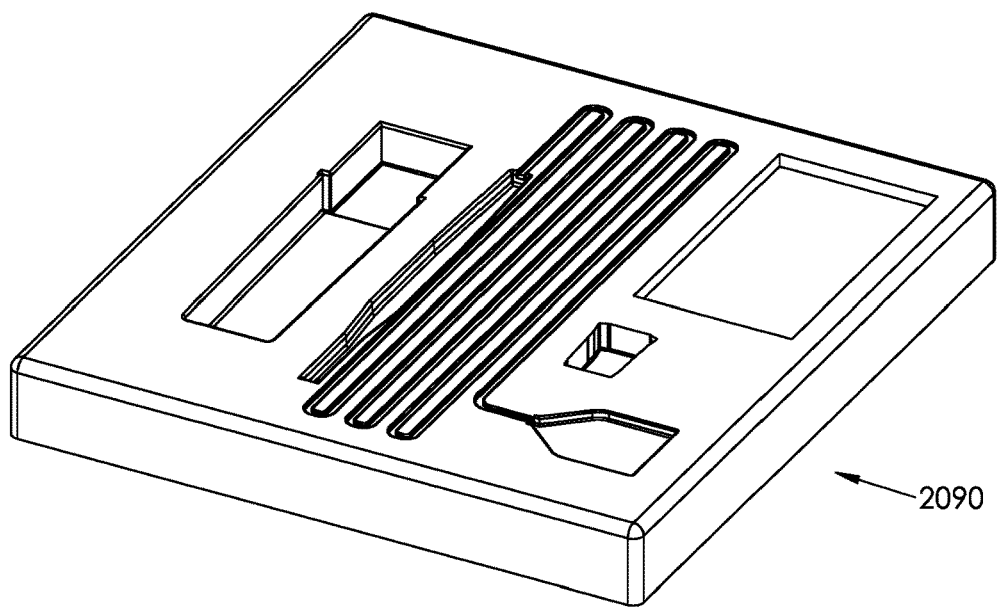
Figure 20B:
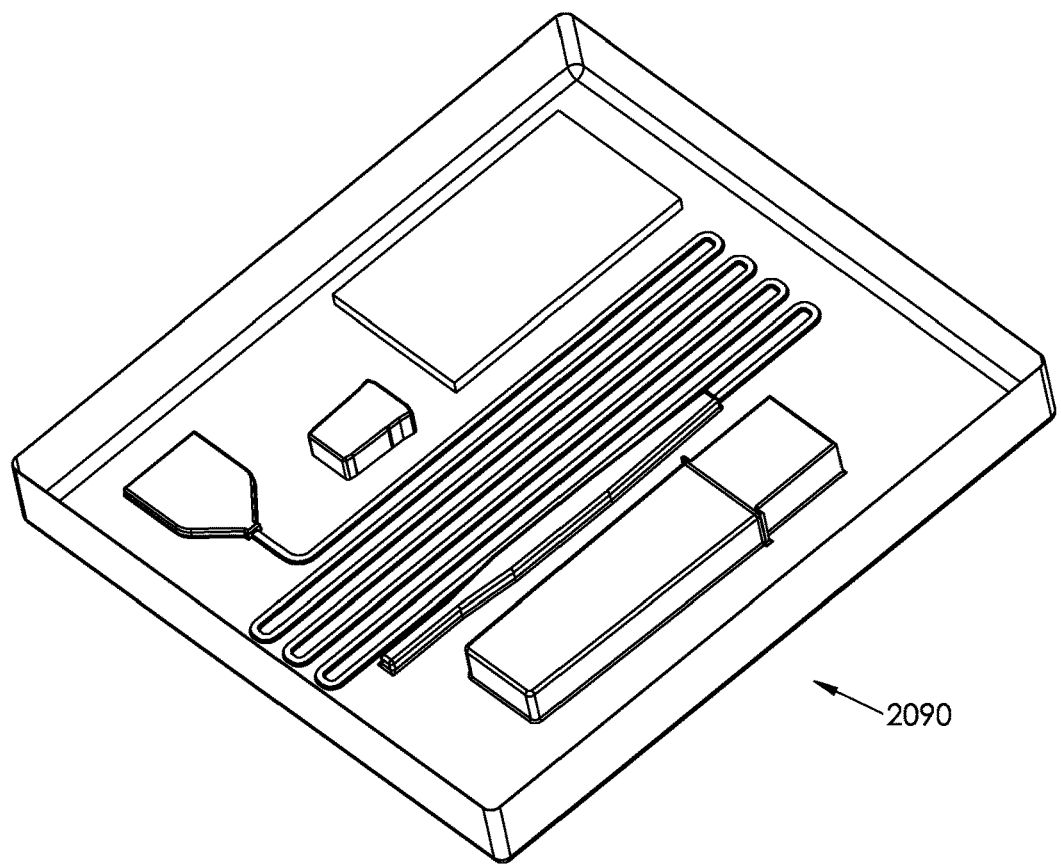
Figure 20A:
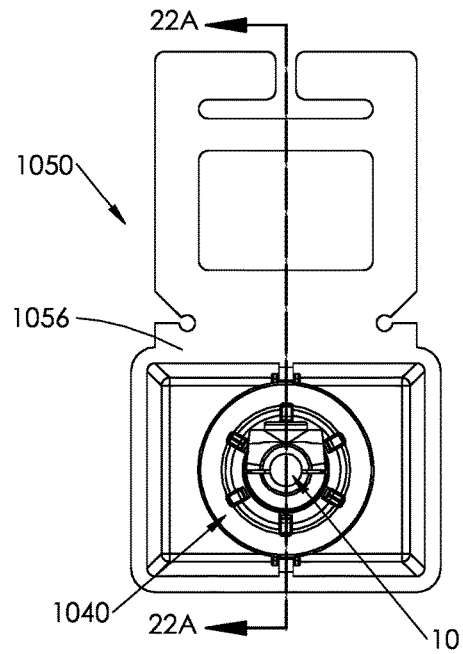
Figure 21A:
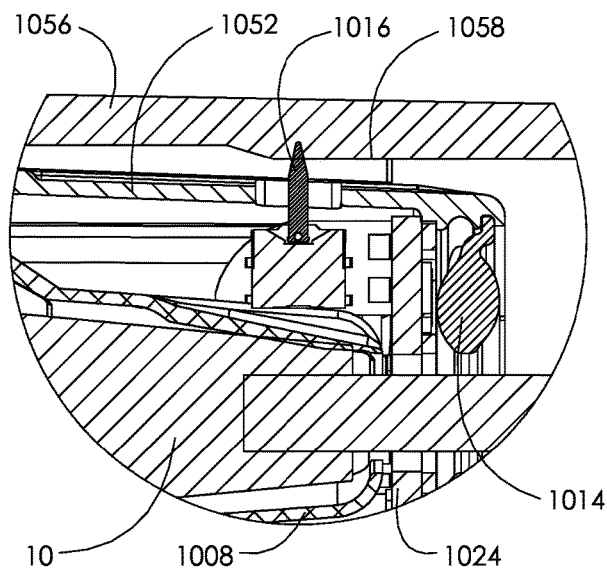
Figure 22A:
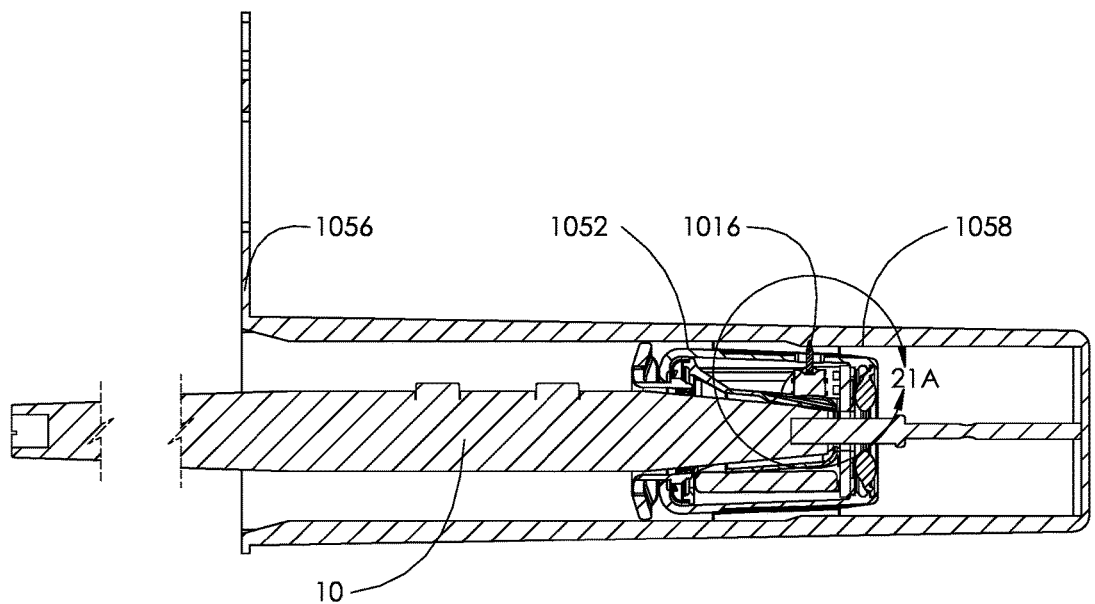
FIGS. 22 through 25 illustrate another embodiment of a lighting device of the subject invention which includes a flexible hook and loop type fastening strip for attachment to a handheld surgical instrument.
Figure 21C:
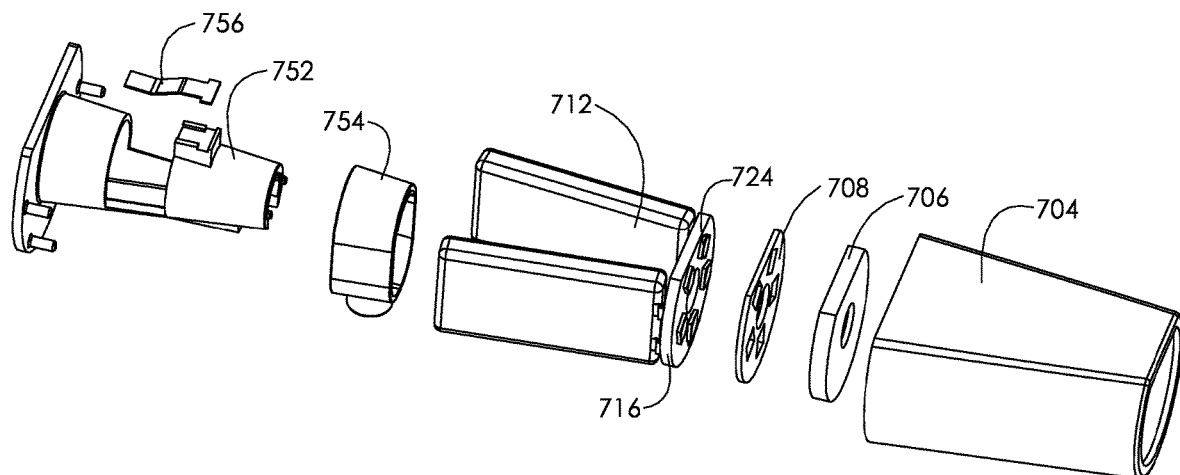
Figure 22C:
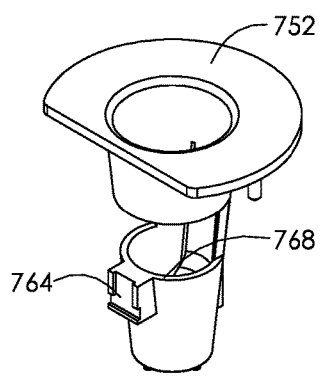
Figure 23C:
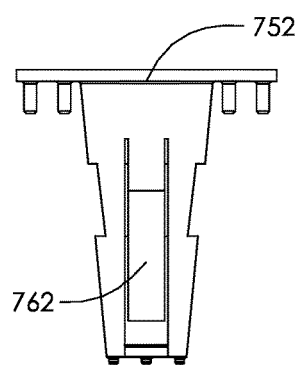
Figure 24C:
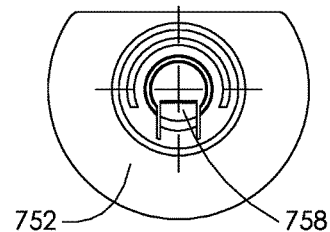
Figure 25C:
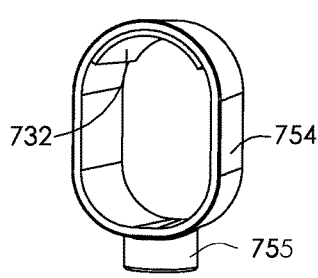

In use, when the actuation button 725 on engagement ring 754 is manually depressed, the engagement ring 754 moves within the arcuate slot 768 formed in the inner body 752 against the biasing force of leaf spring 756. In doing so, the engagement ring 754 moves from a normally off-centered position shown in FIG. 17C to an axially aligned or centered position shown in FIG. 20C where it accommodates the easy insertion of the distal end portion of the surgical instrument 10 into the lighting device 710. This movement can be seen by comparing the distances L1 and L2 in FIGS. 17C and 20C, respectively.

Referring now to FIGS. 28C through 40C, there is illustrated yet another embodiment of a lighting device constructed in accordance with the subject invention which is designated generally by reference numeral 720. Lighting device 720 includes a one-piece frusto-conical shaped outer housing 804 with a planar upper surface and an inner body portion 802 for receiving and accommodating the distal end portion of a surgical instrument 10.

Figure 34:
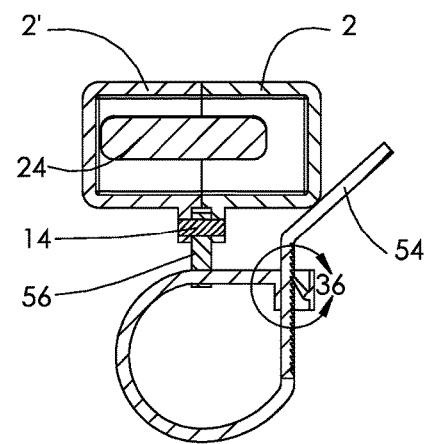
Figure 34C:
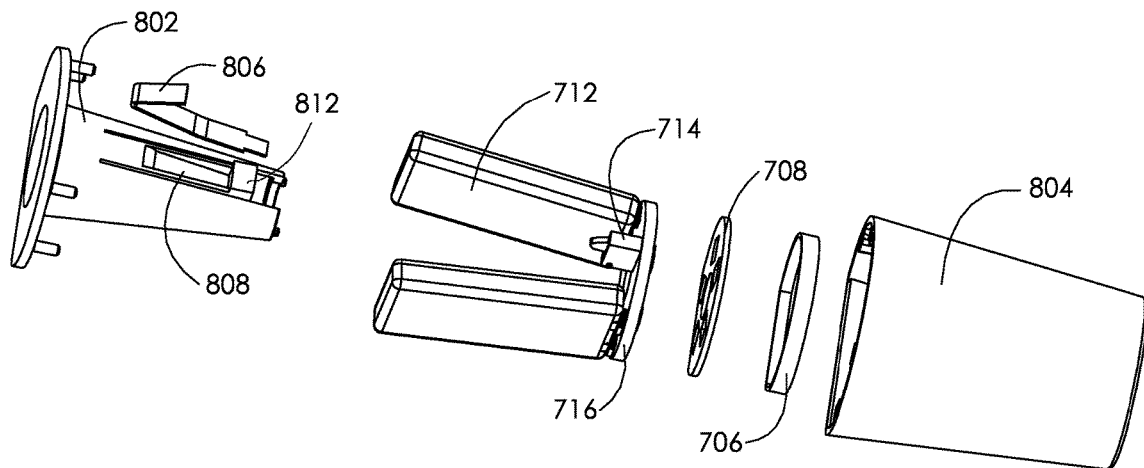
Figure 35C:
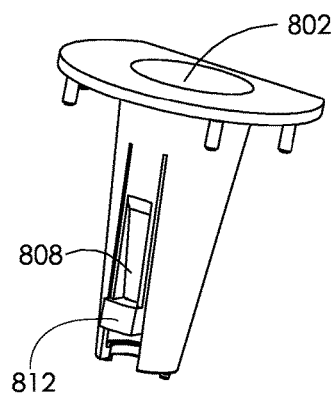
Figure 36C:
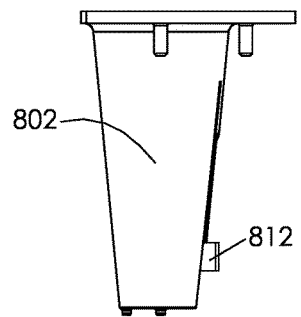
Figure 37C:
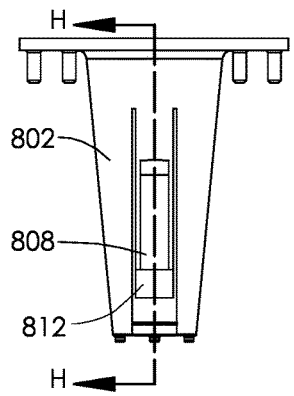
FIGS. 37 and 38 are perspective views of a light assembly of the subject invention associated with a suction/irrigation instrument.
Figure 38C:
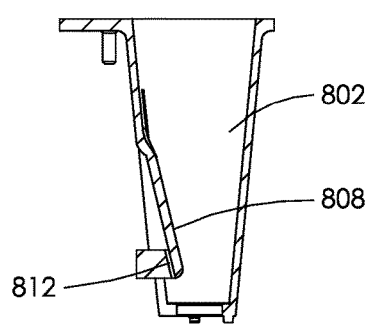

As best seen in FIG. 34C, a PCB 716 is positioned at the distal end of the outer housing 804 of lighting device 720, and a plurality of LED light sources 724 are embedded in the front surface of the PCB 716. One or more of these LED light sources 724 can provide light in a UV spectrum range. A cover 708 is associated with the front surface of PCB 716 to protect the LED light sources 724 and a lens 706 is positioned in front of the cover 708 to direct the light from the LED light sources 724. A plurality of battery cells 712 are associated with the rear surface of PCB 716 for powering the LED light sources 724, and a mechanical switch 714 is also associated with the rear surface of the PCB 716 for activating the LED light sources upon the insertion of the distal end portion of surgical instrument 10 into the interior cavity of the inner body portion 802, as explained in detail below.

Figure 30A:
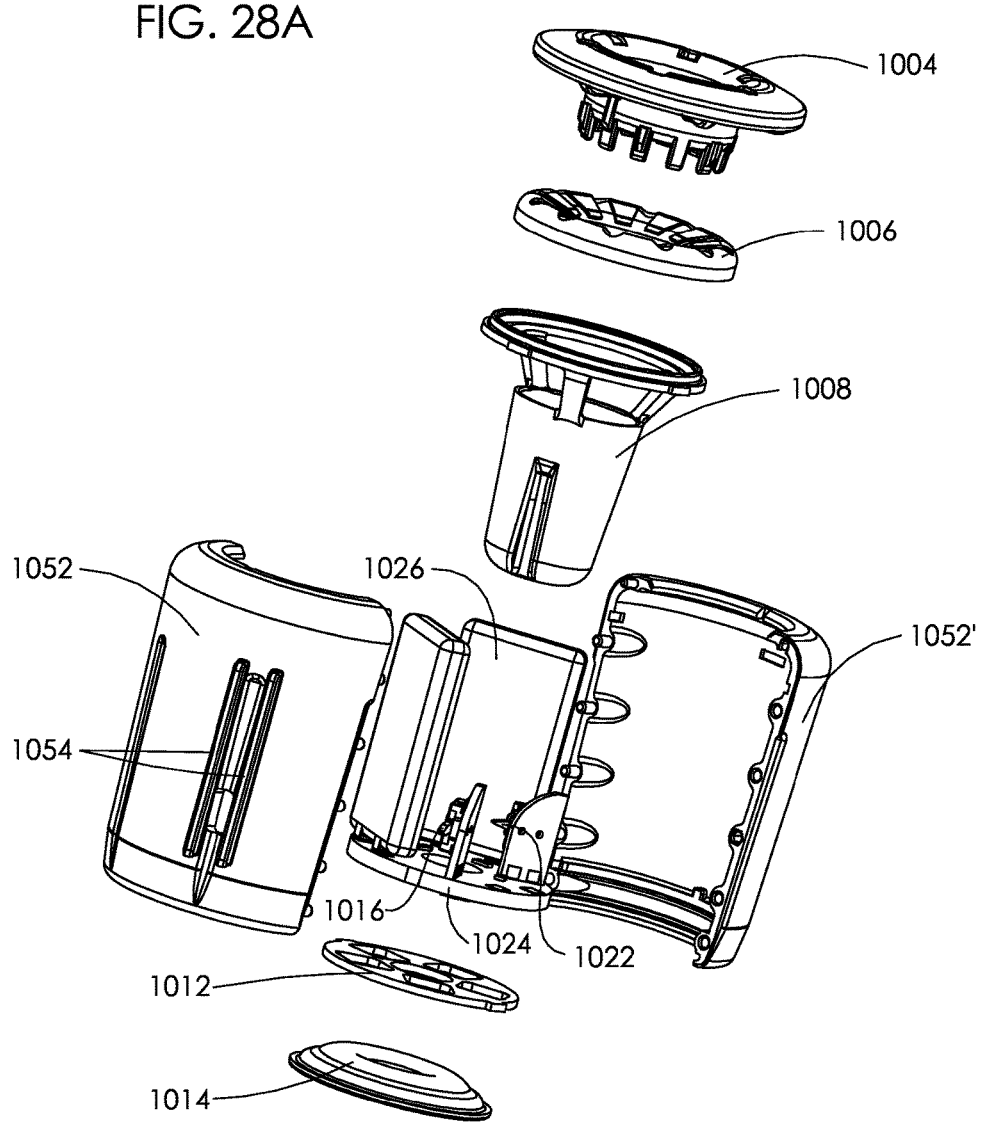
Figure 30C:
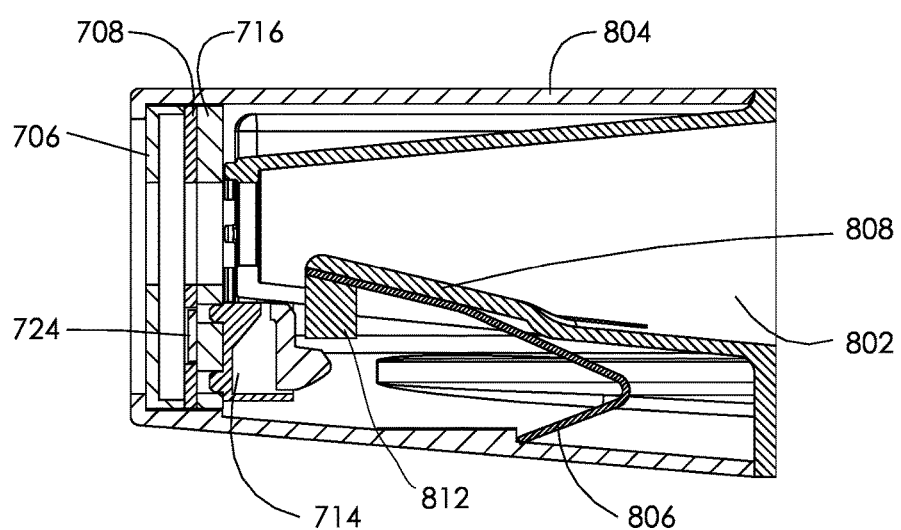
Figure 30:
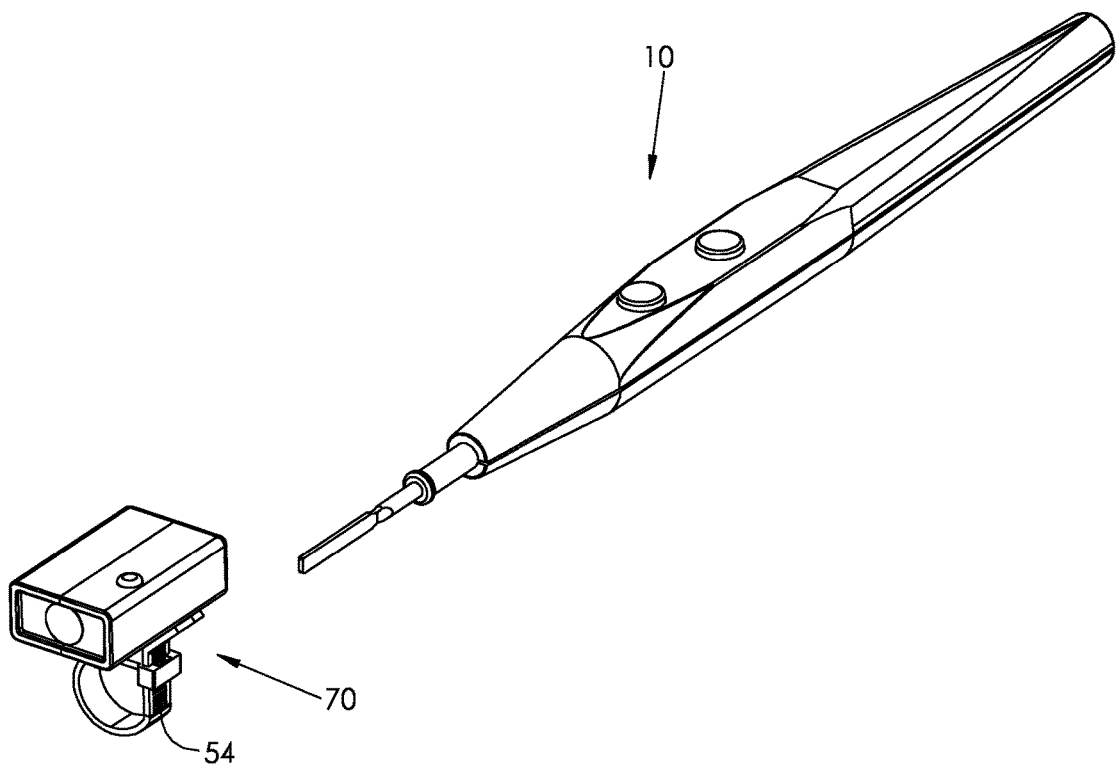
Figure 31:
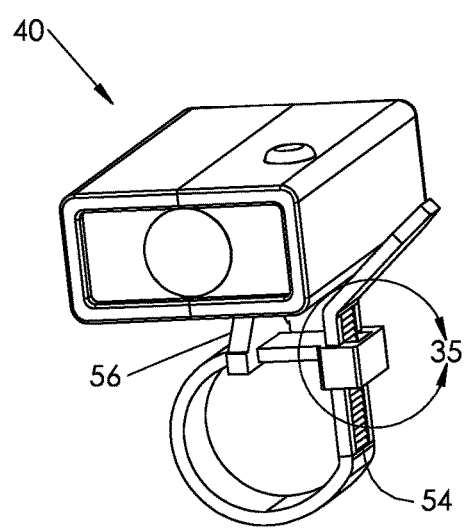
Figure 32:
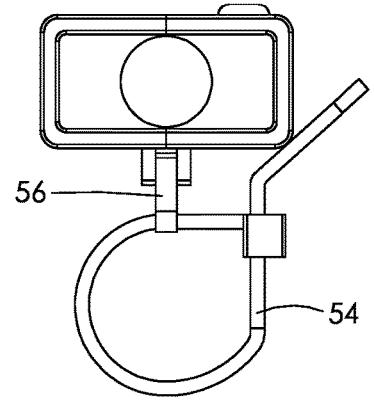
Figure 31A:
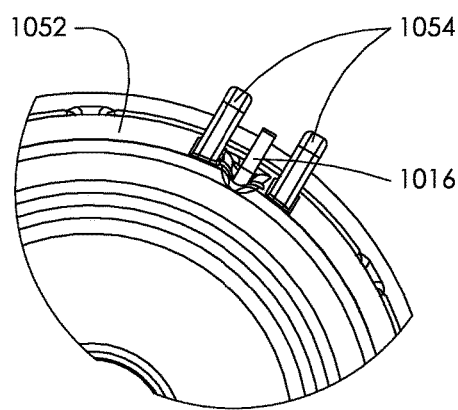
Figure 32A:
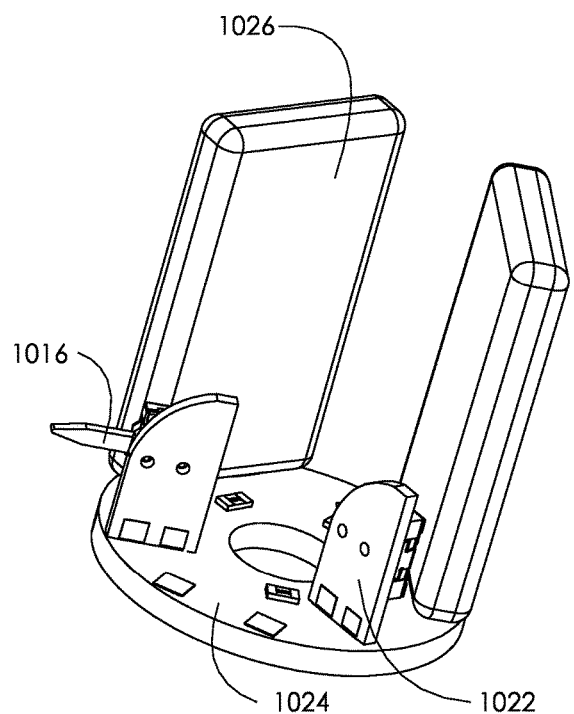
Figure 31C:
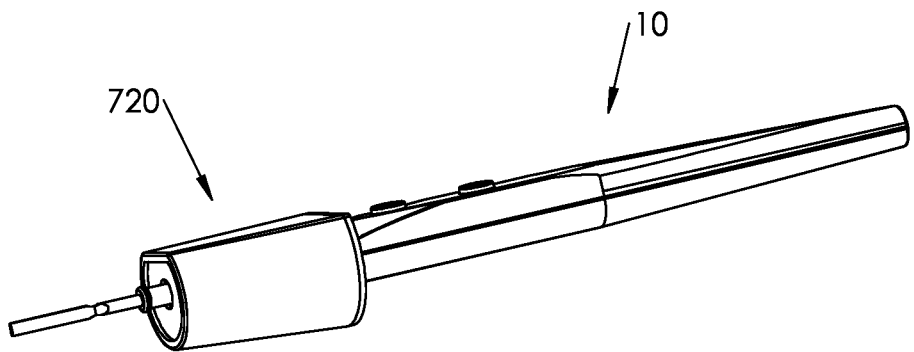
Figure 32C:
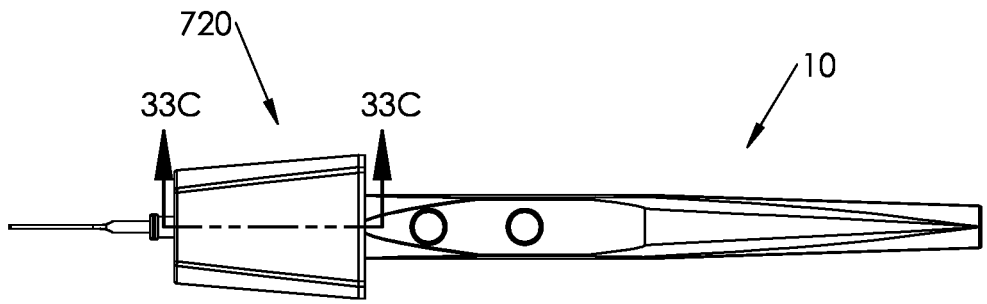
Figure 39C:
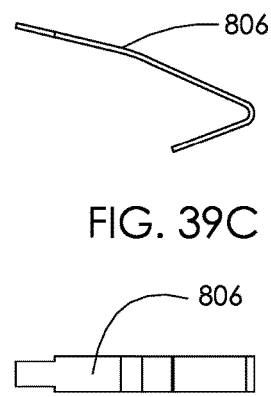
FIGS. 39 through 42 illustrate another embodiment of the lighting device of the subject invention, where distal end portion of the handheld surgical instrument is inserted into the body of the lighting device.
Figure 40C:
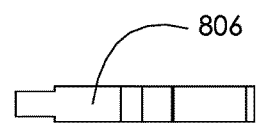

As best seen in FIGS. 35C through 38C, a deflectable contact leg 808 is integrally formed in the inner body portion 802 in a cantilevered manner and it includes a radially outwardly extending foot 812 on a distal end thereof that is configured and located to interact with the switch 714 on PCB 716 upon the insertion of the distal end portion of surgical instrument 10 into lighting device 720. A leaf spring 806, which is best seen in FIGS. 39C and 40C, is located between the bottom surface of the contact leg 808 and the inner surface of outer housing 804. As best seen in FIG. 30C, the leaf spring 806 normally biases the deflectable contact leg 808 in a radially inward direction, so that it projects into the central reception bore of the inner body portion 802 to mechanically interact with the distal end portion of the surgical instrument 10 when it is inserted into lighting device 720.

Figure 33A:
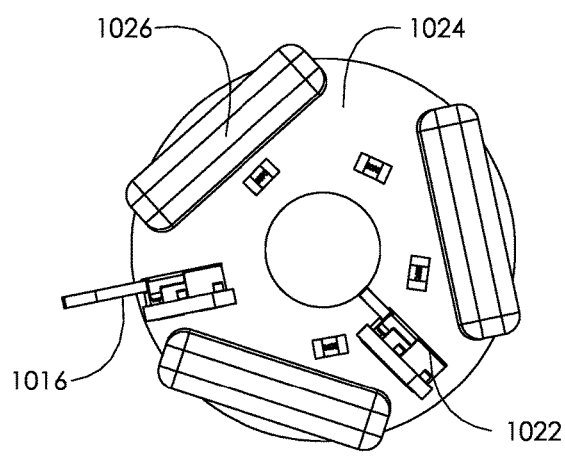
Figure 33C:
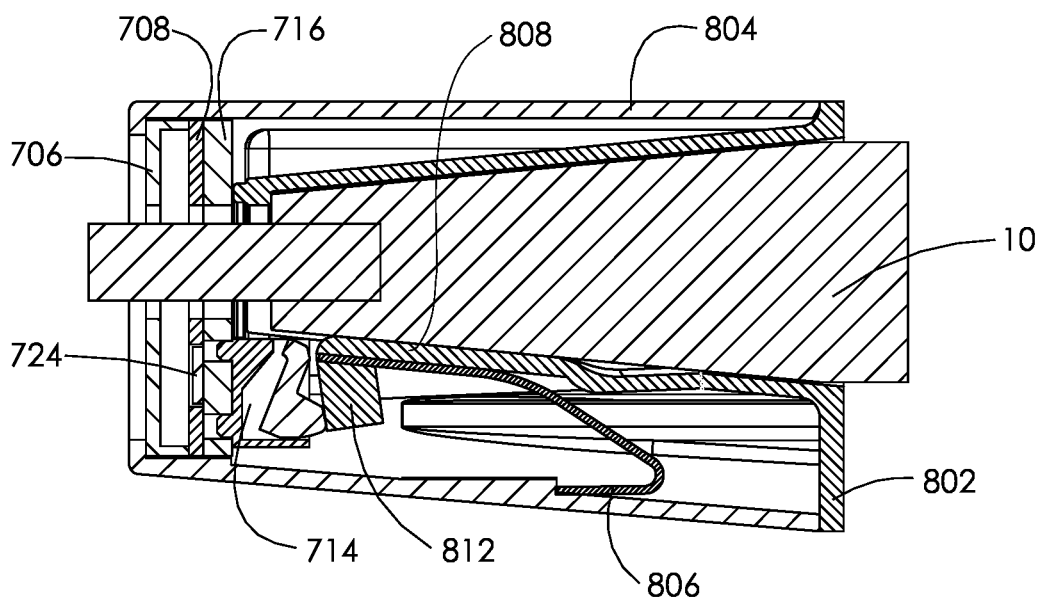
Figure 33:
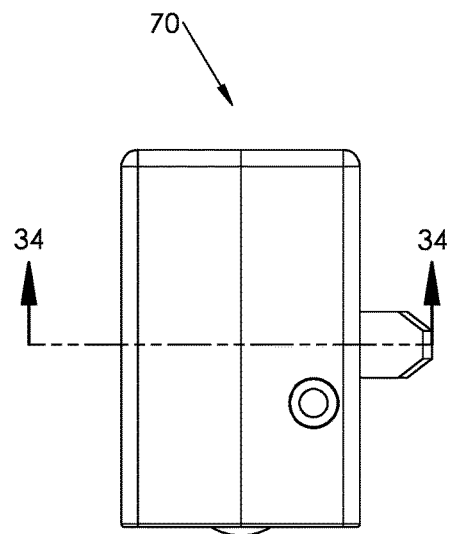
Figure 35:
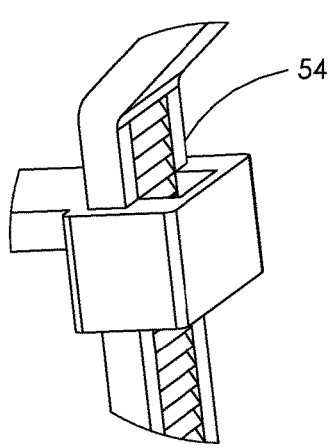
Figure 36:
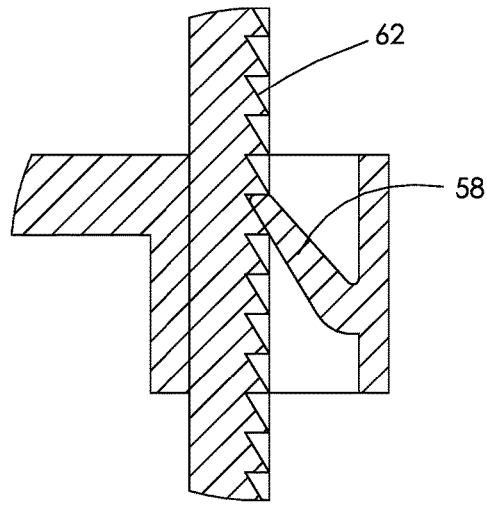

In use, when the distal end portion of the surgical instrument 10 is inserted into the central bore of the inner body portion 802 of lighting device 720, the distal end portion of the instrument will slide along the ramped upper surface of contact leg 808, compressing the leaf spring 806, as shown in FIG. 33C, so that the distal foot 812 of contact leg 808 contacts the switch 714 on PCB 706. As a result, the LED light sources 724 on PCB 706 are activated, powered by the battery cells 712. Upon the withdrawal of the surgical instrument 10 from the inner body 802 of the lighting device 720, the biasing spring 806 will urge the deflectable contact leg 808 back toward the central axis of the inner body 802, so that the distal foot 812 is out of contact with the switch 714, thereby deactivating the LED light sources 724 on PCB 706.

While the subject disclosure has been shown and described with reference to preferred embodiments, those skilled in the art will readily appreciate that changes and/or modifications may be made thereto without departing from the scope of the subject disclosure.

What is claimed is:

1. A lighting device for attachment to a handheld surgical instrument comprising:
   a) an outer body portion having opposed proximal and distal ends, and defining a planar upper surface portion, wherein the outer body portion has a frusto-conical configuration and the upper planar surface portion has a trapezoidal shape;
   b) an inner body portion disposed within the outer body portion and defining an elongated inner cavity having a proximal opening for receiving a distal end portion of the surgical instrument; and
   c) a light source located within the outer body portion for directing light from the distal end thereof.

2. A lighting device as recited in claim 1, wherein the light source is defined by a plurality of LED light sources arranged in spaced relationship on a front surface of a printed circuit board.

3. A lighting device as recited in claim 2, wherein a contact switch is located on a rear surface of the printed circuit board for activating the LED light sources upon insertion of the distal end portion of the surgical instrument.

4. A lighting device as recited in claim 3, wherein a pair of battery cells are operatively associated the rear surface of the printed circuit board for powering the LED light sources.

5. A lighting device as recited in claim 2, wherein a lens is disposed at the distal end of the outer housing portion for focusing the LED light sources.

6. A lighting device as recited in claim 1, wherein a compliant securement ring is disposed in the outer body portion for mechanically engaging and retaining the distal end portion of the surgical instrument.

7. A lighting device as recited in claim 1, wherein a securement screw is located on the planar upper surface portion of the outer body portion and is operatively associated with the inner cavity of the inner body portion for selectively engaging the distal end portion of the surgical instrument.

8. A lighting device as recited in claim 1, wherein an elongated securement beam is pivotably attached to the proximal end of the outer body portion about an axis that extends perpendicular to a longitudinal axis of the surgical instrument and it includes a proximal clasp for frictionally engaging a proximal end portion of the surgical instrument.

9. A lighting device as recited in claim 1, wherein a securement cam arm is rotational attached to a proximal end cap of the outer body portion about an axis that extends parallel to a longitudinal axis of the surgical instrument and it includes a cam surface for frictionally engaging the distal end portion of the surgical instrument and an outer tang for selectively engaging a retaining boss projecting from the proximal end cap.

10. A lighting device for attachment to a handheld surgical instrument comprising:
   a) a substantially frusto-conical outer body portion having opposed proximal and distal ends, and defining a trapezoidal shaped upper planar surface portion;
   b) an inner body portion disposed within the outer body portion and defining an elongated inner cavity having a proximal opening for receiving a distal end portion of the surgical instrument; and c) a battery powered light source located within the outer body portion for directing light from the distal end thereof, wherein the upper planar surface portion of the outer body portion is configured for planar alignment with an upper surface of the surgical instrument.

11. A lighting device as recited in claim 10, wherein the battery powered light source is defined by a plurality of LED light sources arranged in spaced relationship on a front surface of a printed circuit board.

12. A lighting device as recited in claim 11, wherein a contact switch is located on a rear surface of the printed circuit board for activating the LED light sources upon insertion of the distal end portion of the surgical instrument.

13. A lighting device as recited in claim 12, wherein a pair of battery cells are operatively associated the rear surface of the printed circuit board for powering the LED light sources.

14. A lighting device as recited in claim 11, wherein a lens is disposed at the distal end of the outer housing portion for focusing the LED light sources.

15. A lighting device as recited in claim 10, wherein a compliant securement ring is disposed in the outer body portion for mechanically engaging and retaining the distal end portion of the surgical instrument.

16. A lighting device as recited in claim 10, wherein a securement screw is located on the planar upper surface portion of the outer body portion and is operatively associated with the inner cavity of the inner body portion for selectively engaging the distal end portion of the surgical instrument.

17. A lighting device as recited in claim 10, wherein an elongated securement beam is pivotably attached to the proximal end of the outer body portion about an axis that extends perpendicular to a longitudinal axis of the surgical instrument and it includes a proximal clasp for frictionally engaging a proximal end portion of the surgical instrument.

18. A lighting device as recited in claim 10, wherein a securement cam arm is rotational attached to a proximal end cap of the outer body portion about an axis that extends parallel to a longitudinal axis of the surgical instrument and it includes a cam surface for frictionally engaging the distal end portion of the surgical instrument and an outer tang for selectively engaging a retaining boss projecting from the proximal end cap.

* * * * *